US009695112B2

(12) United States Patent
Moriwaki et al.

(10) Patent No.: US 9,695,112 B2
(45) Date of Patent: Jul. 4, 2017

(54) METHOD FOR SYNTHESIZING OPTICALLY ACTIVE α-AMINO ACID USING CHIRAL METAL COMPLEX COMPRISING AXIALLY CHIRAL N-(2-ACYLARYL)-2-[5,7-DIHYDRO-6H-DIBENZO[C,E]AZEPIN-6-YL] ACETAMIDE COMPOUND AND AMINO ACID

(71) Applicant: HAMARI CHEMICALS, LTD., Osaka (JP)

(72) Inventors: Hiroki Moriwaki, Osaka (JP); Aki Kawashima, Osaka (JP); Ryosuke Takeda, Osaka (JP); Akie Kawamura, Osaka (JP); Vadim A. Soloshonok, Norman, OK (US)

(73) Assignee: HAMARI CHEMICALS, LTD., Osaka (JP)

( * ) Notice: Subject to any disclaimer, the term of this patent is extended or adjusted under 35 U.S.C. 154(b) by 0 days.

(21) Appl. No.: 14/890,887

(22) PCT Filed: Mar. 27, 2014

(86) PCT No.: PCT/JP2014/058974
§ 371 (c)(1),
(2) Date: Nov. 12, 2015

(87) PCT Pub. No.: WO2014/188783
PCT Pub. Date: Nov. 27, 2014

(65) Prior Publication Data
US 2016/0102045 A1    Apr. 14, 2016

(30) Foreign Application Priority Data
May 24, 2013    (JP) ................. 2013-110171

(51) Int. Cl.
C07D 213/55    (2006.01)
C07C 227/32    (2006.01)
C07D 223/14    (2006.01)
C07B 53/00     (2006.01)
C07C 319/20    (2006.01)
C07C 231/18    (2006.01)
C07F 15/04     (2006.01)

(52) U.S. Cl.
CPC ............ C07C 227/32 (2013.01); C07B 53/00 (2013.01); C07C 231/18 (2013.01); C07C 319/20 (2013.01); C07D 213/55 (2013.01); C07D 223/14 (2013.01); C07F 15/045 (2013.01); C07B 2200/07 (2013.01); C07C 2101/02 (2013.01)

(58) Field of Classification Search
CPC .................................................. C07D 213/55
See application file for complete search history.

(56) References Cited

U.S. PATENT DOCUMENTS
2012/0130116 A1    5/2012    Aikawa et al.

FOREIGN PATENT DOCUMENTS
JP    2011057665 A    3/2011

OTHER PUBLICATIONS

Moriwaki et al. Practical asymmetric synthesis of alpha-amino acids using the new generation of axially chiral Ni(II) chelated glycine Schiff bases, Peptide Science (2013), 50th, 115-118.*
International Preliminary Report on Patentability for Application No. PCT/JP2014/058974, dated Nov. 24, 2015. (English Translation).
E. Juaristi et al., Highly Diastereoselective Alkylation of 1-Benzoyl-2-alkyl-3-(1'-methylbenzyl)imidazolidin-4-ones, J. Org. Chem., 1995, 60, p. 6408-6415.

(Continued)

Primary Examiner — Brian McDowell
(74) Attorney, Agent, or Firm — Marshall, Gerstein & Borun LLP

(57) ABSTRACT

Objects of the present invention are to provide an industrially applicable method for producing an optically active α-amino acid in high yield and in a highly enantioselective manner, to provide a simple production method of an optically active α,α-disubstituted α-amino acid, and to provide an intermediate useful for the above production methods of an optically active α-amino acid and an optically active α,α-disubstituted α-amino acid.

The present invention provides a production method of an optically active α-amino acid or a salt thereof, the production method comprising introducing a substituent into the α carbon in the α-amino acid moiety of a metal complex represented by the following Formula (1):

(1)

by an alkylation reaction, an aldol reaction, the Michael reaction, or the Mannich reaction, and releasing an optically pure α-amino acid enantiomer or a salt thereof by acid decomposition of the metal complex.

2 Claims, 14 Drawing Sheets

(56) References Cited

OTHER PUBLICATIONS

R.M. Williams et al., Efficient Asymmetric Synthesis of N-tert-Butoxycarbonyl α-Aminoacids Using 4-tert-Butoxycarbonyl-5,6-Diphenylmorpholin-2-One: (R)-(N-tert-Butoxycarbonyl) Allylglycine, Organic Syntheses, vol. 80, p. 31 (2003).

V.A. Soloshonok et al., Michael Addition Reactions between Chiral Equivalents of a Nucleophilic Glycine and (S)- or (R)-3-[(E)-Enoyl]-4-phenyl-1,3-oxazolidin-2-ones as a General Method for Efficient Preparation of β-Substituted Pyroglutamic Acids. Case of Topographically Controlled Stereoselectivity, J. Am. Chem. Soc., 2005, 127, 15296-15303.

Luo, X. et al., Catalytic asymmetric Michael addition of α,β-unsaturated aldehydes to Ni(II) complexes of the Schiff base of glycine, Organic & Biomolecular Chemistry, 2001, vol. 9, No. 3, p. 793-801.

Ellis, T.K. et al., Design, Synthesis, and Evaluation of a New Generation of Modular Nucleophilic Glycine Equivalents for the Efficient Synthesis of Sterically Constrained α-Amino Acids, J. Org. Chem., 2006, vol. 71, No. 22, p. 8572-8578.

Soloshonok, V.A. et al, Application of modular nucleophilic glycine equivalents for truly practical asymmetric synthesis of β-substituted pyroglutamic acids, Tetrahedron Letters, 2005, vol. 46, No. 7, p. 1107-1110.

Ellis, T.K. et al., New generation of nucleophilic glycine equivalents, Tetrahedron Letters, 2005, vol. 46, No. 6, p. 941-944.

Schollkopf et al., Asymmetric Syntheses via Heterocyclic Intermediates; VIII1. Enantioselective Synthesis of (R)-α-Methyl-α-amino Acids using L-Valine as Chiral Auxiliary Reagent, Synthesis, 1981, p. 969-971.

International Search Report and Written Opinion for Application No. PCT/JP2014/058974, dated Jun. 17, 2014.

Luo, X. et al., Catalytic asymmetric Michael addition of α,β-unsaturated aldehydes to Ni(II) complexes of the Schiff base of glycine, Organic & Biomolecular Chemistry, 2011, vol. 9, No. 3, p. 793-801.

Selected parts of the symposium proceedings including Moriwaki et al., *Peptide Science*, 2013, 50th, pp. 115-118, published in Mar. 2014.

4th Asia-Pacific International Peptide Symposium, APIPS 2013 Abstracts and English translation of the colophon of the APIPS 2013 Abstracts, published on Oct. 10, 2013.

\* cited by examiner

METHOD FOR SYNTHESIZING OPTICALLY ACTIVE α-AMINO ACID USING CHIRAL METAL COMPLEX COMPRISING AXIALLY CHIRAL N-(2-ACYLARYL)-2-[5,7-DIHYDRO-6H-DIBENZO[C,E]AZEPIN-6-YL] ACETAMIDE COMPOUND AND AMINO ACID

TECHNICAL FIELD

The present invention relates to a synthetic method of an optically active α-amino acid using an axially chiral N-(2-acylaryl)-2-[5,7-dihydro-6H-dibenzo[c,e]azepin-6-yl]acetamide compound as a template. The present invention also relates to a metal complex used as an intermediate for the synthetic method, the metal complex having, as a ligand, a condensate of an α-amino acid and an N-(2-acylaryl)-2-[5,7-dihydro-6H-dibenzo[c,e]azepin-6-yl]acetamide compound.

BACKGROUND ART

Optically pure α-amino acids are an important compound group as a building block for, for example, designing various physiologically active substances and drugs. Recently, it has been frequently reported that, in particular, an α-amino acid having a side chain which natural α-amino acids do not have, and substances containing the same have unique physiological activities. Therefore, a process for conveniently obtaining such an α-amino acid in an optically pure form is desired. Also, peptides and proteins containing α,α-disubstituted α-amino acids in their amino acid sequence, which have a quaternary carbon atom at the α-position, have a more stable higher-order structure and an improved stability against hydrolytic enzymes compared to naturally occurring ones. Therefore, the importance of α,α-disubstituted α-amino acids in drug development has been increasing, and recently, the development of a process for conveniently obtaining an optically active form of α,α-disubstituted α-amino acids is an urgent issue.

As a classic production method of an optically active α-amino acid having an unnatural side chain, methods using diastereoselective alkylation reactions and addition reactions of a chiral glycine enolate equivalent and various electrophiles have been reported. For example, Non-patent Literature 1 discloses a method using a chiral bislactim ether as a chiral glycine equivalent. However, this method needs several steps for synthesis of bislactim ether, as the chiral glycine equivalent. Moreover, a reagent which is expensive and difficult to handle is required for conversion of amide to imidate and an intended amino acid derivative is required to be separated from other amino acid derivatives, such as valine, which are used as a chiral auxiliary. Therefore, the method is difficult to apply to large-scale synthesis. Non-patent Literature 2 discloses a method using imidazolidinone as a chiral glycine equivalent. However, this method needs several steps for synthesis of 2-alkyl-1,3-imidazolidinone, as the chiral glycine equivalent. In addition, the resulting imidazolidinone derivative is an isomeric mixture and therefore, needs to be subjected to separation by chromatography or the like. Moreover, this method needs expensive pivalaldehyde. Therefore, the method is difficult to apply to large-scale synthesis. Non-patent Literature 3 discloses a method using 5,6-diphenylmorpholin-2-one as a chiral glycine equivalent. However, the chiral substance 1,2-diphenyl-2-aminoethanol as a raw material of this method is expensive, and the method needs several steps for synthesis of 5,6-diphenylmorpholin-2-one, as the chiral glycine equivalent. In addition, 1,2-diphenyl-2-aminoethanol, which is used as a chiral auxiliary, is usually removed by a reduction reaction when obtaining an amino acid in the final step, and thus, loses the chirality. Therefore, the chiral auxiliary cannot be recovered. Accordingly, there is a serious problem of cost efficiency also in this method, and the method is difficult to apply to large-scale synthesis. Moreover, in a method disclosed in Non-patent Literature 4, a chiral nickel (II) complex using proline as a chiral source is used as a chiral glycine equivalent, and the Michael reaction thereof is reported. In addition, a large number of applications of the nickel (II) complex to a diastereoselective alkylation reaction, a diastereoselective aldol reaction, and a diastereoselective Mannich reaction are also reported. However, in all the reactions, a chiral center of proline is stereochemically unstable and is prone to epimerization. Therefore, the recovery and recycling of ligands are difficult in this method.

The above four methods are prominent examples of the method using a chiral glycine enolate equivalent for the production of an optically active α-amino acid having an unnatural side chain. However, all the methods have disadvantages that hinder their industrial application on a multi kilogram scale, and the development of a novel method which can eliminate such disadvantages has been demanded.

CITATION LIST

Non-Patent Literature

Non-PTL 1: U. Schollkopf et al., Angew. Chem. Int. Ed. Engl., 1981, 20, 798.

Non-PTL 2: E. Juaristi et al., J. Org. Chem., 1995, 60, 6408.

Non-PTL 3: R. M. Williams et al., Org. Synth., 2003, 80, 31

Non-PTL 4: V. A. Soloshonok et al., J. Am. Chem. Soc., 2005, 127, 15296.

SUMMARY OF INVENTION

Technical Problem

In view of the above situations, an object of the present invention is to provide a method for producing various optically active α-amino acids having different side chains in high yield and in a highly enantioselective manner, the method being industrially applicable on a multi kilogram scale. An another object of the present invention is to provide a simple production method of optically active α,α-disubstituted α-amino acids. A further object of the present invention is to provide an intermediate useful for the above production methods of optically active α-amino acids and optically active α,α-disubstituted α-amino acids.

Solution to Problem

That is, the present invention relates to the following.

[1] A production method of an optically active α-amino acid or a salt thereof, the production method comprising introducing a substituent into the α carbon in the α-amino acid moiety of a metal complex represented by the following Formula (1):

(1)

(wherein $R^1$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

$R^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group;

$R^3$ and $R^4$ each independently denote hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two $R^3$s may be the same or different;
the two $R^4$s may be the same or different;
$R^3$ and $R^4$ may form a ring together with the carbon atoms to which they are bonded;

$R^5$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, an optionally substituted carboxyl group (—$CO_2R^7$), or a halogen atom;

the two $R^5$s may be the same or different;

$R^6$ denotes hydrogen, an optionally substituted alkyl group, an optionally substituted cycloalkyl group, or a halogen atom;

the two $R^6$s may be the same or different;
the two $R^6$s may form a ring together with the carbon atom to which they are bonded;

$R^7$ denotes hydrogen, an optionally substituted alkyl group, an optionally substituted aryl group, or an optionally substituted heteroaryl group;

$R^8$ denotes hydrogen, an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group;

* denotes a chiral axis; and
M denotes a divalent metallic cation)

by an alkylation reaction, an aldol reaction, the Michael reaction, or the Mannich reaction; and releasing the substituent-introduced α-amino acid or a salt thereof by acid decomposition.

[2] The production method according to the above [1], wherein the metal complex is represented by Formula (1) in which $R^8$ is hydrogen, namely represented by the following Formula (1-1):

(1-1)

(wherein $R^1$ to $R^6$, * and M have the same meanings as defined in the above [1]).

[3] The production method according to the above [1] or [2], wherein the metal complex is represented by Formula (1) in which $R^1$ is hydrogen, chlorine, a methyl group, or a nitro group;

in each of the two pairs of $R^3$ and $R^4$, $R^3$ and $R^4$ form an aromatic or aliphatic cyclic structure together with the aromatic-ring carbon atoms to which they are bonded;

$R^5$ and $R^6$ are each hydrogen; and
M denotes a nickel cation, a copper cation, a palladium cation, or a platinum cation, namely represented by the following Formula (1b):

(1b)

(wherein $R^2$, $R^8$ and * have the same meanings as defined in the above [1]).

[4] The production method according to any one of the above [1] to [3], further comprising a step of enhancing the optical purity of the α carbon after the introduction of a substituent into the α carbon and before the acid decomposition.

[5] The production method according to the above [4], wherein the step of enhancing the optical purity is performed by heating under basic conditions.

[6] The production method according to any one of the above [1] to [5], wherein the optically active α-amino acid or a salt thereof is an unnatural amino acid or a salt thereof.

[7] A production method of an optically active disubstituted α-amino acid or a salt thereof, the production method comprising introducing a substituent into the cc carbon in the α-amino acid moiety of the metal complex represented by Formula (1-1) in the above [2] by an alkylation reaction, an aldol reaction, the Michael reaction, or the Mannich reaction to give a metal complex represented by the following Formula (1-2):

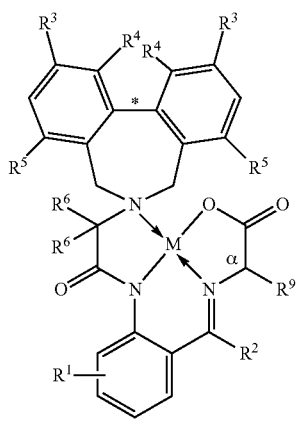

(1-2)

(wherein $R^1$ to $R^6$, * and M have the same meanings as defined in the above [1]; and $R^9$ denotes an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, or an optionally substituted aryloxycarbonyl group); and introducing another substituent into the α carbon by an alkylation reaction, an aldol reaction, the Michael reaction, or the Mannich reaction.

[8] A metal complex represented by Formula (1-1):

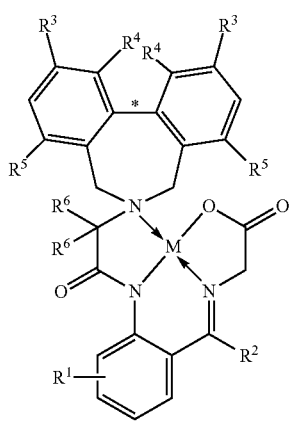

(1-1)

(wherein $R^1$ to $R^6$, * and M have the same meanings as defined in the above [1]).

[9] A metal complex represented by Formula (2):

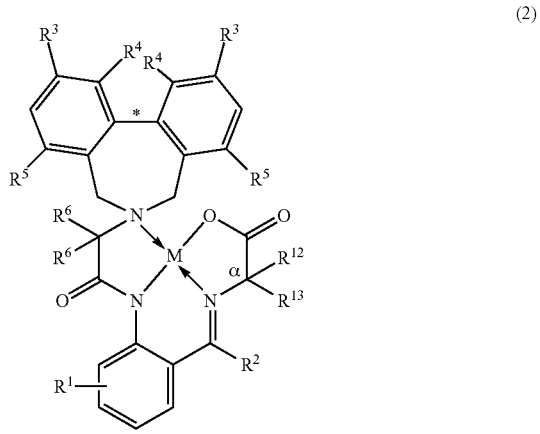

(2)

(wherein $R^1$ to $R^6$, * and M have the same meanings as defined in the above [1]; and $R^{12}$ and $R^{13}$ each independently denote an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, an optionally substituted aryloxycarbonyl group, or a halogen atom).

[10] A metal complex represented by Formula (2):

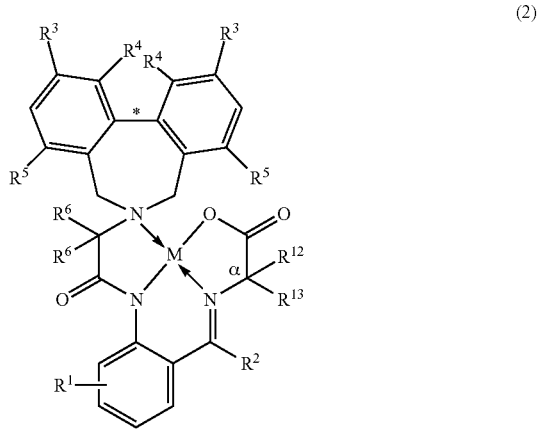

(2)

(wherein $R^1$ to $R^6$, * and M have the same meanings as defined in the above [1]; and $R^{12}$ and $R^{13}$ each independently denote an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, an optionally substituted aryloxycarbonyl group, or a halogen atom, and $R^{12}$ and $R^{13}$ may form a ring together with the carbon atom to which they are bonded).

[11] The metal complex according to any one of the above [8] to [10],
wherein $R^1$ is hydrogen, chlorine, a methyl group, or a nitro group;
in each of the two pairs of $R^3$ and $R^4$, $R^3$ and $R^4$ form an aromatic or aliphatic cyclic structure together with the aromatic-ring carbon atoms to which they are bonded;
$R^5$ and $R^6$ are each hydrogen; and
$R^2$ is an aryl group represented by Formula (1-1a):

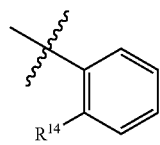

(1-1a)

(wherein $R^{14}$ denotes a hydrogen atom or a halogen atom).

Advantageous Effects of Invention

According to the present invention, an optically active α-amino acid having a desired chirality can be produced in high yield, in a highly enantioselective manner, and on a multi kilogram scale. Moreover, according to the present invention, an optically active α,α-disubstituted α-amino acid, the importance of which in drug development has been increasing, can also be produced in a high-yield, highly enantioselective and simple manner.

DESCRIPTION OF EMBODIMENTS

Figure 1:
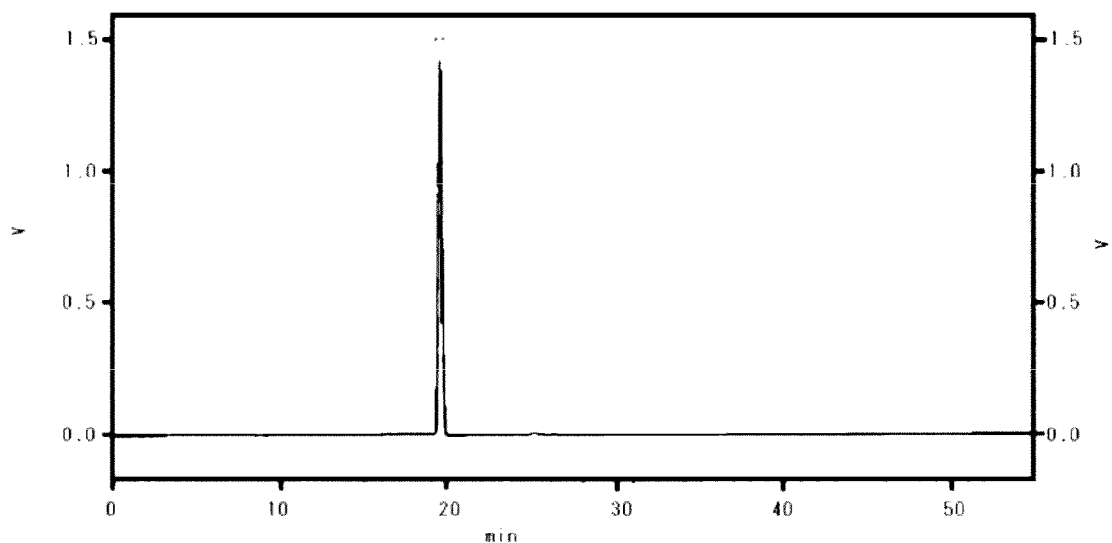
FIG. 1 shows a HPLC chromatogram of the compound prepared in Example 1-2.

The present invention relates to a production method of an optically active α-amino acid and an optically active α,α-disubstituted α-amino acid having a desired chirality with use of the stereochemical structure of an optically active N-(2-acylaryl)-2-[5,7-dihydro-6H-dibenzo[c,e]azepin-6-yl] acetamide compound represented by Formula (3):

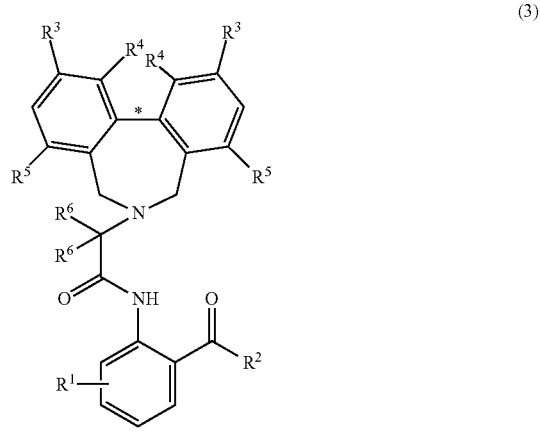

(3)

(wherein $R^1$ to $R^6$ and * have the same meanings as defined in the above [1]).

General descriptions of the chemical reactions according to the present invention are as follows.

A side chain is introduced into the α carbon in the α-amino acid moiety of a metal complex represented by Formula (1):

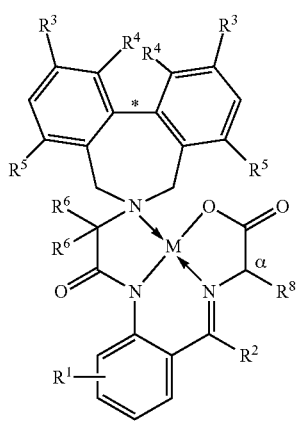

(1)

(wherein $R^1$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

$R^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group;

$R^3$ and $R^4$ each independently denote hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two $R^3$s may be the same or different;

the two $R^4$s may be the same or different;

$R^3$ and $R^4$ may form a ring together with the carbon atoms to which they are bonded;

$R^5$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, an optionally substituted carboxyl group (—$CO_2R^7$), or a halogen atom;

the two $R^5$s may be the same or different;

$R^6$ denotes hydrogen, an optionally substituted alkyl group, an optionally substituted cycloalkyl group, or a halogen atom;

the two $R^6$s may be the same or different;

the two $R^6$s may form a ring together with the carbon atom to which they are bonded;

$R^7$ denotes hydrogen, an optionally substituted alkyl group, an optionally substituted aryl group, or an optionally substituted heteroaryl group;

$R^8$ denotes hydrogen, an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group;

* denotes a chiral axis; and

M denotes a divalent metallic cation), and the side chain-introduced α-amino acid is released by acid decomposition.

Moreover, the reactions according to the present invention include a reaction in which an α-amino acid containing a quaternary α carbon atom is separated by acid decomposition of a metal complex represented by Formula (2):

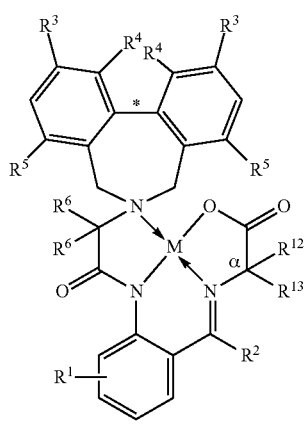

(2)

(wherein $R^1$ to $R^6$, * and M have the same meanings as defined in the above Formula (1); and $R^{12}$ and $R^{13}$ each independently denote an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, an optionally substituted aryloxycarbonyl group, or a halogen atom, and $R^{12}$ and $R^{13}$ may form a ring together with the carbon atom to which they are bonded).

The above $R^{12}$ may have the same meaning as $R^9$ or $R^{11}$ below, and the above $R^{13}$ may have the same meaning as $R^{10}$ below. That is, the compound represented by Formula (2) includes compounds represented by Formula (2-1) and Formula (2-1') below.

In one aspect of the present invention,

[A-1] an imine compound produced by condensation of a compound represented by Formula (3) and glycine represented by Formula (4) is reacted with a metal salt MXn represented by Formula (9) to give a metal complex represented by Formula (1-1);

[A-2] a side chain is introduced into the α carbon in the α-amino acid moiety of the metal complex represented by Formula (1-1) by, for example, a reaction with an electrophile, such as an alkylation reaction, an aldol reaction, the Michael reaction, and the Mannich reaction to give a metal complex represented by Formula (1-2); and then

[A-3] the metal complex represented by Formula (1-2) is subjected to acid decomposition to give an optically active α-amino acid represented by Formula (6) in a highly enantioselective manner.

Moreover, in another aspect of the present invention,
[B-1] after the step [A-2], another side chain is introduced into the α carbon in the α-amino acid moiety by an alkylation reaction, an aldol reaction, the Michael reaction, the Mannich reaction, or the like to give a metal complex represented by Formula (2-1); and then
[B-2] the metal complex represented by Formula (2-1) is subjected to acid decomposition to give an optically active α,α-disubstituted α-amino acid represented by Formula (7) in a highly enantioselective manner.

In still another aspect of the present invention,
[C-1] an imine compound produced by condensation of the compound represented by Formula (3) and an α-amino acid represented by Formula (5) is reacted with the metal salt MXn represented by Formula (9) to give a metal complex represented by Formula (1-1');
[C-2] a side chain is introduced into the α carbon in the α-amino acid moiety of the metal complex represented by Formula (1-1') by an alkylation reaction, an aldol reaction, the Michael reaction, the Mannich reaction, or the like to give a metal complex represented by Formula (2-1'); and then
[C-3] the metal complex represented by Formula (2-1') is subjected to acid decomposition to give an optically active α,α-disubstituted α-amino acid represented by Formula (8) in a highly enantioselective manner.

A step of heating the compound obtained in the step [A-2] or [C-1] may be included. As described below, the configuration of the α carbon in the α-amino acid moiety of the metal complex can be converted to either S- or R-configuration by heating, in accordance with the configuration of a chiral axis of said metal complex.

The whole scheme of the chemical reactions according to the present invention (the steps [A-1] to [A-3], [B-1] to [B-2], and [C-1] to [C-3]) is shown below.

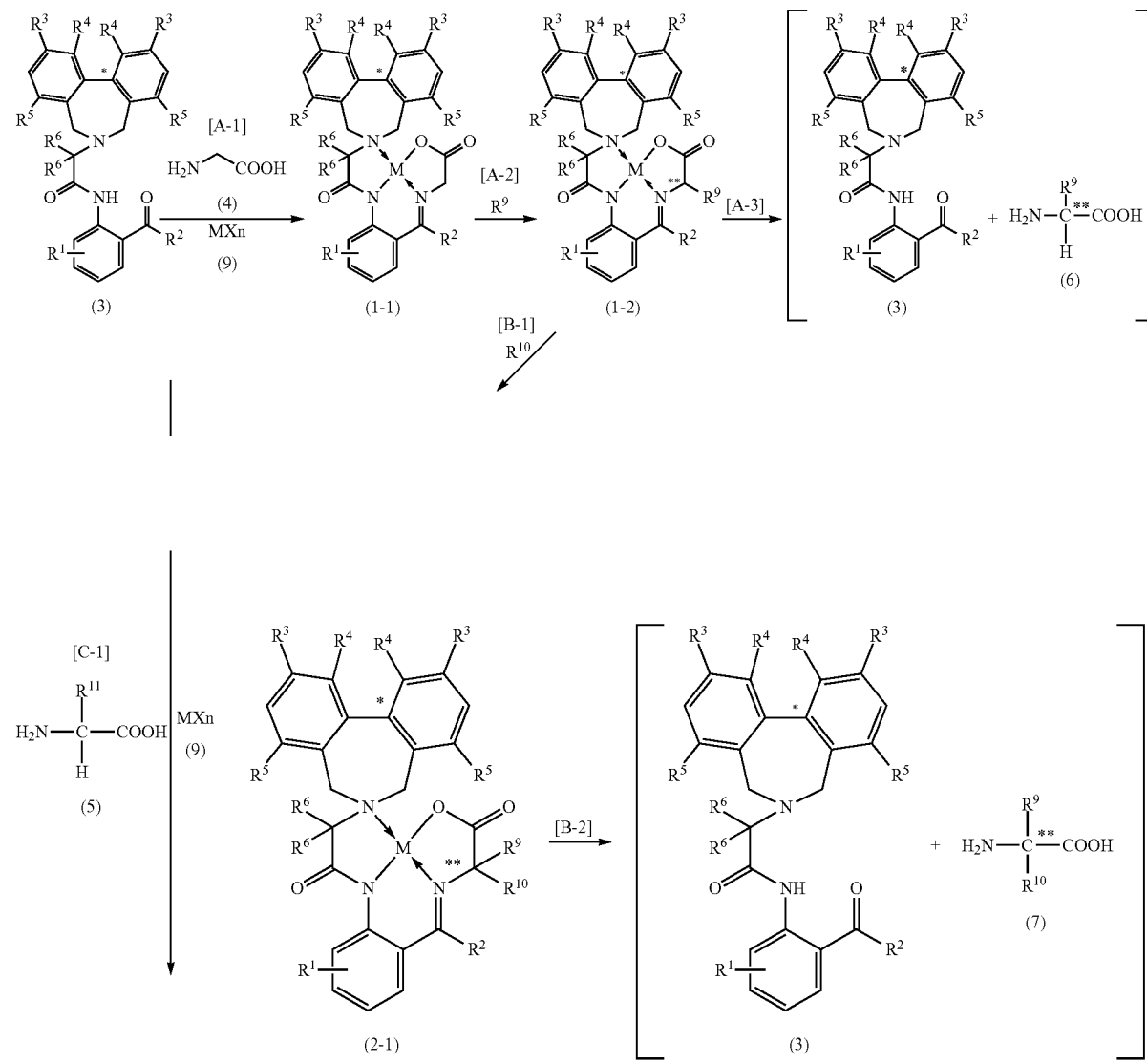

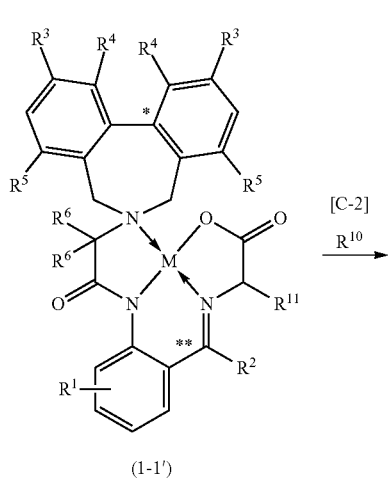
(1-1')

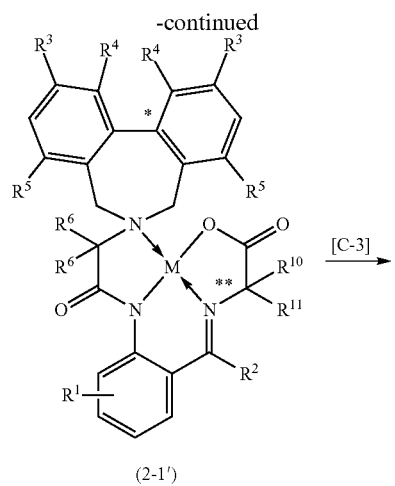
(2-1')

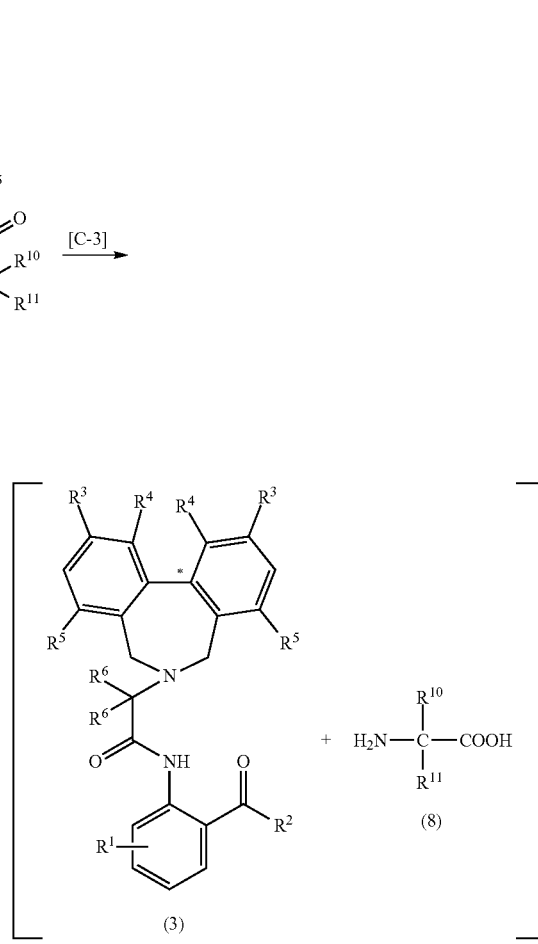
(3)

The compound represented by Formula (3) has two optical isomers represented by Formula (3-S-isomer) and Formula (3-R-isomer).

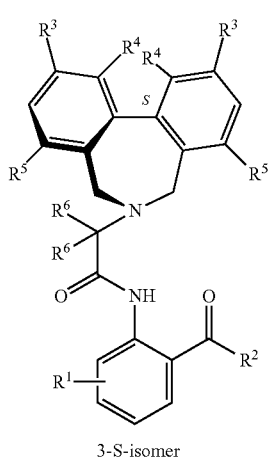
3-S-isomer

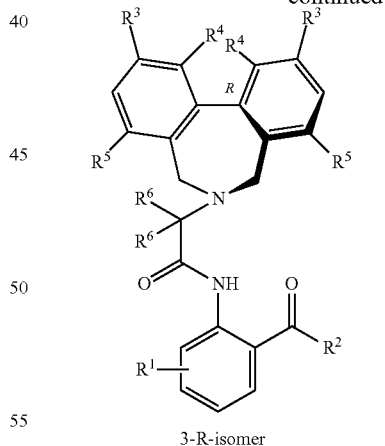
3-R-isomer

In the optically active α-amino acid production method of the present invention, the configuration of the α carbon of an optically active α-amino acid finally obtained is controlled by the stereochemical structure in Formula (3).

That is, the present invention includes a method for producing an optically active α-amino acid having a desired chirality and being optically pure or having a high optical purity by using an appropriate optical isomer, which is represented by Formula (3-S-isomer) or Formula (3-R-isomer).

The present invention will be described in detail below. First, the compound represented by Formula (3):

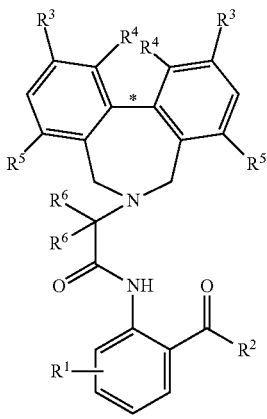

(3)

(wherein $R^1$, $R^2$, $R^3$, $R^4$, $R^5$, $R^6$, and * have the same meanings as defined in the above Formula (1)) will be described.

The "alkyl group" in the optionally substituted alkyl group denoted by $R^1$ is not particularly limited and may be linear or branched. Examples of the "alkyl group" include alkyl groups having 1 to 20 carbon atoms, specifically, a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, a dodecyl group, a pentadecyl group, a hexadecyl group, and an octadecyl group.

The "alkynyl group" in the optionally substituted alkynyl group denoted by $R^1$ is not particularly limited. Examples of the "alkynyl group" include alkynyl groups having 2 to 20 carbon atoms, preferably alkynyl groups having 2 to 10 carbon atoms, specifically, an ethynyl group and a propynyl group.

The "alkenyl group" in the optionally substituted alkenyl group denoted by $R^1$ is not particularly limited. Examples of the "alkenyl group" include alkenyl groups having 2 to 20 carbon atoms, preferably alkenyl groups having 2 to 10 carbon atoms, specifically, a vinyl group, an allyl group, a butenyl group, and a hexenyl group.

The "alkoxy group" in the optionally substituted alkoxy group denoted by $R^1$ is not particularly limited. Examples of the "alkoxy group" include alkoxy groups having 1 to 20 carbon atoms, preferably alkoxy groups having 1 to 10 carbon atoms, specifically, a methoxy group, an ethoxy group, a propoxy group, an isopropoxy group, a butoxy group, an isobutoxy group, a tert-butoxy group, and a pentyloxy group.

The "cycloalkyl group" in the optionally substituted cycloalkyl group denoted by $R^1$ is not particularly limited. Examples of the "cycloalkyl group" include cycloalkyl groups having 3 to 12 carbon atoms, preferably cycloalkyl groups having 3 to 10 carbon atoms, specifically, a cyclopropyl group, a cyclobutyl group, a cyclopentyl group, a cyclohexyl group, and a cycloheptyl group.

The "aryl group" in the optionally substituted aryl group denoted by $R^1$ is not particularly limited. Examples of the "aryl group" include aryl groups having 6 to 20 carbon atoms, specifically, a phenyl group, a 1-naphthyl group, a 2-naphthyl group, an anthryl group, a phenanthryl group, a 2-biphenyl group, a 3-biphenyl group, a 4-biphenyl group, and a terphenyl group.

The "heteroaryl group" in the optionally substituted heteroaryl group denoted by $R^1$ is not particularly limited. Examples of the "heteroaryl group" include heteroaryl groups having preferably 1 to 3 hetero atoms selected from a nitrogen atom, a sulfur atom, an oxygen atom, etc., specifically, a furanyl group, a thienyl group, an oxazolyl group, an isoxazolyl group, a thiazolyl group, an isothiazolyl group, a pyrrolyl group, an imidazolyl group, a pyrazolyl group, a pyridyl group, a pyrimidinyl group, a pyrazinyl group, a phthalazinyl group, a triazinyl group, an indolyl group, an isoindolyl group, a quinolyl group, an isoquinolyl group, a benzofuranyl group, and a dibenzofuranyl group.

The halogen atom denoted by $R^1$ is not particularly limited. Examples of the halogen atom include a fluorine atom, a chlorine atom, a bromine atom, and an iodine atom.

The "substituent" in $R^1$ is not particularly limited. Examples of the "substituent" include an alkyl group (for example, a methyl group, an ethyl group, a propyl group, an isopropyl group, a butyl group, an isobutyl group, a tert-butyl group, a pentyl group, a hexyl group, and the like); an alkynyl group (for example, an ethynyl group, a propynyl group, and the like); an alkenyl group (for example, a vinyl group, an allyl group, a butenyl group, a hexenyl group, and the like); an alkoxy group (for example, a methoxy group, an ethoxy group, a propoxy group, an isopropoxy group, a butoxy group, an isobutoxy group, a tert-butoxy group, a pentyloxy group, and the like); a cycloalkyl group (for example, a cyclopropyl group, a cyclobutyl group, a cyclopentyl group, a cyclohexyl group, a cycloheptyl group, and the like); an aryl group (for example, a phenyl group, a 1-naphthyl group, a 2-naphthyl group, an anthryl group, a phenanthryl group, a 2-biphenyl group, a 3-biphenyl group, a 4-biphenyl group, a terphenyl group, and the like); a heteroaryl group (for example, a furanyl group, a thienyl group, an oxazolyl group, an isoxazolyl group, a thiazolyl group, an isothiazolyl group, a pyrrolyl group, an imidazolyl group, a pyrazolyl group, a pyridyl group, a pyrimidinyl group, a pyrazinyl group, a phthalazinyl group, a triazinyl group, an indolyl group, an isoindolyl group, a quinolyl group, an isoquinolyl group, a benzofuranyl group, a dibenzofuranyl group, and the like); an aralkyl group (for example, a benzyl group, a phenylethyl group, a phenylpropyl group, a naphthylmethyl group, and the like); a haloalkyl group (for example, a trifluoromethyl group, a trichloromethyl group, and the like); a halogenated alkoxy group (for example, a fluoromethoxy group, a difluoromethoxy group, a trifluoromethoxy group, a trifluoroethoxy group, a tetrafluoroethoxy group, and the like); a halogen atom (for example, a fluorine atom, a chlorine atom, a bromine atom, an iodine atom, and the like); a hydroxyl group; a protected hydroxyl group (examples of the protecting group for the hydroxyl group include an acetyl group, a benzoyl group, a methoxymethyl group, a tetrahydropyranyl group, a trimethylsilyl group, a tert-butyldimethylsilyl group, a carbonate ester group, and the like); an amino group; a protected amino group (examples of the protecting group for the amino group include a formyl group, an acetyl group, a benzoyl group, a benzyloxycarbonyl group, a phthaloyl group, a carbamoyl group, a ureido group, and the like); an arylamino group; a heteroarylamino group; a mercapto group; a nitro group; a nitrile group; a carboxyl group; and an alkoxycarbonyl group. The number of carbon atoms in these substituents is not particularly limited, but preferably 1 to 10.

The number of "substituents" in $R^1$ is not particularly limited. The number of "substituents" in $R^1$ has only to be, for example, 1 to 4, and is preferably 1 to 2, and more preferably 1.

The position at which $R^1$ is bonded is not particularly limited. The position at which $R^1$ is bonded may be any of positions 3, 4, 5, and 6, but is preferably position 4.

Examples of the optionally substituted alkyl group, the optionally substituted alkynyl group, the optionally substituted alkenyl group, the optionally substituted cycloalkyl group, the optionally substituted aryl group, or the optionally substituted heteroaryl group, denoted by $R^2$ include those listed for $R^1$, for example. Examples of the substituent in this case include those listed for $R^1$, for example.

Examples of the optionally substituted alkyl group, the optionally substituted alkynyl group, the optionally substituted alkenyl group, the optionally substituted alkoxy group, the optionally substituted cycloalkyl group, the optionally substituted aryl group, the optionally substituted heteroaryl group, or the halogen atom, denoted by $R^3$ or $R^4$ include those listed for $R^1$, for example. Examples of the substituent in this case include those listed for $R^1$, for example.

The ring formed of $R^3$ and $R^4$ together with the carbon atoms to which they are bonded is not particularly limited, and may be an alicyclic ring or an aromatic ring. Examples of the above ring include a cycloalkane ring, a cycloalkene ring, an aryl ring, and a heteroaryl ring, specifically, cyclopentane, cyclohexane, cyclopentene, cyclohexene, a benzene ring, a naphthalene ring, and a pyridine ring. The number of carbon atoms in the above ring is not particularly limited, but preferably 3 to 15.

Examples of the optionally substituted alkyl group, the optionally substituted alkynyl group, the optionally substituted alkenyl group, the optionally substituted alkoxy group, the optionally substituted cycloalkyl group, the optionally substituted aryl group, the optionally substituted heteroaryl group, or the halogen atom, denoted by $R^5$ include those listed for $R^1$, for example. Examples of the substituent in this case include those listed for $R^1$, for example.

Examples of the optionally substituted alkyl group, the optionally substituted cycloalkyl group, or the halogen atom, denoted by $R^6$ include those listed for $R^1$, for example. Examples of the substituent in this case include those listed for $R^1$, for example.

$R^1$ is preferably hydrogen, chlorine, a methyl group, or a nitro group.

$R^2$ is preferably an optionally substituted aryl group, and more preferably a phenyl group, or a phenyl group substituted with a halogen atom.

The two $R^3$s are preferably the same. Also, the two $R^4$s are preferably the same.

Also, $R^3$ and $R^4$ more preferably form a ring together with the carbon atoms to which they are bonded, as represented in the following Formula (3-1):

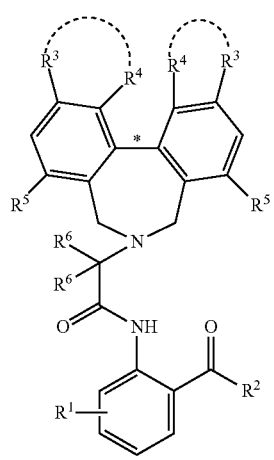

(3-1)

(wherein $R^1$, $R^2$, $R^5$, $R^6$, and * have the same meanings as defined above).

The two $R^5$s are preferably the same, and more preferably each hydrogen.

The two $R^6$s are preferably the same, and more preferably each hydrogen.

Moreover, the above Formula (3-1) is preferably a compound represented by Formula (3-1a):

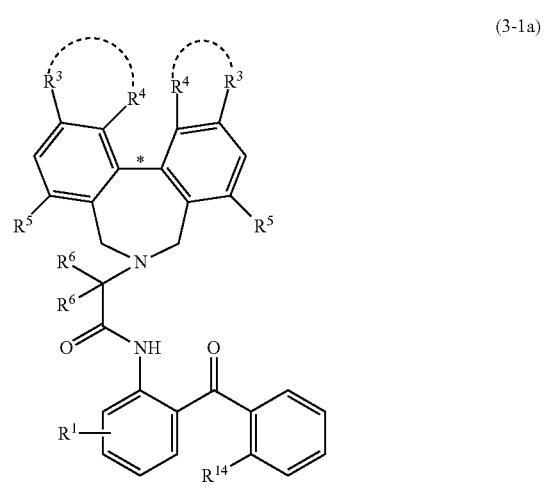

(3-1a)

(wherein $R^1$, $R^3$, $R^4$, $R^5$, $R^6$, and * have the same meanings as defined above; and $R^{14}$ denotes a hydrogen atom or a halogen atom).

Examples of the compound represented by Formula (3) or a salt thereof include the following compounds represented by Structural Formulae (3-1-1) to (3-1-7) or salts thereof.

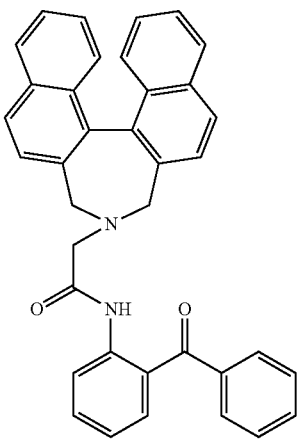

(3-1-1)

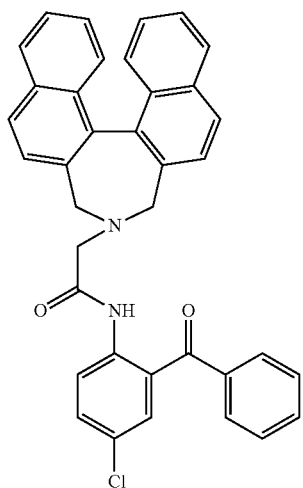
(3-1-2)
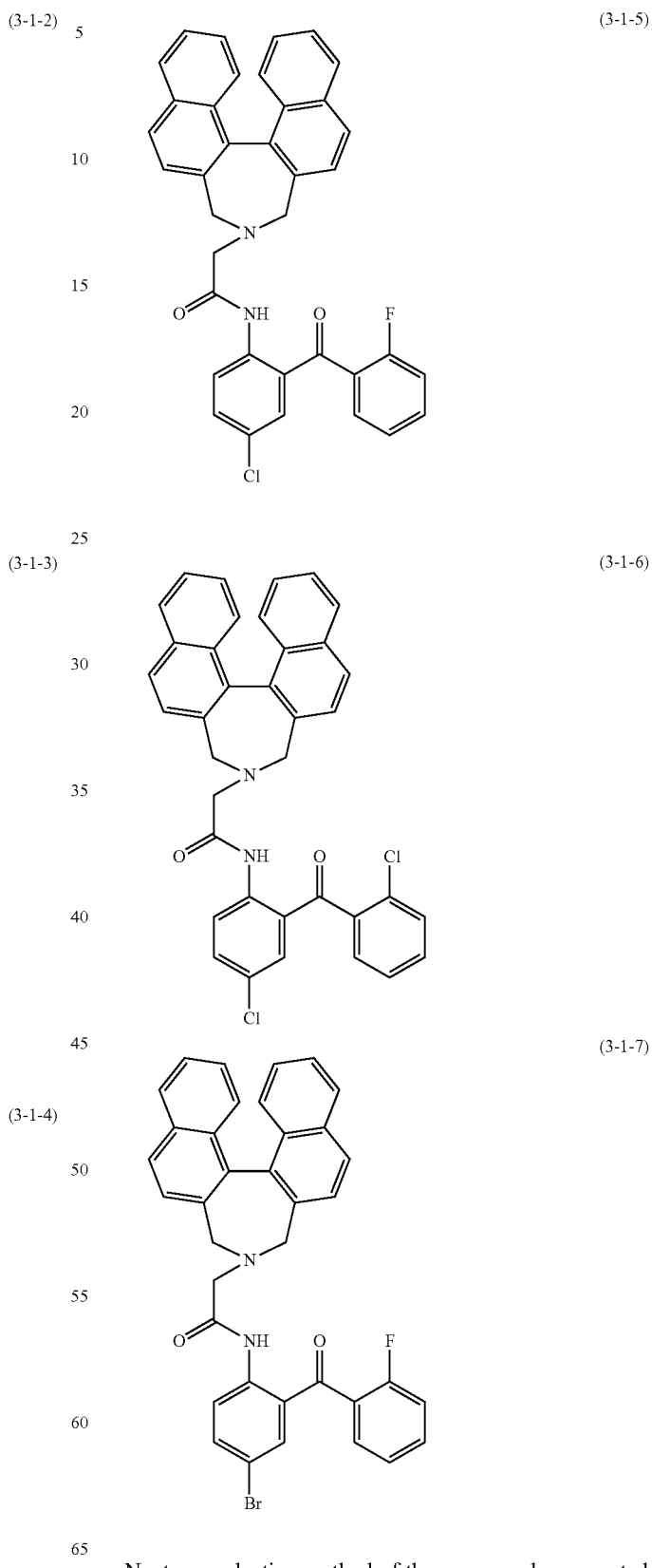
Next, a production method of the compound represented by Formula (3) will be described.

This compound may be produced, for example, by the reaction of a compound represented by Formula (3-a):

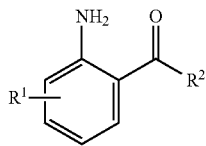

(wherein $R^1$ and $R^2$ have the same meanings as defined above), or a salt thereof, a compound represented by Formula (3-b):

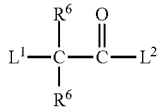

(wherein $R^6$ has the same meaning as defined above; and $L^1$ and $L^2$ independently denote a leaving group), or a salt thereof, and a compound represented by Formula (3-c):

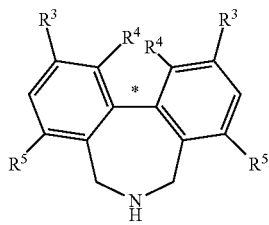

(wherein $R^3$, $R^4$, $R^5$, and * have the same meanings as defined above), or a salt thereof.

In the production method of the compound represented by the above Formula (3), the reaction of the compound represented by Formula (3-a), the compound represented by Formula (3-b), and the compound represented by Formula (3-c) may be conducted in accordance with a known method, a method known per se, or a method equivalent thereto. The compound represented by Formula (3) may be produced, for example, by the reaction of the compound represented by Formula (3-a) and the compound represented by Formula (3-b) and the further reaction of the obtained reaction product and the compound represented by Formula (3-c).

The compound represented by Formula (3-a) or a salt thereof may be produced by a known method or be a commercial product.

The compound represented by Formula (3-a) or a salt thereof is preferably a compound represented by Formula (3-a-1):

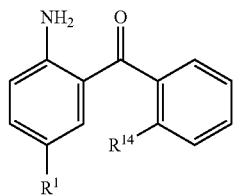

(wherein $R^1$ has the same meaning as defined above; and $R^{14}$ denotes a hydrogen atom or a halogen atom).

In the compound represented by Formula (3-a-1) or a salt thereof, examples of $R^1$ include those listed for Formula (3), for example. Examples of the halogen include those listed for Formula (3), for example.

In the compound represented by Formula (3-b):

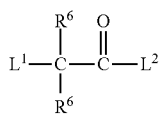

or a salt thereof, $L^1$ and $L^2$ independently denote a leaving group; and $R^6$ has the same meaning as defined above. The leaving group is not particularly limited as long as it is a generally known leaving group, and examples thereof include a halogen atom, a tosylate (OTs), and a mesylate (OMs).

$L^1$ and $L^2$ are preferably the same group as each other, and more preferably each a halogen atom. The halogen atom is more preferably a chlorine atom or a bromine atom.

Examples of the compound represented by Formula (3-b) include $ClCH_2COCl$ and $BrCH_2COBr$.

The compound represented by Formula (3-b) or a salt thereof can be produced by a known method. As an acetanilide compound derived from the compound represented by Formula (3-b), substances described in a document (T. K. Ellis et al., J. Org. Chem., 2006, 71, 8572-8578.), for example, can be used.

Next, the compound represented by the above Formula (3-c) will be described. The compound represented by Formula (3-c) is preferably a compound represented by Formula (3-c-1):

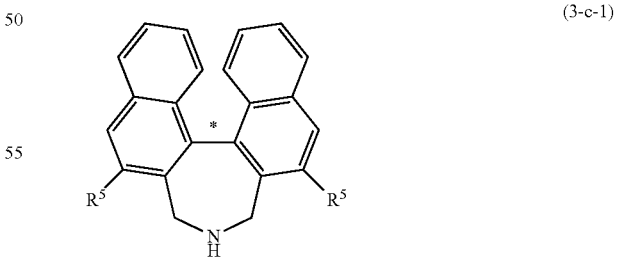

(wherein $R^5$ and * have the same meanings as defined above). As the compound represented by Formula (3-c-1), substances described in a document (N. Maigrot et al., J. Org. Chem., 1985, 50, 3916-3918.), for example, can be used.

Next, a description will be given for the conditions for the reaction of the compound represented by Formula (3-a), the compound represented by Formula (3-b), and the compound represented by Formula (3-c) in the production of the compound represented by the above Formula (3).

The amount of the compound represented by Formula (3-b) or a salt thereof used is not particularly limited as long as the reaction proceeds. Specifically, the amount may usually be about 0.5 to 10 mol, and is preferably about 1.0 to 3.0 mol, relative to 1 mol of the compound represented by Formula (3-a) or a salt thereof.

The amount of the compound represented by Formula (3-c) or a salt thereof used is not particularly limited as long as the reaction proceeds. Specifically, the amount may usually be about 0.5 to 5.0 mol, and is preferably about 0.5 to 2.0 mol, relative to 1 mol of the compound represented by Formula (3-a) or a salt thereof.

In the above production method of the compound represented by Formula (3) or a salt thereof, the solvent used for the reaction is not particularly limited, and examples thereof include organic solvents, such as alcohols (methanol, ethanol, isopropanol, tert-butanol, etc.); ethers (diethyl ether, tetrahydrofuran (THF), 1,4-dioxane, 1,2-dimethoxyethane, etc.); halogenated hydrocarbons (dichloromethane, chloroform, 1,2-dichloroethane, carbon tetrachloride, etc.); aromatic hydrocarbons (benzene, toluene, xylene, pyridine, etc.); aliphatic hydrocarbons (hexane, pentane, cyclohexane, etc.); nitriles (acetonitrile, propionitrile, etc.); and amides (N,N-dimethylformamide (DMF), N,N-dimethylacetamide (DMA), N-methylpyrrolidone, etc.). Among these, from the viewpoint of reaction efficiency, more preferred are nitriles, such as acetonitrile and propionitrile, and amides, such as N,N-dimethylformamide (DMF), N,N-dimethylacetamide (DMA), and N-methylpyrrolidone.

In the above production method of the compound represented by Formula (3) or a salt thereof, the base used for the reaction is not particularly limited, and examples thereof include potassium hydroxide, sodium hydroxide, lithium hydroxide, sodium hydrogen carbonate, potassium carbonate, sodium carbonate, cesium carbonate, sodium acetate, potassium acetate, lithium acetate, rubidium nitrate, lithium nitrate, rubidium nitrite, sodium sulfite, sodium cyanate, lithium cyanate, sodium thiocyanate, potassium thiocyanate, sodium stearate, cesium stearate, sodium borohydride, potassium borohydride, lithium borohydride, sodium tetraphenylborate, sodium benzoate, and lithium benzoate. Among these, from the viewpoint of reaction efficiency, preferred are potassium hydroxide, sodium hydroxide, lithium hydroxide, potassium carbonate, sodium carbonate, cesium carbonate, and the like.

In the above production method of the compound represented by Formula (3) or a salt thereof, an additional step of separation and/or purification may be performed to obtain an optically pure objective substance. The separation and/or purification method is not particularly limited, and various methods usually used in this field may be used. Specific examples of the separation method include concentration, extraction, filtration, and washing, and specific examples of the purification method include crystallization (recrystallization, suspension, etc.), selective dissolution, and physical optical resolution using a column for optical isomer separation, etc. In the recrystallization, formation of a salt with an achiral acid (hydrochloric acid, sulfuric acid, methanesulfonic acid, formic acid, trifluoroacetic acid, etc.) may be performed, or the diastereomeric salt formation method using a chiral acid (mandelic acid, tartaric acid, dibenzoyltartaric acid, ditoluoyltartaric acid, camphor-10-sulfonic acid, malic acid) may be employed.

More specific reaction conditions in the production of the compound represented by Formula (3) or a salt thereof may be determined by reference to examples described below.

In a preferred aspect of the present invention, the metal complex represented by Formula (1):

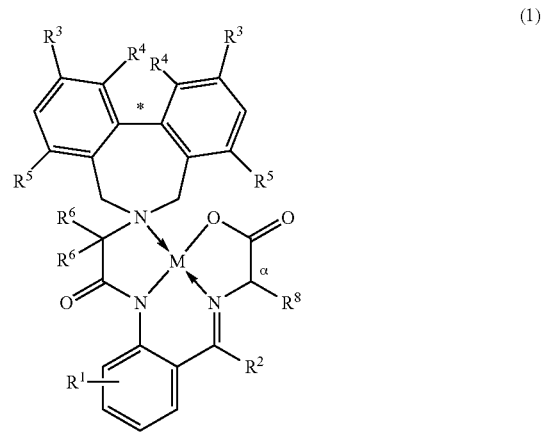

(1)

(wherein $R^1$, $R^2$, $R^3$, $R^4$, $R^5$, $R^6$, and * have the same meanings as defined above;

$R^8$ denotes hydrogen, an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group;

M denotes a divalent metallic cation; and specific examples of $R^1$ to $R^6$ include those listed for Formula (3), for example)

is produced using the compound represented by the above Formula (3).

In the metal complex represented by Formula (1), the divalent metallic cation denoted by M is not particularly limited, and examples thereof include cations of alkaline earth metals, such as magnesium, calcium, strontium, and barium; and cations of transition metals, such as cadmium, titanium, zirconium, nickel (II), palladium, platinum, zinc, copper (II), mercury (II), iron (II), cobalt (II), tin (II), lead (II), and manganese (II). Among them, preferred is a cation of nickel, copper, palladium, or platinum.

The metal complex represented by Formula (1) has axial chirality as indicated by * in the biphenyl moiety.

The metal complex represented by Formula (1) is preferably a metal complex represented by Formula (1) wherein $R^3$ and $R^4$ in each pair form an aromatic or aliphatic cyclic structure together with the carbon atoms to which they are bonded, namely represented by Formula (1a):

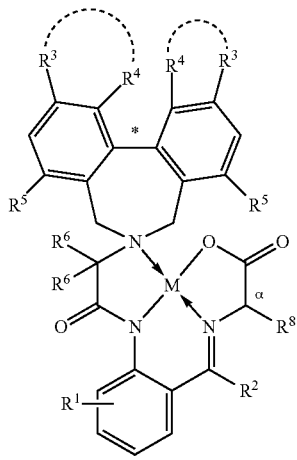

(1a)

(wherein $R^1$, $R^2$, $R^5$, $R^6$, $R^8$, *, and M have the same meanings as defined above).

The metal complex represented by the above Formula (1a) is preferably a metal complex represented by Formula (1a) wherein $R^5$ and $R^6$ are each hydrogen; and M denotes a nickel cation, a copper cation, a palladium cation, or a platinum cation, namely represented by Formula (1b):

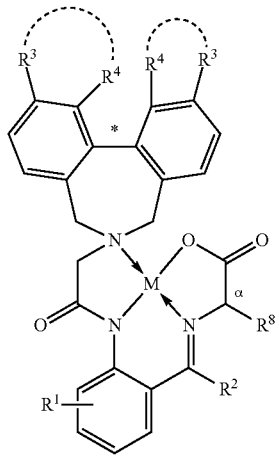

(1b)

(wherein $R^1$, $R^2$, $R^3$, $R^4$, $R^8$, and * have the same meanings as defined in Formula (1a); and M denotes a nickel cation, a copper cation, a palladium cation, or a platinum cation).

The metal complex represented by the above Formula (1) include a metal complex represented by Formula (1-1):

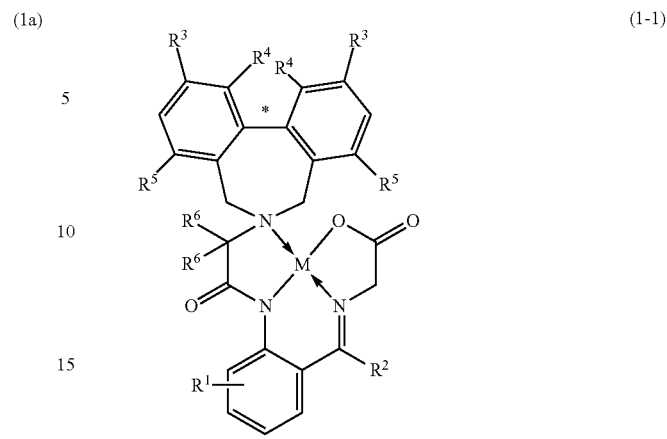

(1-1)

(wherein $R^1$, $R^2$, $R^3$, $R^4$, $R^5$, $R^6$, *, and M have the same meanings as defined above),
and a metal complex represented by Formula (1-1'):

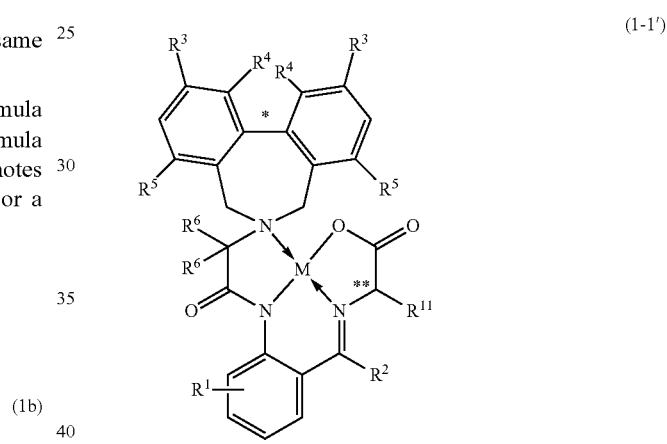

(1-1')

(wherein $R^1$, $R^2$, $R^3$, $R^4$, $R^5$, $R^6$, *, and M have the same meanings as defined above;
$R^{11}$ may have the same meaning as the above $R^8$, but is not a hydrogen atom; and
** denotes an asymmetric carbon atom).

In a particularly preferred aspect of the present invention, the metal complex represented by the above Formula (1-1) or the metal complex represented by the above Formula (1-1') is the one
wherein $R^1$ is hydrogen, chlorine, a methyl group, or a nitro group;
in each of the two pairs of $R^3$ and $R^4$, $R^3$ and $R^4$ form an aromatic or aliphatic cyclic structure together with the aromatic-ring carbon atoms to which they are bonded;
$R^5$ and $R^6$ are each hydrogen; and
$R^2$ is an aryl group represented by Formula (1-1a):

(1-1a)

(wherein $R^{14}$ denotes a hydrogen atom or a halogen atom).

Next, a production method of the metal complex represented by the above Formula (1-1) will be described. This step corresponds to the step [A-1] of the above whole scheme.

By the reaction of the compound represented by Formula (3):

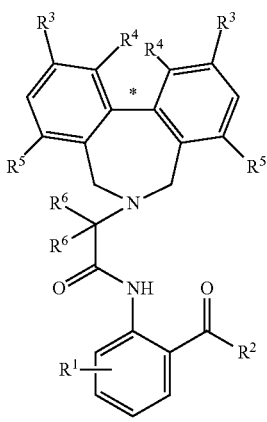
(3)

(wherein $R^1$, $R^2$, $R^3$, $R^4$, $R^5$, $R^6$, and * have the same meanings as defined above),
glycine represented by Formula (4):

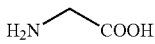
(4)

or a salt thereof, and the metal compound represented by Formula (9):

$$MXn \quad (9)$$

(wherein M denotes a divalent metallic cation; and
X denotes a univalent or divalent anion, when X is a univalent anion, n is 2, and when X is a divalent anion, n is 1),
in the presence of a base, the metal complex represented by Formula (1-1) can be obtained.

In the production method of the metal complex represented by Formula (1-1), as the solvent used for the reaction, preferred are alcohols (methanol, ethanol, isopropanol, tert-butanol, isobutanol, etc.). The amount of the solvent used is not particularly limited as long as the reaction proceeds. The amount may usually be about 1.0 to 150 parts by volume, and, from the viewpoint of production efficiency, is preferably about 5 to 50 parts by volume, relative to 1 part by weight of the compound represented by Formula (3) or a salt thereof.

The amount of the glycine represented by Formula (4) or a salt thereof used is not particularly limited. The amount may usually be about 0.1 to 10 mol, and, from the viewpoint of reaction efficiency, is preferably about 0.3 to 5 mol, relative to 1 mol of the compound represented by Formula (3) or a salt thereof.

The amount of the metal compound represented by Formula (9) used is not particularly limited. For example, the amount may usually be about 0.1 to 10 mol, and, from the viewpoint of reaction efficiency, is preferably about 0.5 to 8.0 mol, relative to 1 mol of the compound represented by Formula (3) or a salt thereof.

In the production method of the metal complex represented by Formula (1-1), the base used is not particularly limited, and for example, may be the same as used in the production method of the compound represented by Formula (3) or a salt thereof. Among the usable bases, from the viewpoint of reaction efficiency, preferred are potassium carbonate, sodium carbonate, cesium carbonate, potassium hydroxide, sodium hydroxide, and lithium hydroxide.

The amount of the base used is not particularly limited. The amount may usually be about 0.1 to 20 mol, and, from the viewpoint of reaction efficiency, is preferably 0.5 to 10 mol, relative to 1 mol of the compound represented by Formula (3).

In the above production method, the reaction time is not particularly limited as long as the reaction sufficiently proceeds. The time may usually be 0.1 to 72 hours, and, from the viewpoint of production efficiency, is preferably 0.1 to 48 hours, and particularly preferably 0.1 to 20 hours.

The pressure for the reaction is not particularly limited, and the reaction may be performed under any condition of atmospheric pressure, increased pressure, and reduced pressure. Specifically, the pressure may usually be about 0.1 to 10 atmospheres.

The reaction temperature for the reaction is not particularly limited as long as the reaction proceeds. For example, the temperature may usually be 0 to 100° C., and, from the viewpoint of reaction efficiency, is preferably 0 to 80° C., and more preferably 5 to 60° C.

The thus-obtained metal complex represented by Formula (1-1) can be used for the following step (that is, the step [A-2] shown in the whole scheme).

Next, a production method of the metal complex represented by the above Formula (1-1') will be described. This step corresponds to the step shown in [C-1] of the above whole scheme.

By the reaction of the compound represented by Formula (3):

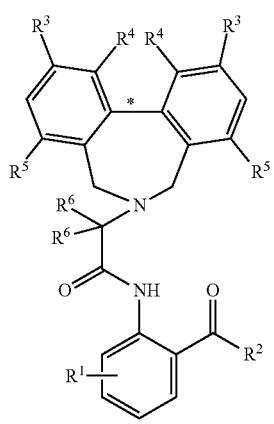
(3)

(wherein $R^1$, $R^2$, $R^3$, $R^4$, $R^5$, $R^6$, and * have the same meanings as defined above),
the optically active α-amino acid represented by Formula (5):

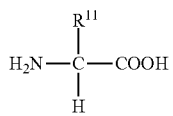
(5)

(wherein $R^{11}$ has the same meaning as defined in the above Formula (1-1')), (or an enantiomeric mixture thereof at any ratio) or a salt thereof, and the metal compound represented by Formula (9):

MX$n$ (9)

(wherein M, X, and n have the same meanings as defined above), in the presence of a base, the metal complex represented by Formula (1-1') can be obtained.

Examples of the optically active α-amino acid represented by the above Formula (5) or a salt thereof include α-amino acids, such as alanine (Ala), arginine (Arg), asparagine (Asn), aspartic acid (Asp), cysteine (Cys), glutamine (Gln), glutamic acid (Glu), histidine (His), isoleucine (Ile), leucine (Leu), lysine (Lys), methionine (Met), phenylalanine (Phe), serine (Ser), threonine (Thr), tryptophan (Trp), tyrosine (Tyr), and valine (Val) and salts thereof, and also include unnatural optically active α-amino acids and salts thereof. These α-amino acids or salts thereof may be L-form, D-form, or an enantiomeric mixture thereof at any ratio.

In the production method of the metal complex represented by Formula (1-1'), the kind and amount of the solvent used, the amount of the α-amino acid represented by the above Formula (5) or a salt thereof used, the amount of the metal compound represented by the above Formula (9) used, the kind and amount of the base used, the reaction time, the pressure for the reaction, and the reaction temperature may be the same as those in the production method of the metal complex represented by the above Formula (1-1).

The thus-obtained metal complex represented by Formula (1-1'):

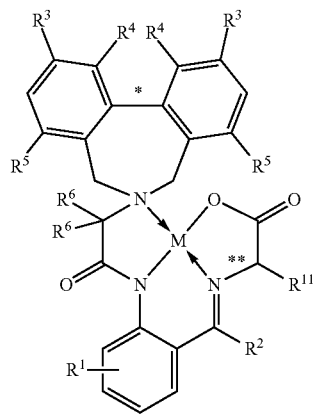

(1-1')

(wherein $R^1$, $R^2$, $R^3$, $R^4$, $R^5$, $R^6$, $R^{11}$, *, M, and ** have the same meanings as defined above)

has an asymmetric carbon atom (the α carbon atom indicated by ** in the α-amino acid moiety).

Next, as one aspect of the present invention, a method for producing an optically active α-amino acid in high yield and in a highly enantioselective manner, using the metal complex represented by Formula (1-1) will be described specifically. This step corresponds to the step [A-2] and the step [A-3] of the above whole scheme.

First, the step [A-2] will be described.

In this step, a side chain is introduced into the α carbon in the α-amino acid moiety of the metal complex represented by Formula (1-1) to give the metal complex represented by Formula (1-2):

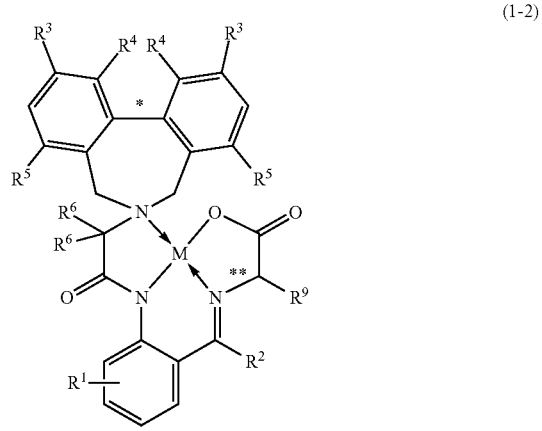

(1-2)

(wherein $R^1$, $R^2$, $R^3$, $R^4$, $R^5$, $R^6$, *, M, and ** have the same meanings as defined in the above Formula (1-1'); and $R^9$ denotes an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, or an optionally substituted aryloxycarbonyl group).

Examples of the optionally substituted alkyl group, the optionally substituted alkynyl group, the optionally substituted alkenyl group, the optionally substituted cycloalkyl group, the optionally substituted aryl group, or the optionally substituted heteroaryl group, denoted by $R^9$ include those listed for $R^1$, for example. Examples of the substituent in this case include those listed for $R^1$, for example.

Examples of the optionally substituted aralkyl group denoted by $R^9$ include an optionally substituted benzyl group, an optionally substituted phenethy group, an optionally substituted phenylpropyl group, an optionally substituted naphthylmethyl group, and an optionally substituted naphthylethyl group. Examples of the substituent in this case include those listed for $R^1$, for example.

Examples of the optionally substituted heteroarylalkyl group denoted by $R^9$ include a group composed of an optionally substituted heteroaryl group and an optionally substituted alkyl group. Examples of the optionally substituted heteroaryl group and the optionally substituted alkyl group include those listed for $R^1$, for example. Examples of the substituent in this case include those listed for $R^1$, for example.

Examples of the optionally substituted alkoxycarbonyl group denoted by $R^9$ include a group composed of a carbonyl group and an optionally substituted alkoxy group. Examples of the optionally substituted alkoxy group include a group composed of an optionally substituted alkyl group and an oxygen atom, such as a methoxy group, an ethoxy group, a propoxy group, an isopropoxy group, a butoxy group, an isobutoxy group, a tert-butoxy group, a pentyloxy group, a decyloxy group, a cyclopentyloxy group, a cyclohexyloxy group, a menthyloxy group, a chloromethoxy group, a fluoromethoxy group, a trifluoromethoxy group, a methoxymethoxy group, an ethoxymethoxy group, a methoxyethoxy group, a benzyloxy group, a 4-chlorobenzyloxy group, a 4-methylbenzyloxy group, a 4-methoxybenzyloxy group, and a 3-phenoxybenzyloxy group. Examples of the optionally substituted alkyl group include those listed for $R^1$, for example. Examples of the substituent in this case include those listed for $R^1$, for example.

Examples of the optionally substituted aryloxycarbonyl group denoted by $R^9$ include a group composed of a carbonyl group and an optionally substituted aryloxy group, such as a phenoxycarbonyl group, a 2-methylphenoxycarbonyl group, a 4-methylphenoxycarbonyl group, a 4-methoxyphenoxycarbonyl group, and a naphthyloxycarbonyl group. Examples of the optionally substituted aryloxy group include a group composed of an optionally substituted aryl group and an oxygen atom, such as a phenoxy group, a 2-methylphenoxy group, a 4-chlorophenoxy group, a 4-methylphenoxy group, a 4-methoxyphenoxy group, and a 3-phenoxyphenoxy group. Examples of the optionally substituted aryl group include those listed for $R^1$, for example. Examples of the substituent in this case include those listed for $R^1$, for example.

The method for introducing a side chain into the α carbon is not particularly limited, and for example, a reaction with an electrophile, such as an alkylation reaction, an aldol reaction, the Michael reaction, and the Mannich reaction may be used. An alkylation reaction, an aldol reaction, the Michael reaction, and the Mannich reaction may be conducted in accordance with a known method, a method known per se, or a method equivalent thereto.

The alkylation reaction will be described.

The alkylation reaction in the step [A-2] is for introducing an alkyl group into the α carbon in the α-amino acid moiety of the metal complex represented by Formula (1-1) by the reaction of the metal complex represented by Formula (1-1) and an alkylating agent (an electrophile) in the presence of a base.

Examples of the alkylating agent include alkyl halide, sulfate ester, aromatic sulfonic acid ester, oxalate ester, carboxylic acid ester, phosphoric acid ester, orthoester, dimethylformamide acetal, trifluoromethanesulfonate ester, alkylammonium salts, alkyldiazonium, alkyl oxonium salts, alkylsulfonium salts, alkyliodonium salts, fluorosulfuric acid ester, dialkyl carbonate, chloroformate ester, and cyanoformate ester (such as Mander's reagent). Among these, alkyl halide and cyanoformate ester are particularly preferably used.

The base is not particularly limited as long as the reaction proceeds. Examples of the base include alkali metal alkoxides, such as sodium methoxide, and alkali metal amides, such as sodium amide. From the viewpoint of the basic strength in the reaction solvent used, preferred is sodium methoxide. The amount of the base added is not particularly limited. The amount is usually 1 to 20 mol, and from the viewpoint of reaction efficiency, preferably 1.5 to 5 mol, relative to 1 mol of the metal complex represented by Formula (1-1).

The solvent used for the alkylation reaction is not particularly limited, and examples thereof include acetone, toluene, benzene, dimethyl sulfoxide (DMSO), N,N-dimethylformamide (DMF), N,N-dimethylacetamide (DMA), dimethoxyethane (DME), diethyl ether, tetrahydrofuran (THF), dioxane, acetonitrile, and dichloromethane.

The reaction temperature is not particularly limited as long as the reaction proceeds. For example, the temperature is usually −20 to 25° C., and from the viewpoint of reaction efficiency, preferably −10 to 10° C., and more preferably −5 to 5° C.

The reaction time is not particularly limited as long as the reaction proceeds. For example, the time is usually 0.1 to 30 hours, and from the viewpoint of reaction efficiency, preferably 0.1 to 24 hours.

The amount of the alkylating agent used for the alkylation reaction in the present invention is not particularly limited as long as the reaction proceeds. For example, the amount may usually be 0.5 to 5 mol, and, from the viewpoint of reaction efficiency, is preferably 1 to 5 mol, relative to 1 mol of the metal complex represented by Formula (1-1).

The alkylation reaction proceeds in high yield and in a highly enantioselective manner, in accordance with the configuration of the chiral axis of the metal complex represented by Formula (1-1). That is, in the case where the configuration of the chiral axis of the metal complex represented by Formula (1-1) is S-configuration, the configuration of the α-amino acid moiety will be D-form when a side chain is introduced by an alkylation reaction. In the case where the configuration of the chiral axis of the metal complex represented by Formula (1-1) is R-configuration, the configuration of the α-amino acid moiety will be L-form.

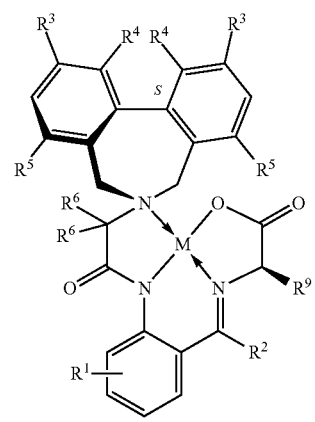

1-2-S-isomer Alkylation product

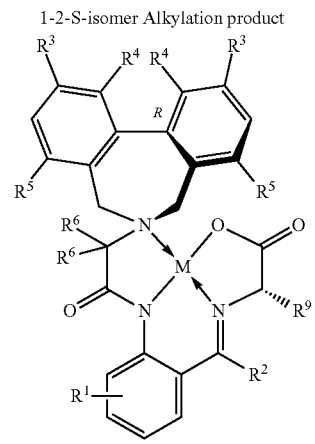

1-2-R-isomer Alkylation product (In the formulae, $R^1$, $R^2$, $R^3$, $R^4$, $R^5$, $R^6$, and M have the same meanings as defined in Formula (1-1);

S or R in italics denotes the configuration of a chiral axis; and $R^9$ has the same meaning as defined above.)

The aldol reaction will be described.

The aldol reaction in the step [A-2] is for introducing a side chain having a hydroxyl group on the β carbon by the reaction of the metal complex represented by Formula (1-1) and an aromatic aldehyde or an aliphatic aldehyde (an electrophile). In the present invention, the aromatic aldehyde and the aliphatic aldehyde are not particularly limited, and examples thereof include a compound in which an aldehyde group is bonded to $R^{15}$ described below.

Both an acid catalyst and a base catalyst can be used for the aldol reaction. From the viewpoint of reaction efficiency, a base catalyst is preferred. The base catalyst is not particularly limited, and examples thereof include diazabicycloundecene (DBU), diazabicyclononene (DBN), triazabicyclodecene (TBD), diazabicyclo[2.2.2]octane (DABCO), triethylamine, diisopropylethylamine, pyridine, 4-dimethylaminopyridine, alkali metal alkoxides, such as sodium methoxide, potassium tert-butoxide, sodium hydride, butyllithium, lithium diisopropylamide, and lithium hexamethyldisilazide. Among these, preferred are diazabicycloundecene (DBU), diazabicyclononene (DBN), and the like. The amount of the catalyst added is not particularly limited as long as the reaction proceeds. The amount is usually 1 to 6 mol, and from the viewpoint of reaction efficiency, preferably 2 to 5 mol, and more preferably 3 mol, relative to 1 mol of the compound represented by Formula (1-1) used as the substrate.

The solvent used for the aldol reaction is not particularly limited, and examples thereof include alcohols, such as methanol, ethanol, isopropanol, and tert-butanol, dimethyl sulfoxide (DMSO), N,N-dimethylformamide (DMF), N,N-dimethylacetamide (DMA), tetrahydrofuran (THF), dioxane, acetonitrile, and dichloromethane.

The reaction temperature is not particularly limited, and is usually −40 to 40° C., and from the viewpoint of reaction efficiency, preferably −20 to 20° C., and more preferably −10 to 0° C.

The reaction time is not particularly limited. The time may usually be 0.1 to 30 hours, and, from the viewpoint of reaction efficiency, is preferably 0.1 to 2 hours.

The amount of the aromatic aldehyde or the aliphatic aldehyde used for the reaction is not particularly limited as long as the reaction proceeds. For example, the amount is usually 0.5 to 10 mol, and from the viewpoint of reaction efficiency, preferably 1 to 8 mol, and more preferably 2 to 7 mol, relative to 1 mol of the metal complex represented by Formula (1-1).

The aldol reaction proceeds in high yield and in a highly enantioselective manner, in accordance with the configuration of the chiral axis of the metal complex represented by Formula (1-1) to give a single stereoisomer in a selective or preferential manner. That is, in the case where the configuration of the chiral axis of the metal complex represented by Formula (1-1) is S-configuration, the configuration of the α carbon in the α-amino acid moiety will be S-configuration and the configuration of the β carbon will be R-configuration when a side chain is introduced by an aldol reaction. In the case where the configuration of the chiral axis of the metal complex represented by Formula (1-1) is R-configuration, the configuration of the α carbon in the α-amino acid moiety will be R-configuration and the configuration of the β carbon will be S-configuration.

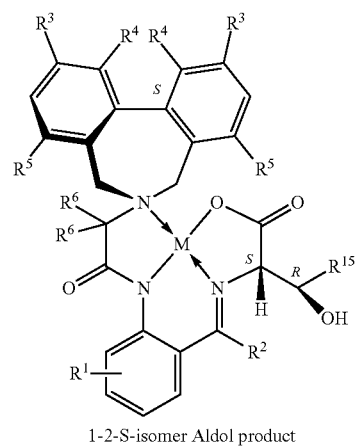

1-2-S-isomer Aldol product

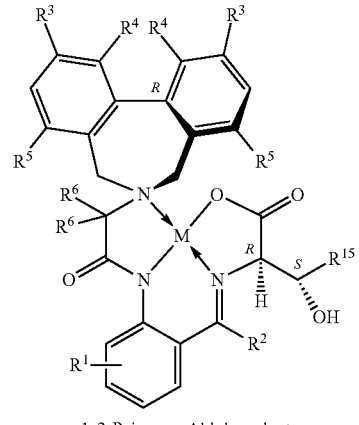

1-2-R-isomer Aldol product (In the formulae, $R^1$, $R^2$, $R^3$, $R^4$, $R^5$, $R^6$, and M have the same meanings as defined in Formula (1-1);

S or R in italics denotes the configuration; and $R^{15}$ denotes an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group.)

Examples of the optionally substituted alkyl group, the optionally substituted alkynyl group, the optionally substituted alkenyl group, the optionally substituted cycloalkyl group, the optionally substituted aryl group, the optionally substituted heteroaryl group, the optionally substituted aralkyl group, or the optionally substituted heteroarylalkyl group, denoted by $R^{15}$ include those listed for $R^9$, for example. Examples of the substituent in this case include those listed for $R^1$, for example.

The Michael reaction will be described.

The Michael reaction in the step [A-2] is for introducing a side chain into the α carbon in the α-amino acid moiety by the reaction of the metal complex represented by Formula (1-1) and any of various Michael reaction acceptors in the presence of a base.

The base used for the reaction is not particularly limited, and examples thereof include sodium hydroxide, lithium hydroxide, sodium hydrogen carbonate, sodium carbonate, potassium carbonate, cesium carbonate, sodium acetate, potassium acetate, lithium acetate, rubidium nitrate, lithium nitrate, rubidium nitrite, sodium sulfite, sodium cyanate, lithium cyanate, sodium thiocyanate, potassium thiocyanate, sodium stearate, cesium stearate, sodium hydride, potassium hydride, lithium hydride, sodium tetraphenylborate, sodium benzoate, lithium benzoate, and alkali metal alkoxides, such as sodium methoxide. Among these, from the viewpoint of reaction efficiency, preferred are potassium hydroxide, sodium hydroxide, lithium hydroxide, potassium carbonate, sodium carbonate, cesium carbonate, and the like.

The amount of the base added is not particularly limited as long as the reaction proceeds. For example, the amount may usually be 0.05 to 10 mol, and, from the viewpoint of reaction efficiency, is preferably 0.08 to 6 mol, and more preferably 0.10 to 5 mol, relative to 1 mol of the metal complex represented by Formula (1-2).

The solvent used for the reaction is not particularly limited, and for example, aliphatic hydrocarbons, such as pentane, hexane, cyclopentane, and cyclohexane; aromatic hydrocarbons, such as toluene and xylene; halogenated hydrocarbons, such as dichloromethane; ketone-based solvents, such as acetone, methyl ethyl ketone, and cyclohexanone; alcohol-based solvents, such as methanol, ethanol, isopropanol, and tert-butanol; and organic solvents, such as tetrahydrofuran (THF), diethyl ether, dimethoxyethane (DME), dimethyl sulfoxide (DMSO), dimethylformamide (DMF), N,N-dimethylacetamide (DMA), and acetonitrile can be used alone or in combination.

The reaction temperature is not particularly limited as long as the reaction proceeds. For example, the temperature may usually be −40 to 20° C., and, from the viewpoint of reaction efficiency, is preferably −10 to 10° C., and more preferably −5 to 5° C.

The reaction time is not particularly limited as long as the reaction proceeds. For example, the time may usually be 0.1 to 30 hours, and, from the viewpoint of reaction efficiency, is preferably 0.1 to 2 hours.

The Michael reaction proceeds in high yield and in a highly enantioselective manner, in accordance with the configuration of the chiral axis of the metal complex represented by Formula (1-1). That is, in the case where the configuration of the chiral axis of the metal complex represented by Formula (1-1) is S-configuration, the configuration of the α carbon in the α-amino acid moiety will be R-configuration when a side chain is introduced by the Michael reaction. In the case where the configuration of the chiral axis of the metal complex represented by Formula (1-1) is R-configuration, the configuration of the α carbon in the α-amino acid moiety will be S-configuration.

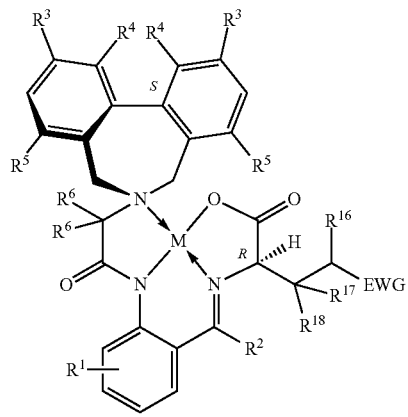

1-1-S-isomer Michael reaction product

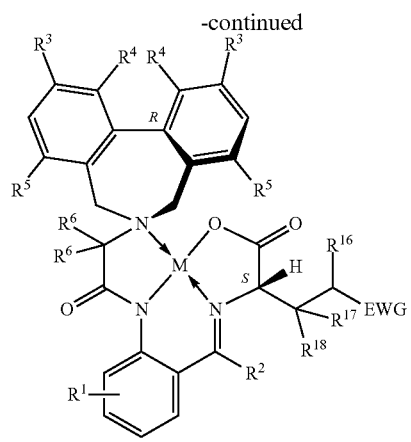

1-1-R-isomer Michael reaction product (In the formulae, $R^1$, $R^2$, $R^3$, $R^4$, $R^5$, $R^6$, and M have the same meanings as defined in Formula (1-1);

S or R in italics denotes the configuration;

$R^{16}$, $R^{17}$, and $R^{18}$ each independently denote an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, or a halogen atom;

$R^{17}$ and $R^{18}$ may form a ring together with the carbon atom to which they are bonded; and EWG denotes an electron withdrawing group.)

Examples of the optionally substituted alkyl group, the optionally substituted alkynyl group, the optionally substituted alkenyl group, the optionally substituted cycloalkyl group, the optionally substituted aryl group, the optionally substituted heteroaryl group, the optionally substituted aralkyl group, or the optionally substituted heteroarylalkyl group, denoted by $R^{16}$, $R^{17}$, and $R^{16}$ include those listed for $R^9$, for example. Examples of the substituent in this case include those listed for $R^1$, for example.

Examples of the electron withdrawing group include a nitro group (—$NO_2$); a cyano group (—CN); organic sulfonyl groups, such as a tosyl group (-Ts) and a mesyl group (-Ms); a sulfamoyl group (—$SO_2NH_2$); and carbonyl groups, such as an alkoxycarbonyl group, an aryloxycarbonyl group, an acyl group, and a carbamoyl group (—$CONH_2$).

The Mannich reaction in the step [A-2] is for introducing a side chain having an amino group into the β carbon by the reaction of the metal complex represented by Formula (1-1) and an imine or an iminium ion which is generated from a primary amine or a secondary amine and an aldehyde.

In the reaction, a catalyst is preferably used. The catalyst used for the reaction is not particularly limited, and catalysts usually used in this field may be used. Examples of the catalyst include diazabicycloundecene (DBU), diazabicyclononene (DBN), triazabicyclodecene (TBD), diazabicyclo[2.2.2]octane (DABCO), L-proline, and a pyrrolidine derivative.

The reaction is usually performed using a solvent. The solvent used for the reaction is not particularly limited, and solvents usually used in this field may be used. An organic solvent, such as tetrahydrofuran (THF), dioxane, dimethyl sulfoxide (DMSO), and acetonitrile; water; or a mixed solvent of water and an organic solvent at any ratio can be used.

The reaction temperature in this reaction is not particularly limited as long as the reaction proceeds. For example, the temperature is usually −20 to 20° C., and from the viewpoint of reaction efficiency, preferably −10 to 10° C., and more preferably −5 to 5° C.

All the reactions in the step [A-2] described above proceed in high yield and in a highly enantioselective manner, and optionally, a step for enhancing the optical purity of the α carbon in the α-amino acid moiety may be performed after the reaction in the step [A-2]. The method for enhancing the optical purity is not particularly limited, and for example, known methods such as crystallization (recrystallization, suspension, etc.), selective dissolution, and physical optical resolution using a column for optical isomer separation, etc. may be used.

In a preferred aspect of the present invention, the method for enhancing the optical purity is a method in which the metal complex obtained in the step [A-2] in an alcoholic solvent, such as methanol, ethanol, isopropanol, tert-butanol, and isobutanol is heated in the presence of a base, such as potassium carbonate, sodium carbonate, cesium carbonate, potassium hydroxide, sodium hydroxide, and lithium hydroxide, usually at a temperature of 40 to 80° C. for 0.5 to 24 hours. The configuration of the α carbon in the α-amino acid moiety is converted by heating, in accordance with the configuration of the chiral axis of the metal complex, and therefore, the optical purity of the compound is enhanced.

Next, the acid decomposition in the step [A-3] of the whole scheme will be described.

The α-amino acid moiety of the metal complex represented by Formula (1-2) can be released by acid decomposition of the metal complex.

The acid used for the acid decomposition is not particularly limited as long as it is a known acid, and may be an inorganic acid or an organic acid. Examples of the inorganic acid include hydrochloric acid, nitric acid, sulfuric acid, and perchloric acid. Examples of the organic acid include acetic acid, trifluoroacetic acid, methanesulfonic acid, trifluoromethanesulfonic acid, oxalic acid, propionic acid, butyric acid, and valeric acid. Among these, for efficient decomposition, preferred are hydrochloric acid, sulfuric acid, trifluoroacetic acid, and methanesulfonic acid, and more preferred are hydrochloric acid and methanesulfonic acid.

The amount of the acid used is not particularly limited as long as acid decomposition sufficiently proceeds. For example, the amount may usually be about 0.1 to 20 mol, and, from the viewpoint of decomposition efficiency, is preferably about 0.3 to 10 mol, relative to 1 mol of the metal complex.

The solvent used is preferably an alcohol (methanol, ethanol, isopropanol, tert-butanol, or the like) and methanol or ethanol is preferably used. The amount of the solvent used is not particularly limited. For example, the amount may usually be about 0.1 to 100 parts by volume, and is preferably about 0.5 to 50 parts by volume, relative to 1 part by weight of the metal complex. Alternatively, the amount of the solvent used may also usually be about 0.05 to 100 parts by weight, and is preferably about 0.1 to 50 parts by weight, relative to 1 part by weight of the metal complex.

The reaction temperature in the acid decomposition is not particularly limited as long as the compound can be decomposed without degradation thereof. The temperature may usually be about 0 to 100° C., and, from the viewpoint of decomposition efficiency, is preferably about 0 to 80° C., more preferably about 5 to 60° C., and particular preferably about 40 to 60° C.

The reaction time in the acid decomposition is not particularly limited as long as the decomposition sufficiently proceeds. The time may usually be about 0.1 to 72 hours, and, from the viewpoint of decomposition efficiency, is preferably about 0.1 to 48 hours, and particularly preferably about 0.1 to 20 hours.

The pressure is not particularly limited unless the reaction is inhibited, and may be about 0.1 to 10 atmospheres, for example.

By the step [A-3], an optically active mono-substituted α-amino acid represented by the following Formula (6):

(6)

(wherein $R^9$ denotes an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, or an optionally substituted aryloxycarbonyl group; and ** denotes an asymmetric carbon atom), or a salt thereof is released.

The configuration of the asymmetric carbon atom (α carbon) in the above Formula (6) depends on the configuration of the chiral axis of the metal complex of Formula (1-1) used for the introduction of a side chain in the step [A-2]. Specifically, when the configuration of the chiral axis in Formula (1-1) is S-configuration, the configuration of the optically active α-amino acid of Formula (6) obtained by the alkylation reaction is D-form:

(6-1)

(wherein $R^9$ has the same meaning as defined in the above Formula (6)),
and when the configuration of the chiral axis in Formula (1-1) is R-configuration, the configuration of the optically active α-amino acid is L-form:

(6-2)

(wherein $R^9$ has the same meaning as defined in the above Formula (6)).

Also, when the configuration of the chiral axis in Formula (1-1) is S-configuration, the configuration of the α carbon of the optically active α-amino acid of Formula (6) obtained by the aldol reaction is S-configuration:

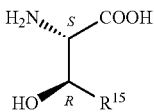

(6-3)

(wherein $R^{15}$ has the same meaning as defined above),
and when the configuration of the chiral axis in Formula (1-1) is R-configuration, the configuration of the α carbon is R-configuration:

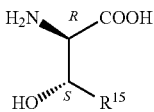

(6-4)

(wherein $R^{15}$ has the same meaning as defined above).

Furthermore, when the configuration of the chiral axis in Formula (1-1) is S-configuration, the configuration of the α carbon of the optically active α-amino acid of Formula (6) obtained by the Michael reaction is R-configuration:

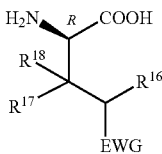

(6-5)

(wherein $R^{16}$, $R^{17}$, $R^{18}$, and EWG have the same meanings as defined above),
and when the configuration of the chiral axis in Formula (1-1) is R-configuration, the configuration of the α carbon is S-configuration:

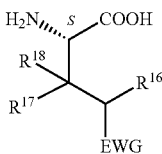

(6-6)

(wherein $R^{16}$, $R^{17}$, $R^{18}$, and EWG have the same meanings as defined above).

The released optically active α-amino acid or a salt thereof may be separated and/or purified by a known method after the acid decomposition. Any known method can be used without particular limitation as long as it can be performed by a person having ordinary skill in the art. A method using an ion-exchange resin may be used, for example.

The thus-obtained optically active α-amino acid or a salt thereof can be easily converted to a derivative having an appropriate protecting group (for example, a Z group, an Fmoc group, a Boc group, or the like).

The compound represented by Formula (3) can be recovered and reused after the acid decomposition in the step [A-3]. This compound can be recovered at a high rate (about 90% or more) and the optical purity is not likely to decrease, enabling an efficient reuse of the compound.

The recovery method is not particularly limited, and various methods usually used in this field may be used. Solvent exchange, concentration, crystallization, or a method using chromatography may be used, for example.

In one aspect of the present invention, another side chain may be introduced into the α carbon in the α-amino acid moiety of the metal complex represented by the above Formula (1-2) to produce the metal complex represented by Formula (2-1):

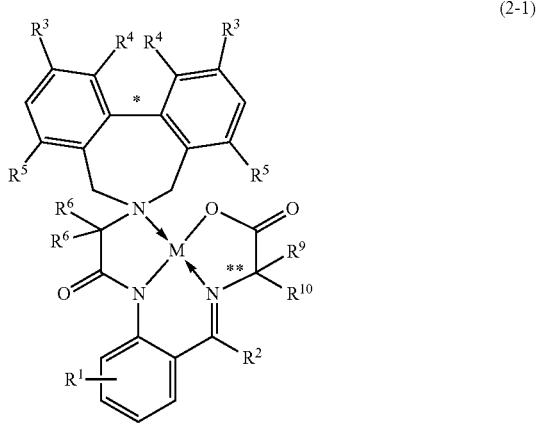

(2-1)

(wherein $R^1$, $R^2$, $R^3$, $R^4$, $R^5$, $R^6$, $R^9$, M, *, and ** have the same meanings as defined above;
$R^{10}$ denotes an optionally substituted alkyl group (for example, an alkyl group in which a part or all of the hydrogen atoms are replaced with a fluorine atom(s)), an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, or an optionally substituted aryloxycarbonyl group; and
$R^9$ and $R^{10}$ may form a ring together with the carbon atom to which they are bonded).

Examples of the optionally substituted alkyl group, the optionally substituted alkynyl group, the optionally substituted alkenyl group, the optionally substituted cycloalkyl group, the optionally substituted aryl group, the optionally substituted heteroaryl group, the optionally substituted aralkyl group, or the optionally substituted heteroarylalkyl group, denoted by $R^{10}$ include those listed for $R^9$, for example. Examples of the substituent in this case include those listed for $R^1$, for example.

The ring formed of $R^9$ and $R^{10}$ together with the carbon atom to which they are bonded is not particularly limited, and examples thereof include cycloalkanes having 3 to 12 carbon atoms and optionally having a substituent. Examples of the cycloalkane having 3 to 12 carbon atoms include cyclopropane, cyclobutane, cyclopentane, cyclohexane, cyclohexene, decalin, oxocyclohexane, dioxocyclohexane, hydroxycyclopentane, and hydroxycyclohexane. Examples of the substituent in this case include those listed for $R^1$, for example.

The method for introducing a side chain into the α carbon is not particularly limited, and a reaction with an electrophile, such as an alkylation reaction, an aldol reaction, the Michael reaction, and the Mannich reaction can be used, for example. The reaction conditions for an alkylation reaction, an aldol reaction, the Michael reaction, or the Mannich reaction may be the same as those in the step [A-2] except that the metal complex represented by Formula (1-2) is substituted for the metal complex represented by the above Formula (1-1). This step corresponds to the step [B-1] of the whole scheme.

One preferred aspect of the metal complex represented by the above Formula (2-1) is the one
wherein $R^1$ is hydrogen, chlorine, a methyl group, or a nitro group;
in each of the two pairs of $R^3$ and $R^4$, $R^3$ and $R^4$ form an aromatic or aliphatic cyclic structure together with the aromatic-ring carbon atoms to which they are bonded;
$R^5$ and $R^6$ are each hydrogen; and
$R^2$ is an aryl group represented by Formula (1-1a):

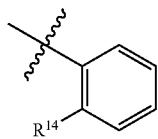

(1-1a)

(wherein $R^{14}$ denotes a hydrogen atom or a halogen atom).

The α-amino acid moiety of the metal complex of Formula (2-1) obtained by the step [B-1] can be released by acid decomposition of the metal complex. As a result, an optically active α,α-disubstituted α-amino acid having a desired chirality can be obtained. The conditions for the acid decomposition may be the same as those in the step [A-3] except that the metal complex represented by Formula (2-1) is substituted for the compound represented by the above Formula (1-2). This step corresponds to the step [B-2] of the whole scheme.

By the step [B-2], an optically active α,α-disubstituted α-amino acid represented by the following Formula (7):

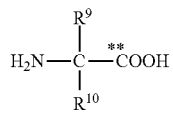

(7)

(wherein $R^9$, $R^{10}$, and ** have the same meanings as defined in the above Formula (2-1)),
or a salt thereof is released.

Whether the α carbon of the obtainable optically active α,α-disubstituted α-amino acid represented by the above Formula (7) or a salt thereof has S-configuration or R-configuration is determined in a preferential or selective manner, in accordance with the configuration of the chiral axis of the metal complex of Formula (1-2):

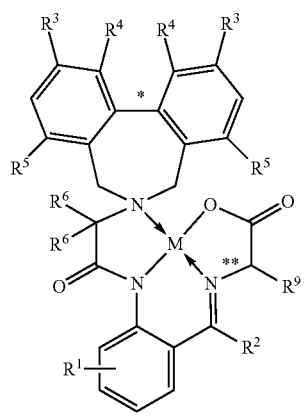

(1-2)

(wherein $R^1$, $R^2$, $R^3$, $R^4$, $R^5$, $R^6$, $R^9$, M, *, and ** have the same meanings as defined above)
generated as an intermediate.

"In a preferential or selective manner" means that the optical purity of the α carbon is about 80% or more. The same shall apply hereinafter.

The optically active α,α-disubstituted α-amino acid or a salt thereof may be separated and/or purified by a known method after the acid decomposition. Any known method can be used without particular limitation as long as it can be performed by a person having ordinary skill in the art. A method using an ion-exchange resin may be used, for example.

The thus-obtained optically active α,α-disubstituted α-amino acid or a salt thereof can be easily converted to a derivative having an appropriate protecting group (for example a Z group, an Fmoc group, a Boc group, or the like).

The compound represented by Formula (3) can be recovered and reused after the acid decomposition in the step [B-2]. The recovery method is not particularly limited, and various methods usually used in this field may be used. Solvent exchange, concentration, crystallization, or a method using chromatography may be used, for example.

In another aspect of the present invention, using the metal complex of Formula (1-1'):

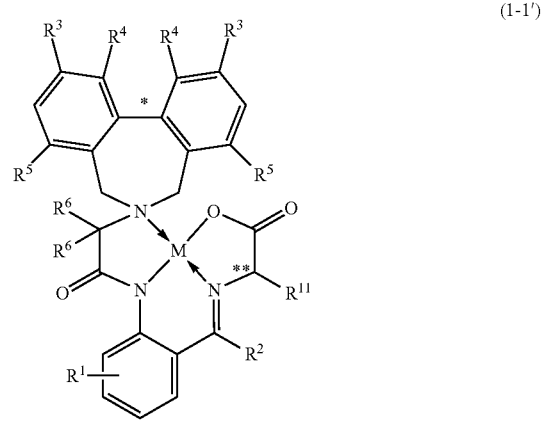

(1-1')

(wherein $R^1$, $R^2$, $R^3$, $R^4$, $R^5$, $R^6$, $R^{11}$, *, M, and ** have the same meanings as defined above)
obtained by the step [C-1], the optically active α-amino acid represented by Formula (8):

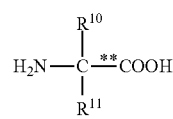

(8)

(wherein $R^{10}$, $R^{11}$, and ** have the same meanings as defined above) may be produced in high yield and in a highly enantioselective manner.

A production method of the optically active α-amino acid represented by Formula (8) will be described specifically below. This step corresponds to the step [C-2] and the step [C-3] of the whole scheme.

In this aspect, a side chain is introduced into the α carbon in the α-amino acid moiety of the metal complex represented by the above Formula (1-1') to give the metal complex represented by Formula (2-1'):

(2-1')

[Chemical structure diagram showing a metal complex with substituents R¹, R², R³, R⁴, R⁵, R⁶, R¹⁰, R¹¹ and metal M]

(wherein $R^1$ to $R^6$, $R^{10}$, $R^{11}$, M, *, and ** have the same meanings as defined above; and $R^{10}$ and $R^{11}$ may form a ring together with the carbon atom to which they are bonded).

In the metal complex represented by Formula (2-1'), examples of the ring formed of $R^{10}$ and $R^{11}$ together with the carbon atom to which they are bonded include those listed for the ring formed of $R^9$ and $R^{10}$ together with the carbon atom to which they are bonded in the metal complex represented by Formula (2-1), for example.

One preferred aspect of the metal complex represented by the above Formula (2-1') is the one
wherein $R^1$ is hydrogen, chlorine, a methyl group, or a nitro group;
in each of the two pairs of $R^3$ and $R^4$, $R^3$ and $R^4$ form an aromatic or aliphatic cyclic structure together with the aromatic-ring carbon atoms to which they are bonded;
$R^5$ and $R^6$ are each hydrogen; and
$R^2$ is an aryl group represented by Formula (1-1a):

(1-1a)

[Chemical structure of aryl group with R¹⁴ substituent]

(wherein $R^{14}$ denotes a hydrogen atom or a halogen atom).

The method for introducing a side chain into the α carbon is not particularly limited, and an alkylation reaction, an aldol reaction, the Michael reaction, the Mannich reaction, and the like can be used. The reaction conditions for an alkylation reaction, an aldol reaction, the Michael reaction, or the Mannich reaction may be the same as those in the step [A-2] except that the metal complex represented by Formula (1-1') is substituted for the metal complex represented by the above Formula (1-1). This step corresponds to the step [C-2] of the whole scheme.

The α-amino acid moiety of the metal complex of Formula (2-1') obtained by the step [C-2] can be released by acid decomposition of the metal complex. As a result, the optically active α-amino acid of the above Formula (8) having a desired chirality or a salt thereof can be obtained. The conditions for the acid decomposition may be the same as those in the step [A-3] except that the metal complex represented by Formula (2-1') is substituted for the compound represented by the above Formula (1-2). This step corresponds to the step [C-3] of the whole scheme.

The configuration of the α carbon of the obtainable optically active Cc-amino acid represented by the above Formula (8) or a salt thereof has either S-configuration or R-configuration in a preferential or selective manner, in accordance with the configuration of the chiral axis of the metal complex represented by Formula (1-1').

The optically active α-amino acid represented by Formula (8) or a salt thereof may be separated and/or purified by a known method after the acid decomposition. Any known method can be used without particular limitation as long as it can be performed by a person having ordinary skill in the art. A method using an ion-exchange resin may be used, for example.

The thus-obtained optically active α-amino acid represented by Formula (8) or a salt thereof can be easily converted to a derivative having an appropriate protecting group (for example, a Z group, an Fmoc group, a Boc group, or the like).

Examples of the salt used herein include salts of inorganic acids, such as hydrochloric acid, hydrobromic acid, sulfuric acid, and phosphoric acid; salts of organic acids, such as acetic acid, trifluoroacetic acid, methanesulfonic acid, and toluenesulfonic acid; salts of inorganic bases, such as sodium hydroxide and potassium hydroxide; and salts of organic bases, such as triethylamine and cyclohexylamine.

In one aspect of the present invention, for example, using the compound represented by Formula (1-2) or the compound represented by Formula (1-1') as an intermediate, a ring may be formed by an alkylation reaction, the Michael reaction, or the like, or alternatively, by an intramolecular condensation reaction, such as an aldol reaction, to give a compound of Formula (2-1) having a ring formed of $R^9$ and $R^{10}$ together with the carbon atom to which they are bonded or a compound of Formula (2-1') having a ring formed of $R^{10}$ and $R^{11}$ together with the carbon atom to which they are bonded. The ring may be formed in accordance with a known method, a method known per se, or a method equivalent thereto which is usually used for cyclization in this field.

EXAMPLE

The present invention will be described more specifically with reference to experimental examples and examples, but the present invention is not limited to these examples at all.

In Examples and Reference Examples, measurements were made under the following HPLC conditions.

<HPLC Conditions-1: Complex Analysis Conditions>

Column: Inertsil ODS-3 (3 μm, 150×4.6 mm i.d.)

Eluent: A:B=40:60 to 20:80 (0 to 25 min) and
20:80 (25 to 45 min)

A=10 mM ammonium formate in 0.1% formic acid buffer solution

B=acetonitrile

Flow rate: 1.0 mL/min

Temperature: 30° C.

Detector: UV 254 nm

Other HPLC analysis conditions for α-amino acids and derivatives thereof are described separately below.

Example 1

Synthesis of Nickel (II) Complex Having Glycine Moiety

Example 1-1: (S)-N-(2-benzoyl-4-chlorophenyl)-2-[3,5-dihydro-4H-dinaphtho[2,1-c:1',2'-e]azepin-4-yl]acetamide [Chiral Auxiliary (S-Isomer)]

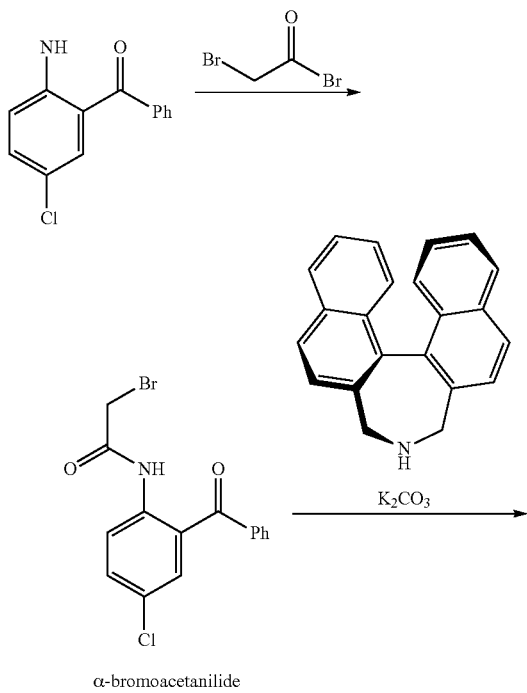

α-bromoacetanilide

To an acetonitrile solution (500 mL) of 2-amino-5-chlorobenzophenon (25.0 g, 107.9 mmol), potassium carbonate (44.7 g, 323.7 mmol) and an acetonitrile solution (50 mL) of bromoacetyl bromide (28.3 g, 140.3 mmol) were added. The mixture was stirred at room temperature for 0.5 hour. After the end of the reaction, the precipitate was filtered off, and the filtrate was concentrated to dryness. To the concentrated residue, water (75 mL) was added, and phase separation was performed with ethyl acetate (200 mL, twice). The organic layer was washed with water (150 mL), dried over sodium sulfate, and then concentrated to 150 mL. To the concentrate, hexane (50 mL) was added, and the mixture was stirred at room temperature for 16 hours and subsequently at 0° C. for 1 hour. The precipitated crystals were separated by filtration, and then dried under vacuum at 30° C. to give N-(2-benzoyl-4-chlorophenyl)-2-bromoacetamide (33.16 g, yield: 87%, chemical purity: 99.2%) as pale white crystals.

$^1$H-NMR (200 MHz, CDCl$_3$): δ 4.02 (2H, s, COCH$_2$), 7.48-7.76 (7H, m, ArH), 8.55-8.60 (1H, m, ArH), 11.32 (1H, br s, NH).

To an acetonitrile solution (60 mL) of N-(2-benzoyl-4-chlorophenyl)-2-bromoacetamide (2.0 g, 5.7 mmol), potassium carbonate (1.18 g, 8.5 mmol) and (S)-binaphthyl amine were added. The mixture was heated to 40° C. and stirred for 16 hours. After the end of the reaction, the reaction suspension was concentrated to dryness. The concentrated residue was purified by silica gel chromatography (hexane:ethyl acetate=4:1 (v/v)) to give (S)-N-(2-benzoyl-4-chlorophenyl)-2-[3,5-dihydro-4H-dinaphtho[2,1-c:1',2'-e]azepin-4-yl]acetamide (3.25 g, yield: quantitative, chemical purity: 99.7%, 99.8% ee) as pale yellow crystals.

ESI-MS (positive mode): m/z=567.2 for [M+H]$^+$.

$^1$H-NMR (200 MHz, CDCl$_3$): δ 3.09 and 3.54 (1H each, ABq, J=16.8 Hz, COCH$_2$), 3.39 and 3.61 (2H each, ABq, J=12.1 Hz, 2×NCH$_2$), 7.21-7.30 (2H, m, ArH), 7.42-7.65 (11H, m, ArH), 7.73-7.80 (2H, m, ArH), 7.92-7.98 (2H, m, ArH), 7.94 (2H, d, J=8.2 Hz, ArH), 8.62 (2H, d, J=8.6 Hz, ArH), 11.49 (1H, br s, NH).

$^{13}$C-NMR (50.3 MHz, CDCl$_3$): δ 56.4 (CH$_2$), 60.3 (CH$_2$), 123.3 (ArCH), 125.6 (ArCH), 125.9 (ArCH), 126.8 (quaternary ArC), 127.5 (ArCH), 127.6 (ArCH), 127.8 (quaternary ArC), 127.9 (quaternary ArC), 128.3 (ArCH), 128.6 (ArCH), 128.7 (ArCH), 130.2 (ArCH), 131.4 (quaternary ArC), 131.6 (ArCH), 133.1 (ArCH), 133.3 (quaternary ArC), 135.0 (quaternary ArC), 137.4 (quaternary ArC), 137.6 (quaternary ArC), 170.2 (CO), 196.4 (CO).

Example 1-2: Synthesis of Nickel (II) Complex Having Glycine Moiety [Chiral Glycine Equivalent (S-Isomer)]

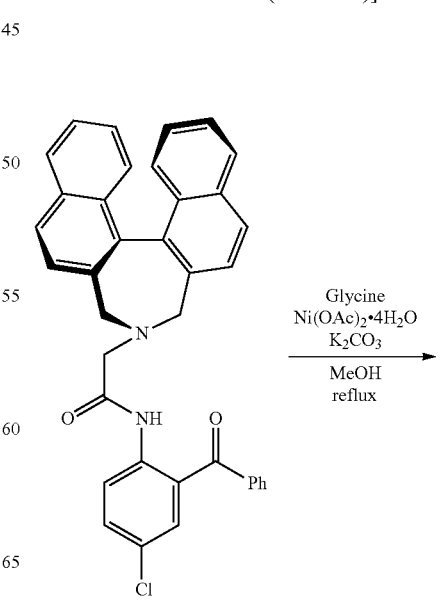

-continued

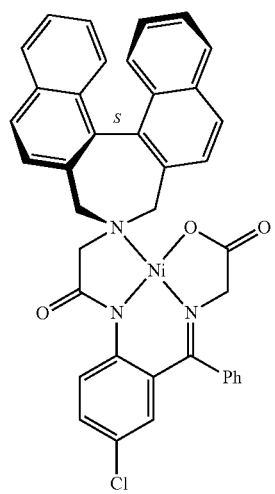

chiral glycine equivalent (S-isomer)

Under an argon atmosphere, to a methanol solution (30 mL, methanol was preliminarily deaerated by ultrasonication under reduced pressure and subsequent argon blowing for 40 minutes or longer) of (S)-N-(2-benzoyl-4-chlorophenyl)-2-[3,5-dihydro-4H-dinaphtho[2,1-c:1′,2′-e]azepin-4-yl]acetamide (0.2 g, 0.353 mmol), nickel acetate tetrahydrate (0.176 g, 0.706 mmol), glycine (0.132 g, 1.763 mmol), and anhydrous potassium carbonate (0.439 g, 3.174 mmol) were added. The mixture was refluxed for 1 hour. After the end of the reaction, the reaction mixture was subjected to phase separation with dichloromethane (20 mL), water (20 mL), and 1 N hydrochloric acid (5 mL) and the organic layer was separated. The organic layer was washed with saturated brine (12 mL, 3 times), dried over sodium sulfate, and then concentrated to dryness to give a crude product (0.259 g). The obtained crude product was dissolved in dichloromethane (2 mL), and ethyl acetate (2 mL) was added to the solution. The mixture was left to stand to allow crystals to precipitate. The crystals were separated by filtration, and then blow-dried at 50° C. to give an S-form nickel (II) complex having a glycine moiety (chiral glycine equivalent (S-isomer)) (0.22 g, yield: 91.7%) as red crystals.

ESI-MS (positive mode): m/z=680.1 for [M+H]$^+$.

HPLC analysis was conducted on the obtained compound under the above <HPLC conditions-1: complex analysis conditions>. The results are shown in Table 1 and FIG. 1.

TABLE 1

| Retention time in HPLC (min) |
| --- |
| 19.54 |

Example 1-3: Synthesis of Nickel (II) Complex Having Glycine Moiety [Chiral Glycine Equivalent (R-Isomer)]

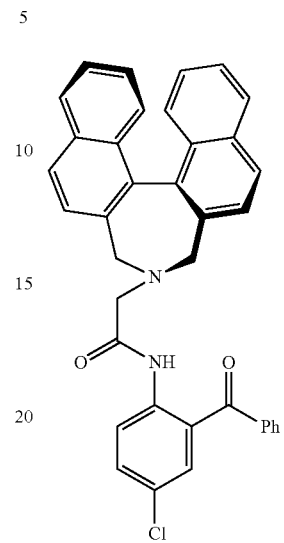

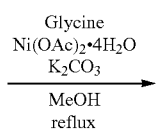

Glycine
Ni(OAc)$_2$•4H$_2$O
K$_2$CO$_3$
$\xrightarrow{\text{MeOH} \atop \text{reflux}}$

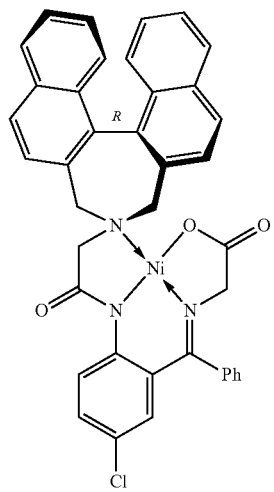

chiral glycine equivalent (R-isomer)

Under an argon atmosphere, to a methanol solution (150 mL, methanol was preliminarily deaerated by ultrasonication under reduced pressure and subsequent argon blowing for 40 minutes or longer) of (R)-N-(2-benzoyl-4-chlorophenyl)-2-[3,5-dihydro-4H-dinaphtho[2,1-c:1′,2′-e]azepin-4-yl]acetamide (1.0 g, 1.763 mmol), nickel acetate tetrahydrate (0.878 g, 3.527 mmol), glycine (0.662 g, 8.817 mmol), and potassium carbonate (2.194 g, 15.871 mmol) were added. The mixture was refluxed for 1 hour. After the end of the reaction, the reaction mixture was slightly concentrated and subjected to phase separation with dichloromethane (100 mL), water (70 mL), and 1 N hydrochloric acid (30 mL) and the organic layer was separated. The organic layer was washed with water (60 mL) and with saturated brine (60 mL, twice), dried over sodium sulfate, and then concentrated to dryness to give a crude product (1.182 g). The obtained crude product was dissolved in dichloromethane (10 mL), and ethyl acetate (10 mL) was added to the solution. The mixture was left to stand to allow crystals to precipitate. The crystals were separated by filtration, and then blow-dried at 50° C. to give an R-form nickel (II) complex having a glycine moiety (chiral glycine equivalent (R-isomer)) (0.99 g, yield: 82.4%) as red crystals.

ESI-MS (positive mode): m/z=680.1 for [M+H]$^+$.

$^1$H-NMR (200 MHz, CDCl$_3$): δ 2.75 [1H, d, J=12.1 Hz, one of azepine C(α)H$_2$N], 3.39 [1H, d, J=15.9 Hz, one of azepine C(α')H$_2$N], 3.65 (2H, s, CH$_2$ of Gly part), 3.75 (1H, d, J=13.6 Hz, one of acetanilide NCOCH$_2$), 4.05 [1H, d, J=15.9 Hz, one of azepine C(α')H$_2$N], 4.07 (1H, d, J=13.6 Hz, one of acetanilide NCOCH$_2$), 4.79 [1 H, d, J=12.1 Hz, one of azepine C(α)H$_2$N], 6.83 (1H, d, J=2.4 Hz), 6.92-7.02 (1H, m, ArH), 7.03-7.13 (1H, m, ArH), 7.19-7.58 (11H, m, ArH), 7.92-8.02 (3H, m, ArH), 8.10 (1H, d, J=8.3 Hz, ArH), 8.52 (1H, d, J=9.2 Hz, ArH), 8.57 (1H, d, J=8.3 Hz, ArH).

$^{13}$C-NMR (50.3 MHz, CDCl$_3$): δ 58.7 (NCOCH$_2$), 61.3 (2×CH$_2$), 64.6 (CH$_2$), 125.6 (ArCH), 125.7 (ArCH), 125.9 (ArCH), 126.1 (ArCH), 126.2 (quaternary ArC), 126.37 (ArCH), 126.44 (ArCH), 126.8 (quaternary ArC), 127.4 (ArCH), 127.6 (ArCH), 128.0 (quaternary ArC), 128.4 (ArCH), 128.5 (ArCH), 128.9 (ArCH), 129.0 (ArCH), 129.8 (ArCH), 130.0 (ArCH), 130.1 (ArCH), 131.2 (quaternary ArC), 132.2 (ArCH), 132.5 (ArCH), 133.7 (quaternary ArC), 133.9 (quaternary ArC), 135.7 (quaternary ArC), 141.0 (quaternary ArC), 171.4, 174.8, 176.6 (CN and 2×CO).

Figure 2:
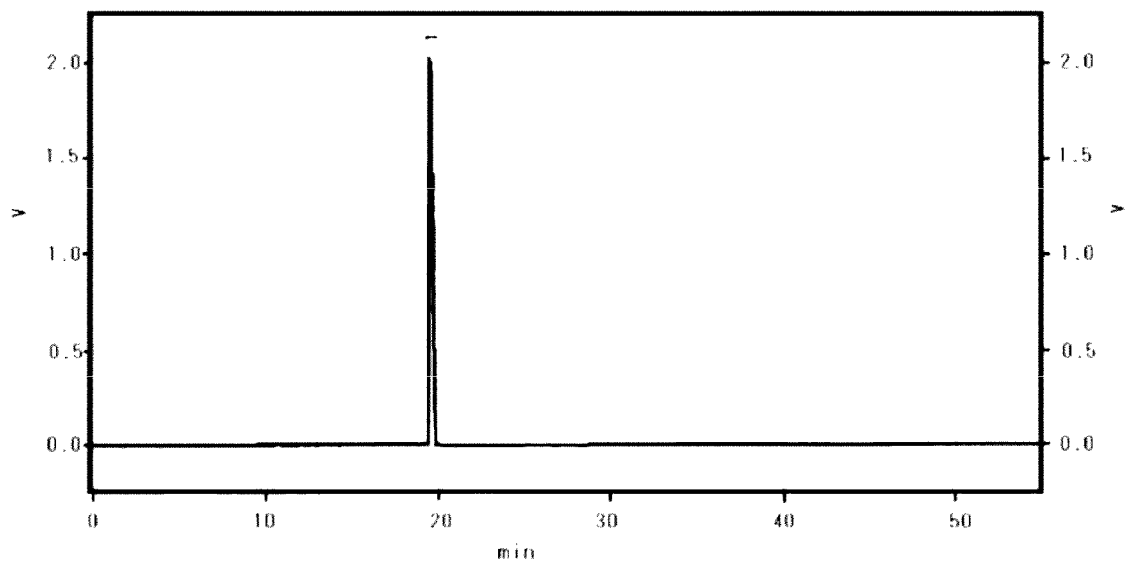
FIG. 2 shows a HPLC chromatogram of the compound prepared in Example 1-3.

HPLC analysis was conducted on the obtained compound under the above <HPLC conditions-1: complex analysis conditions>. The results are shown in Table 2 and FIG. 2.

TABLE 2

| Retention time in HPLC (min) |
| --- |
| 19.68 |

Example 2

Alkylation Reaction of Chiral Glycine Equivalent and Synthesis of Optically Active α-Amino Acid Example 2-1: Synthesis of Nickel (II) Complex Having L-phenylalanine Moiety by Alkylation Reaction with Benzyl Bromide

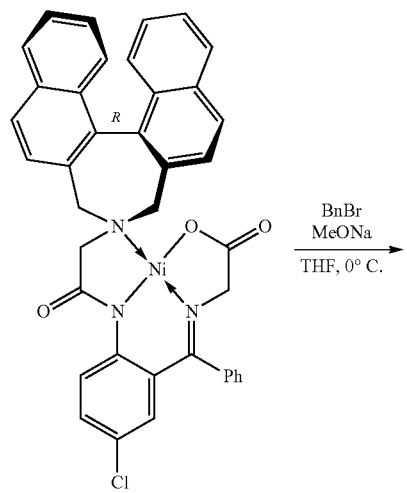

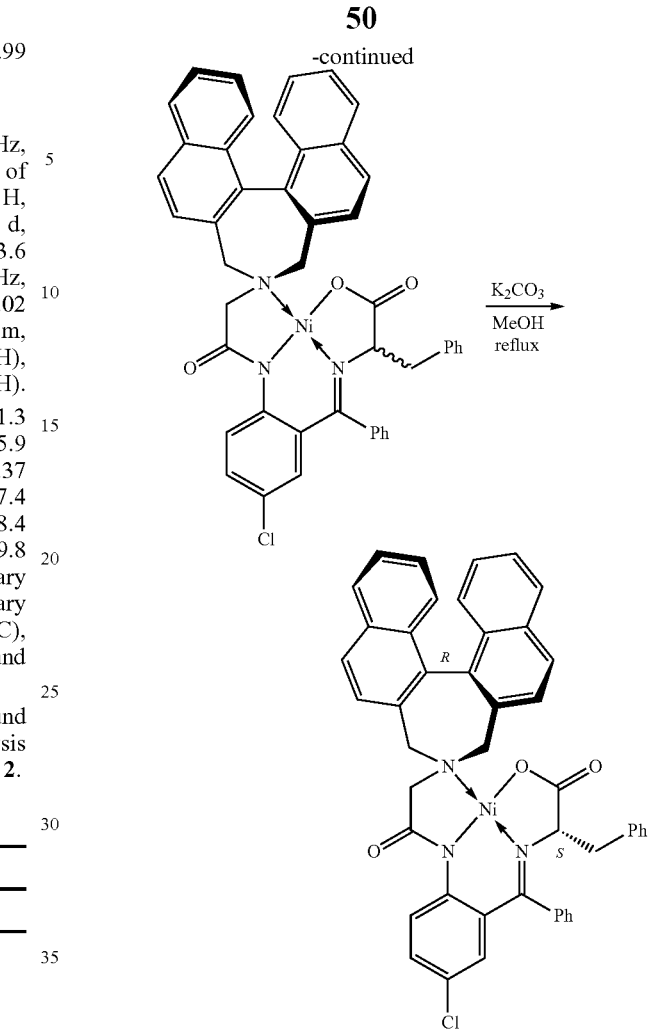

Under an argon atmosphere, to a tetrahydrofuran (THF) solution (2.6 mL) of a chiral glycine equivalent (R-isomer) (150.0 mg, 0.220 mmol), a solution of benzyl bromide (41.5 mg, 0.242 mmol) in THF (0.4 mL) was added. To this, a methanol solution of sodium methoxide (35.7 mg, 0.661 mmol) was added dropwise under an argon atmosphere at 0° C., and the mixture was stirred at 0° C. for 2 hours. After the end of the reaction, the reaction mixture was subjected to phase separation with water (10 mL) and ethyl acetate (10 mL), and the aqueous layer was extracted with ethyl acetate (10 mL) twice. The organic layer was washed with saturated brine (10 mL), dried over sodium sulfate, and then concentrated to dryness to give a red solid (165.6 mg). To a methanol solution (3.3 mL) of the obtained red solid, anhydrous potassium carbonate (59.4 mg, 0.644 mmol) was added, and the mixture was refluxed for 22 hours. After the end of the reaction, the reaction mixture was added to an ice-cooled 0.5% acetic acid aqueous solution (22 mL), and the whole was stirred for 30 minutes to allow crystals to precipitate. The crystals were separated by filtration, and then blow-dried at 50° C. The obtained orange-red solid was purified by silica gel column chromatography (dichloromethane:acetone=40:1 (v/v)) to give a nickel (II) complex having an L-phenylalanine moiety (130.9 mg, yield: 77.1%, 98.0% de) as red crystals.

ESI-MS (positive mode): m/z calcd for C$_{46}$H$_{35}$ClN$_3$NiO$_3$ [M+H]$^+$ 770.17. found 770.2.

$^1$H-NMR (200 MHz, CDCl$_3$): δ 2.42 [1H, d, J=12.1 Hz, one of azepine C(α)H$_2$N], 2.59 (1H, H$_A$ of ABX type, J$_{AB}$=13.6 Hz, J$_{AX}$=5.5 Hz, one of Phe β-CH$_2$), 2.61 [1H, d, J=15.6 Hz, one of azepine C(α')H$_2$N], 2.76 and 3.17 (1H each, ABq, J=13.9 Hz, acetanilide NCOCH$_2$), 3.00 (1H, H$_B$ of ABX type, J$_{AB}$=13.6 Hz, J$_{BX}$=3.0 Hz, one of Phe β-CH$_2$), 3.68 [1H, d, J=15.6 Hz, one of azepine C(α')H$_2$N], 4.23 (1H, H$_X$ of ABX type, J$_{AX}$=5.5 Hz, J$_{BX}$=3.0 Hz, α-H of Phe part), 4.54 [1H, d, J=12.1 Hz, one of azepine C(α)H$_2$N], 6.67 (1H, d, J=2.4 Hz), 7.05-8.02 (21H, m, ArH), 8.09 (1H, d, J=8.4 Hz, ArH), 8.34 (1H, d, J=9.2 Hz, ArH), 8.68 (1H, d, J=8.2 Hz, ArH).

$^{13}$C-NMR (50.3 MHz, CDCl$_3$): δ 39.0 (β-CH$_2$ of Phe part), 57.5 (NCOCH$_2$), 61.6 and 65.9 (2×CH$_2$ of azepine), 72.1 (α-CH of Phe part), 125.2 (ArCH), 126.1 (quaternary ArC), 126.4 (ArCH), 127.1 (ArCH), 127.4 (ArCH), 127.5 (ArCH), 127.7 (ArCH), 127.8 (ArCH), 128.4 (ArCH), 128.6 (ArCH), 128.8 (quaternary ArC), 129.0 (ArCH), 129.1 (ArCH), 129.3 (ArCH), 129.4 (ArCH), 130.5 (ArCH), 131.0 (quaternary ArC), 131.2 (quaternary ArC), 131.4 (quaternary ArC), 131.8 (ArCH), 132.4 (ArCH), 132.7 (ArCH), 132.9 (quaternary ArC), 133.6 (quaternary ArC), 133.9 (quaternary ArC), 135.3 (quaternary ArC), 135.9 (quaternary ArC), 136.5 (quaternary ArC), 141.4 (quaternary ArC), 169.9, 174.3, 177.4 (CN and 2×CO).

Figure 3:
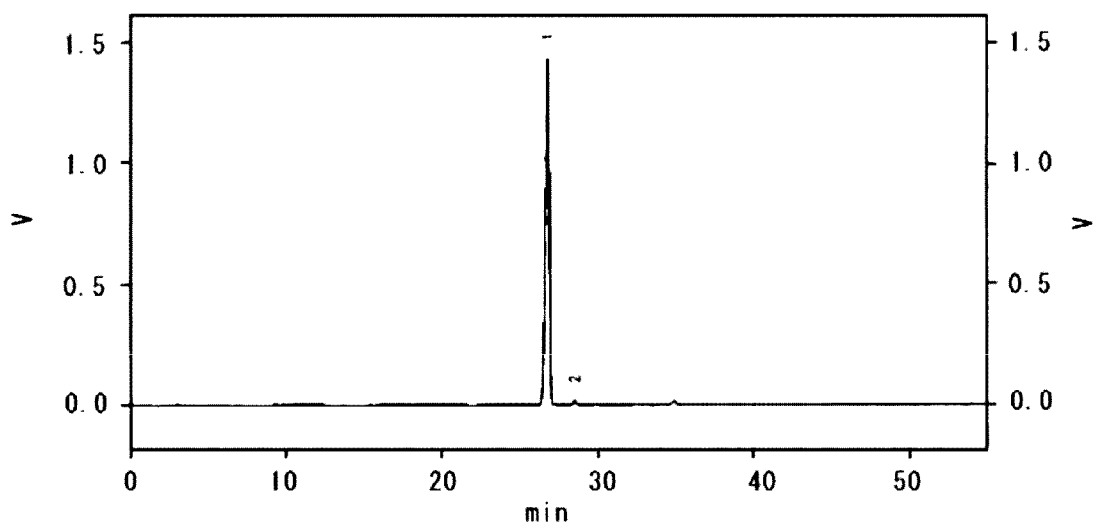
FIG. 3 shows a HPLC chromatogram of the compound prepared in Example 2-1.

HPLC analysis was conducted on the obtained compound under the above <HPLC conditions-1: complex analysis conditions>. The results are shown in Table 3 and FIG. 3.

TABLE 3

| Retention time in HPLC (min) | | Excess ratio (objective substance:isomer of objective substance) |
|---|---|---|
| Objective substance | Isomer of objective substance | |
| 26.85 | 28.51 | 98.0% de (99.0:1.0) |

Example 2-2: Synthesis of Nickel (II) Complex Having D-4-chlorophenylalanine Moiety by Alkylation Reaction with 4-chlorobenzyl bromide

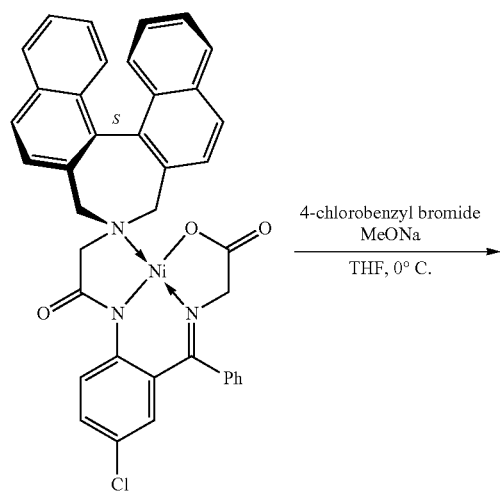

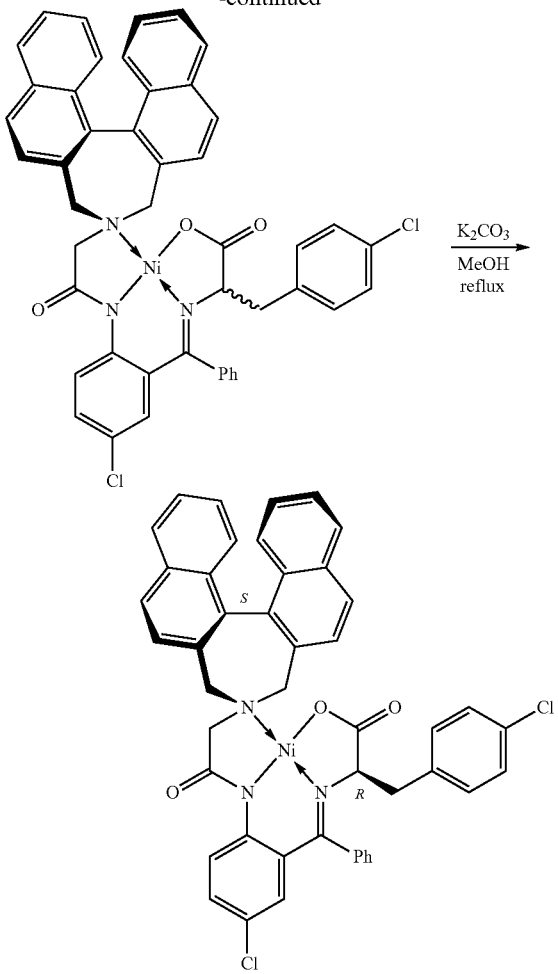

To a tetrahydrofuran (THF) solution (2.0 mL) of a chiral glycine equivalent (S-isomer) (100.0 mg, 0.147 mmol), 4-chlorobenzyl bromide (33.2 mg, 0.162 mmol) was added. To this, a methanol solution of sodium methoxide (23.8 mg, 0.441 mmol) was added dropwise at 0° C., and the mixture was stirred at 0° C. for 5 hours. After the end of the reaction, the reaction mixture was subjected to phase separation with water (10 mL) and ethyl acetate (10 mL), and the aqueous layer was extracted with ethyl acetate (10 mL) twice. The organic layer was washed with saturated brine (10 mL), dried over sodium sulfate, and then concentrated to dryness to give an orange-red solid (121.9 mg). To a methanol solution (3.3 mL) of the obtained orange-red solid (116.3 mg), anhydrous potassium carbonate (40.0 mg, 0.289 mmol) was added, and the mixture was refluxed for 24 hours. After the end of the reaction, the reaction mixture was added to an ice-cooled 0.5% acetic acid aqueous solution (21 mL), and the whole was stirred for 30 minutes to allow crystals to precipitate. The crystals were separated by filtration, and then blow-dried at 50° C. The obtained orange-red solid was purified by silica gel column chromatography (dichloromethane:acetone=100:1 (v/v)) to give a nickel (II) complex having a D-4-chlorophenylalanine moiety (97.8 mg, yield: 87%, 99.8% de) as red crystals.

ESI-MS (positive mode): m/z calcd for C$_{46}$H$_{33}$Cl$_2$N$_3$NaNiO$_3$ [M+Na]$^+$ 826.12. found 826.2.

$^1$H-NMR (200 MHz, CDCl$_3$): δ 2.36 [1H, d, J=12.3 Hz, one of azepine C(α)H$_2$N], 2.55 (1H, H$_A$ of ABX type, $J_{AB}$=13.6 Hz, $J_{AX}$=4.8 Hz, one of 4-Cl-Phe β-CH$_2$), 2.69 [1H, d, J=15.8 Hz, one of azepine C(α')H$_2$N], 2.70 and 3.20 (1H each, ABq, J=13.8 Hz, acetanilide NCOCH$_2$), 2.94 (1H, H$_B$ of ABX type, $J_{AB}$=13.6 Hz, $J_{BX}$=3.3 Hz, one of p-Cl-Phe β-CH$_2$), 3.74 [1H, d, J=15.8 Hz, one of azepine C(α')H$_2$N], 4.19 (1H, H$_X$ of ABX type, $J_{AX}$=4.8 Hz, $J_{BX}$=3.3 Hz, CL-H of p-Cl-Phe part), 4.59 [1H, d, J=12.3 Hz, one of azepine C(α)H$_2$N], 6.58 (1H, d, J=2.6 Hz), 6.95-7.07 (2H, m, ArH), 7.14-7.63 (13H, m, ArH), 7.64-7.72 (2H, m, ArH), 7.92-8.02 (3H, m, ArH), 8.11 (1H, d, J=8.4 Hz, ArH), 8.39 (1H, d, J=9.2 Hz, ArH), 8.83 (1H, d, J=8.2 Hz, ArH).

$^{13}$C-NMR (50.3 MHz, CDCl$_3$): δ 38.5 (β-CH$_2$ of p-Cl-Phe part), 57.9 (NCOCH$_2$), 61.6 and 66.0 (2×CH$_2$ of azepine), 71.8 (α-CH of p-Cl-Phe part), 125.2 (ArCH), 126.1 (quaternary ArC), 126.3 (ArCH), 126.4 (ArCH), 127.0 (ArCH), 127.3 (ArCH), 127.4 (quaternary ArC), 127.8 (ArCH), 128.2 (quaternary ArC), 128.5 (ArCH), 129.1 (ArCH), 129.2 (ArCH), 129.4 (ArCH), 130.5 (ArCH), 130.9 (quaternary ArC), 131.1 (quaternary ArC), 131.4 (quaternary ArC), 132.4 (ArCH), 132.8 (ArCH), 133.0 (ArCH), 133.6 (quaternary ArC), 133.86 (quaternary ArC), 133.93 (quaternary ArC), 134.8 (quaternary ArC), 135.1 (quaternary ArC), 136.0 (quaternary ArC), 141.4 (quaternary ArC), 170.2, 174.4, 177.0 (CN and 2×CO).

Figure 4:
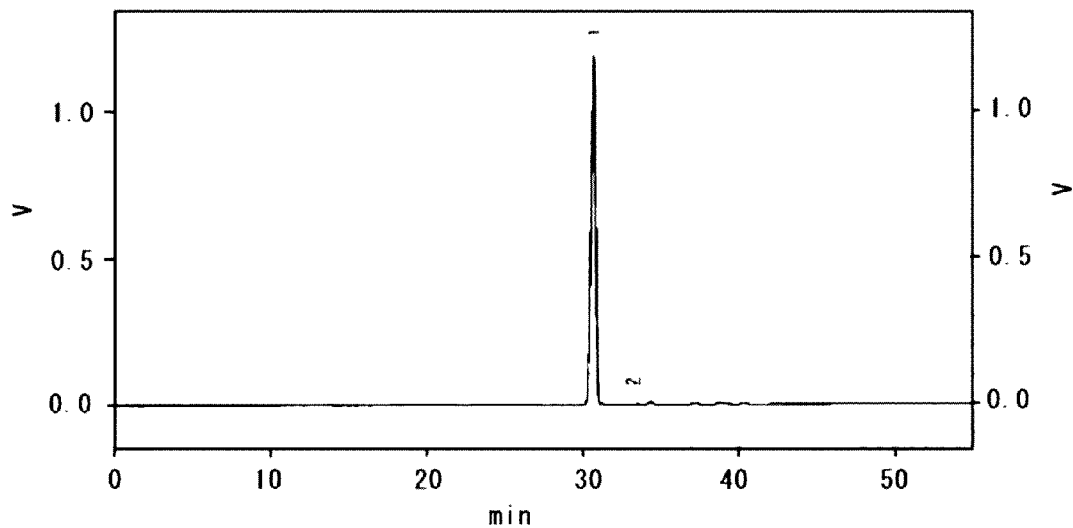
FIG. 4 shows a HPLC chromatogram of the compound prepared in Example 2-2.

HPLC analysis was conducted on the obtained compound under the above <HPLC conditions-1: complex analysis conditions>. The results are shown in Table 4 and FIG. 4.

TABLE 4

| Retention time in HPLC (min) | | Excess ratio (objective substance:isomer of objective substance) |
|---|---|---|
| Objective substance | Isomer of objective substance | |
| 30.82 | 33.15 | 99.8% de (99.9:0.1) |

Example 2-3: Release of D-4-chlorophenylalanine from Nickel (II) Complex Having D-4-chlorophenylalanine Moiety Under Acidic Conditions and Protection of D-4-chlorophenylalanine with Boc Group

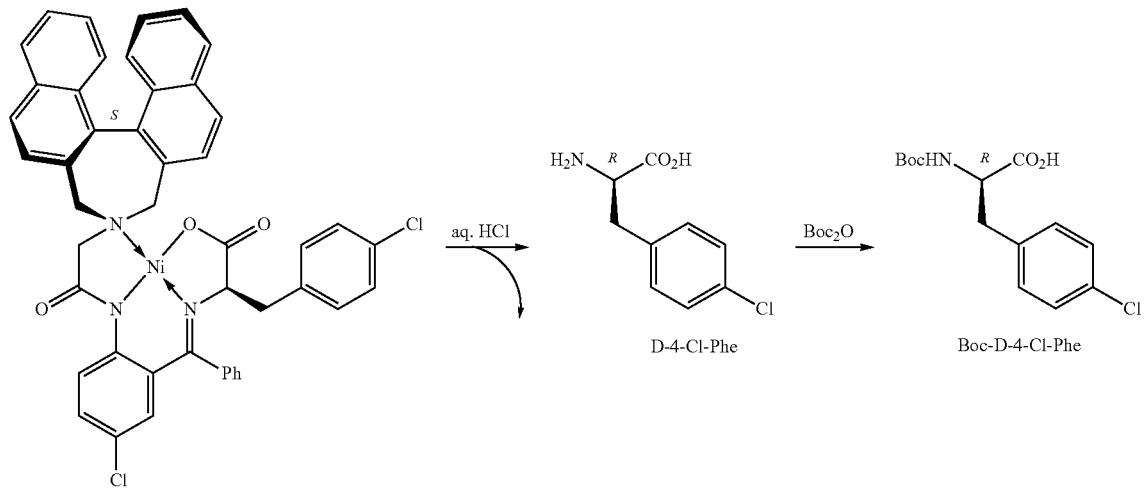

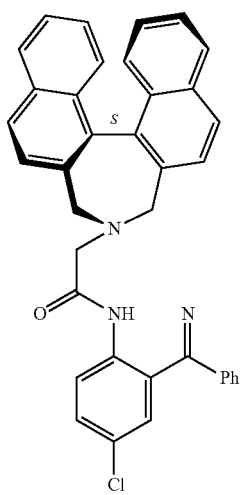

To a suspension of a nickel (II) complex having a D-4-chlorophenylalanine moiety (92.5 mg, 0.115 mmol) in methanol (2.8 mL), 1 N hydrochloric acid (0.6 mL, 0.574 mmol) was added, and the mixture was stirred at 40° C. for 6 hours. After the end of the reaction, the reaction mixture was concentrated, and the residue was subjected to phase separation with dichloromethane (10 mL) and water (10 mL). The aqueous layer was separated, and the solvent was removed by evaporation. The obtained solid was dissolved in 9% aqueous ammonia (3 mL). The solution was passed through a cation exchange resin column [SK-1B, 18 mL, eluent: 2 to 4% aqueous ammonia] to give a D-4-chlorophenylalanine crude product (22.0 mg, yield: 96%). Meanwhile, the organic layer was washed with 4% aqueous ammonia (10 mL, twice), with water (10 mL, twice), and then with saturated brine (10 mL, twice). The organic layer was dried over sodium sulfate, and then the solvent was removed by evaporation to give a chiral auxiliary (S-isomer) (62.5 mg, yield: 96%).

The D-4-chlorophenylalanine crude product (22.0 mg, 0.110 mmol) was dissolved in water (2 mL) and acetone (1.0 mL). To the solution, a solution of (Boc)$_2$O (40.4 mg, 0.185 mmol) in acetone (0.5 mL) and a solution of triethylamine (18.8 mg, 0.186 mmol) in acetone (0.5 mL) were added. The mixture was stirred at room temperature for 44 hours. The reaction mixture was concentrated until the volume was reduced to 2 mL or less, and then toluene (5 mL) was added thereto. To this, 4 N hydrochloric acid was added under stirring until the pH of the aqueous layer was reduced to 2 to 3. The organic layer was separated and washed with saturated brine (5 mL, twice). The organic layer was dried over magnesium sulfate, and then the solvent was removed by evaporation to give Boc-D-4-chlorophenylalanine (28.7 mg, 87.3%, 98.6% ee) as a white solid.

Figure 5:
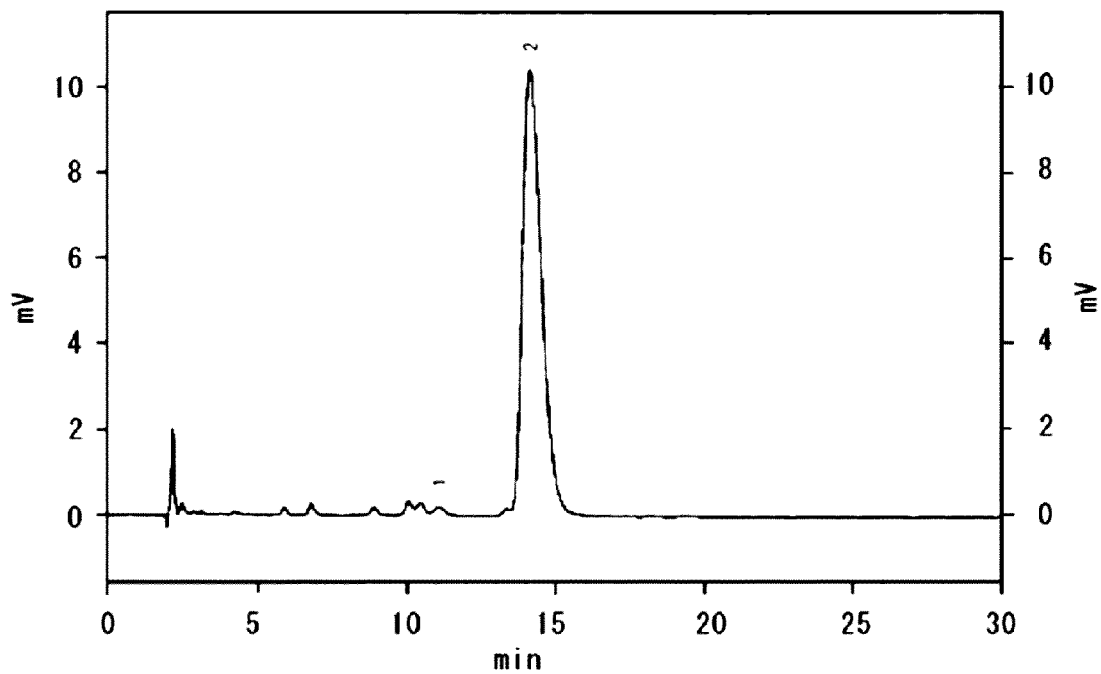
FIG. 5 shows a HPLC chromatogram of the compound prepared in Example 2-3.

HPLC analysis was conducted on the obtained compound under the following conditions. The results are shown in Table 5 and FIG. 5.

<HPLC Conditions: Boc-D-4-Cl-Phe Chiral Analysis Conditions>

Column: CHIRALPAK AD-RH (5 μm, 150×4.6 mm i.d.)
Eluent: A:B=35:65
  A=0.1% phosphoric acid aqueous solution
  B=0.1% solution of phosphoric acid in acetonitrile
Flow rate: 1.0 mL/min
Temperature: 35° C.
Detector: UV 254 nm

TABLE 5

| Retention time in HPLC (min) | | |
|---|---|---|
| Isomer of objective substance | Objective substance | Excess ratio (isomer of objective substance:objective substance) |
| Boc-L-4-chlorophenylalanine | Boc-D-4-chlorophenylalanine | |
| 11.08 | 14.16 | 98.6% ee (0.7:99.3) |

Example 2-4: Synthesis of Nickel (II) Complex Having 3-(2-naphthyl)-D-alanine Moiety by Alkylation Reaction with 2-(bromomethyl)naphthalene

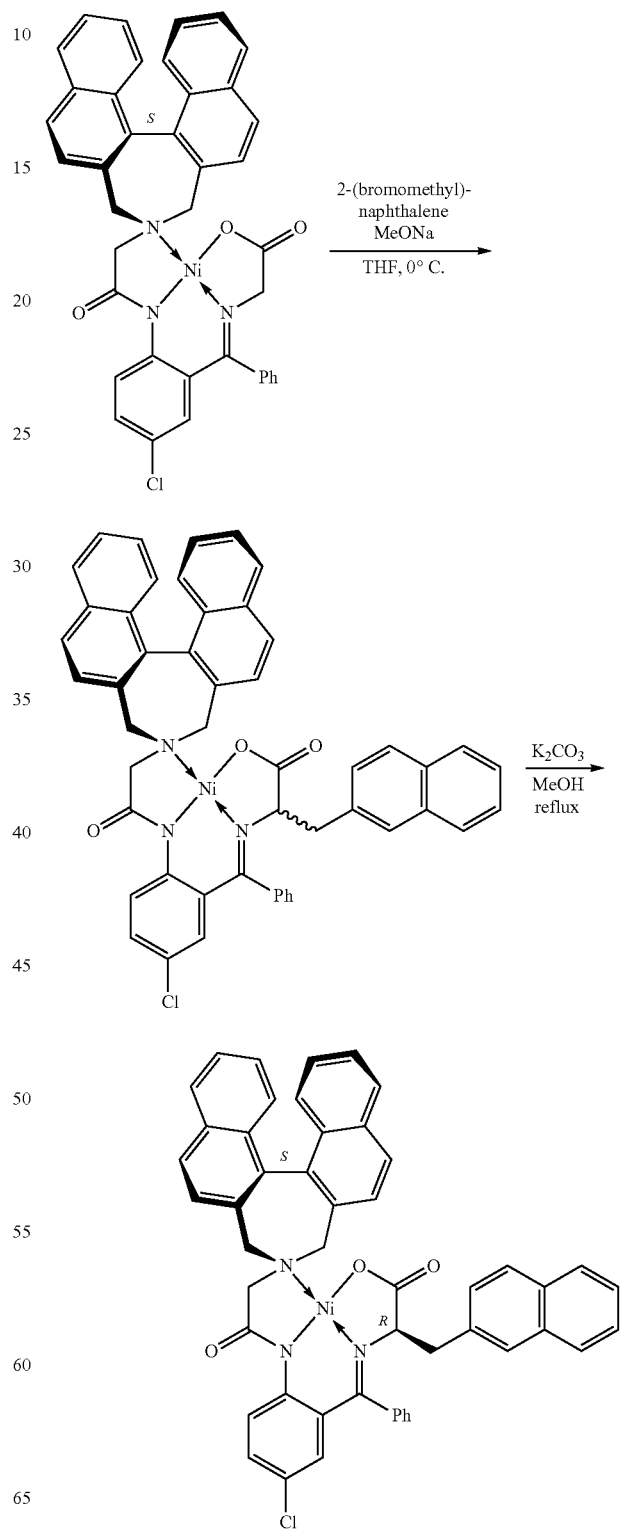

Under an argon atmosphere, to a tetrahydrofuran (THF) solution (4.0 mL) of a chiral glycine equivalent (S-isomer) (200.0 mg, 0.294 mmol), 2-(bromomethyl)naphthalene (71.5 mg, 0.323 mmol) was added at 0° C. To this, a methanol solution of sodium methoxide (95.2 mg, 1.763 mmol) was added dropwise, and the mixture was stirred at 0° C. for 1.5 hours. The reaction mixture was subjected to phase separation with water (10 mL) and ethyl acetate (10 mL), and the aqueous layer was extracted with ethyl acetate (10 mL) 3 times. The organic layers were combined and washed with saturated brine (10 mL), dried over sodium sulfate, and then concentrated to dryness to give an orange-red solid (275.9 mg). To a methanol solution (5.4 mL) of the obtained orange-red solid (266.6 mg), anhydrous potassium carbonate (89.8 mg, 0.650 mmol) was added, and the mixture was refluxed for 24 hours. The reaction mixture was added to an ice-cooled 0.5% acetic acid aqueous solution (50 mL), and the whole was stirred for 30 minutes. The precipitated crystals were separated by filtration, and then blow-dried at 50° C. The obtained orange-red solid was purified by silica gel column chromatography (dichloromethane:acetone=50:1 (v/v)) to give a nickel (II) complex having a 3-(2-naphthyl)-D-alanine moiety (232.9 mg, 87.4%, chemical purity: 97.9%, 99.8% de) as red crystals.

ESI-MS (positive mode): m/z calcd for $C_{50}H_{37}ClN_3NiO_3$ [M+H]$^+$ 820.19. found 820.3.

$^1$H-NMR (200 MHz, CDCl$_3$): δ 1.84 (1H, d, J=13.9 Hz, one of acetanilide NCOCH$_2$), 2.12 [1H, d, J=12.3 Hz, one of azepine C(α)H$_2$N], 2.13 [1H, d, J=15.6 Hz, one of azepine C(α')H$_2$N], 2.54 [1H, d, J=15.6 Hz, one of azepine C(α') H$_2$N], 2.74 (1H, H$_A$ of ABX type, J$_{AB}$=13.6 Hz, J$_{Ax}$=5.0 Hz, one of AA β-CH$_2$), 2.92 (1H, d, J=13.9 Hz, one of acetanilide NCOCH$_2$), 3.15 (1H, H$_B$ of ABX type, J$_{AB}$=13.6 Hz, J$_{BX}$=2.9 Hz, one of AA β-CH$_2$), 4.25 (1H, H$_X$ of ABX type, J$_{Ax}$=5.0 Hz, J$_{BX}$=2.9 Hz, α-H of AA part), 4.43 [1H, d, J=12.3 Hz, one of azepine C(α)H$_2$N], 6.52 (1H, d, J=8.4 Hz, ArH), 6.61 (1H, d, J=2.6 Hz, ArH), 7.01 (1H, br d, J=7.7 Hz, ArH), 7.09-7.33 (6H, m, ArH), 7.38-8.14 (15H, m, ArH), 8.21 (1H, br d, J=7.9 Hz, ArH), 8.34 (1H, d, J=9.2 Hz, ArH), 8.75 (1H, d, J=8.2 Hz, ArH).

$^{13}$C-NMR (50.3 MHz, CDCl$_3$): δ 39.1 (β-CH$_2$ of Phe part), 57.1 (NCOCH$_2$), 61.5 and 65.3 (2×CH$_2$ of azepine), 72.3 (α-CH of AA part), 125.2 (ArCH), 126.0 (quaternary ArC), 126.2 (ArCH), 126.3 (ArCH), 126.7 (ArCH), 126.9 (ArCH), 127.1 (ArCH), 127.3 (ArCH), 127.4 (ArCH), 127.5 (ArCH), 127.8 (ArCH), 128.0 (ArCH), 128.2 (quaternary ArC), 128.3 (ArCH), 128.4 (ArCH), 128.5 (ArCH), 128.7 (ArCH), 129.1 (ArCH), 129.3 (ArCH), 129.4 (ArCH), 130.0 (ArCH), 130.4 (ArCH), 130.9 (quaternary ArC), 131.0 (quaternary ArC), 131.4 (quaternary ArC), 132.3 (ArCH), 132.6 (ArCH), 132.9 (quaternary ArC), 133.2 (quaternary ArC), 133.4 (quaternary ArC), 133.9 (quaternary ArC), 134.0 (quaternary ArC), 135.0 (quaternary ArC), 135.9 (quaternary ArC), 141.5 (quaternary ArC), 169.9, 174.3, 177.3 (CN and 2×CO).

Figure 6:
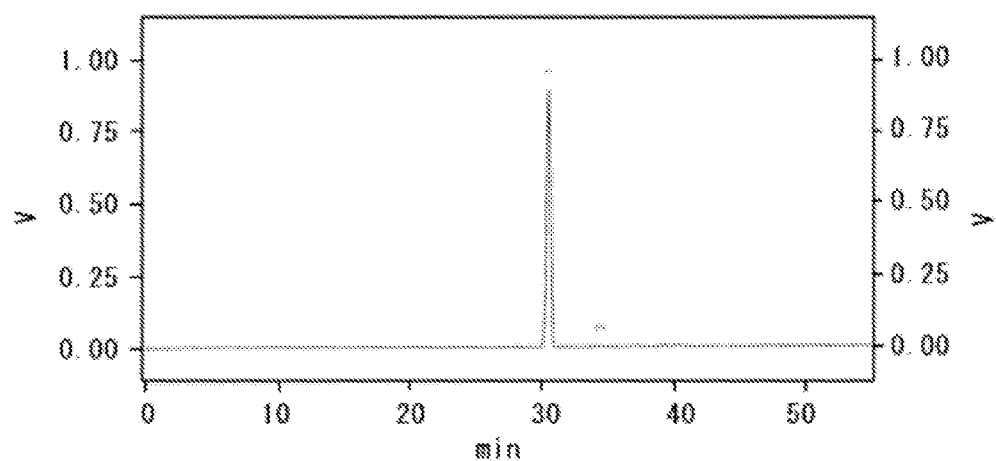
FIG. 6 shows a HPLC chromatogram of the compound prepared in Example 2-4.

HPLC analysis was conducted on the obtained compound under the above <HPLC conditions-1: complex analysis conditions>. The results are shown in Table 6 and FIG. 6.

TABLE 6

| Retention time in HPLC (min) | | Excess ratio (objective substance:isomer of objective substance) |
|---|---|---|
| Objective substance | Isomer of objective substance | |
| 30.68 | 34.47 | 99.8% de (99.9:0.1) |

Example 2-5: Release of 3-(2-naphthyl)-D-alanine from Nickel (II) Complex Having 3-(2-naphthyl)-D-alanine Moiety Under Acidic Conditions and Protection of 3-(2-naphthyl)-D-alanine with Boc Group

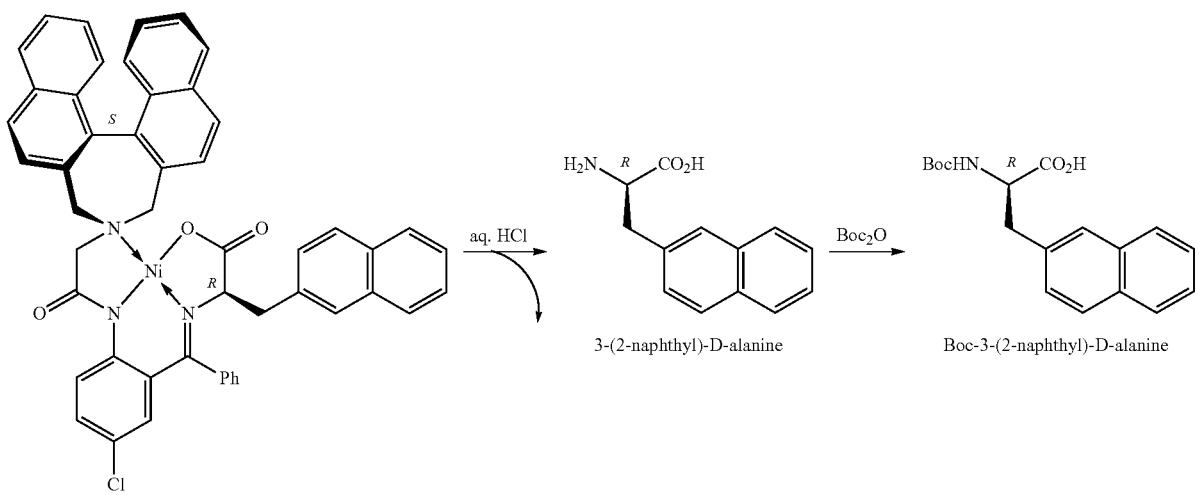

3-(2-naphthyl)-D-alanine

Boc-3-(2-naphthyl)-D-alanine

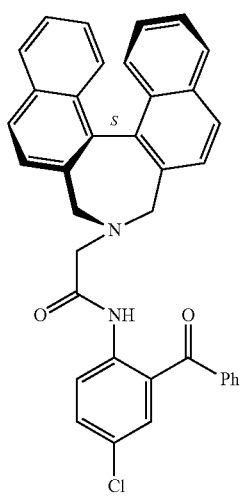

To a suspension of a nickel (II) complex having a 3-(2-naphthyl)-D-alanine moiety (100.0 mg, 0.122 mmol) in methanol (4.0 mL), 1N hydrochloric acid (0.61 mL, 0.609 mmol) was added, and the mixture was stirred at 40 to 50° C. for 8 hours. The reaction mixture was concentrated, and the residue was subjected to phase separation with dichloromethane (10 mL) and water (10 mL). The aqueous layer was separated, and the solvent was removed by evaporation. The obtained solid was dissolved in 9% aqueous ammonia (3 mL). The solution was passed through a cation exchange resin column [SK-1B, 21 mL, eluent: 2 to 4% aqueous ammonia] to give a 3-(2-naphthyl)-D-alanine crude product (22.0 mg, yield: 83.9%) as a white solid. Meanwhile, the organic layer was washed with 2% aqueous ammonia (10 mL, twice), with water (10 mL, twice), and then with saturated brine (10 mL, twice). The organic layer was dried over sodium sulfate, and then the solvent was removed by evaporation to give a chiral auxiliary (S-isomer) (58.7 mg, chemical purity: 98.5%, yield: 85.0%). The 3-(2-naphthyl)-D-alanine crude product (13.0 mg, 0.060 mmol) was dissolved in water (2 mL) and acetone (1.0 mL). To the solution, a solution of (Boc)$_2$O (21.1 mg, 0.097 mmol) in acetone (0.5 mL) and a solution of triethylamine (9.8 mg, 0.097 mmol) in acetone (0.5 mL) were added. The mixture was stirred at room temperature for 27 hours. The reaction mixture was concentrated until the volume was reduced to 2 mL or less, and then toluene (5 mL) was added thereto. To this, 1 N hydrochloric acid was added under stirring until the pH of the aqueous layer was reduced to 2 to 3. The aqueous layer was extracted with toluene (5 mL, 3 times). The organic layer was washed with brine (5 mL, twice) and dried over magnesium sulfate. The solvent was removed by evaporation to give a Boc-3-(2-naphthyl)-D-alanine (16.2 mg, yield: 85.1%, chemical purity: 96.6%, 99.3% ee) as a colorless solid.

Figure 7:
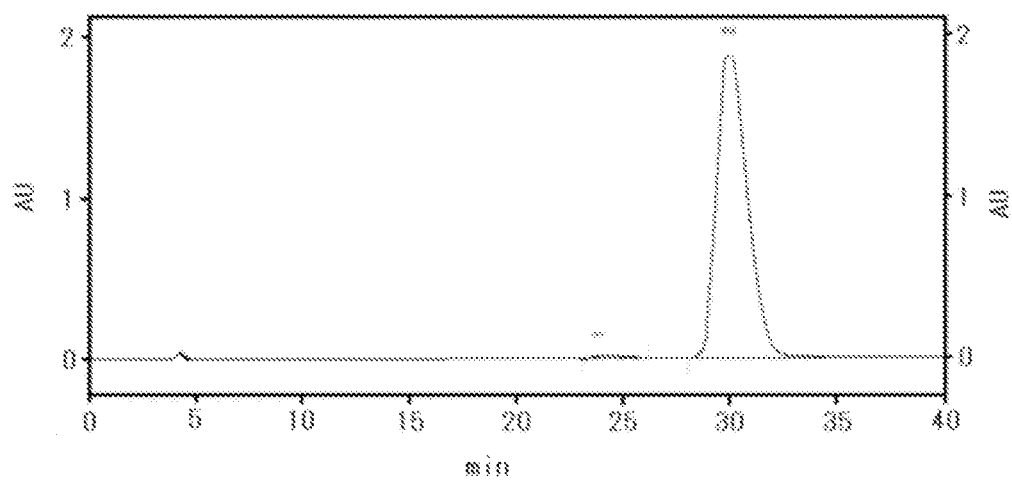
FIG. 7 shows a HPLC chromatogram of the compound prepared in Example 2-5.

HPLC analysis was conducted on the obtained compound under the following conditions. The results are shown in Table 7 and FIG. 7.

<HPLC Conditions: Boc-3-(2-naphthyl)-D-alanine Chiral Analysis Conditions>

Column: CHIRALPAK AD-RH (5 μm, 150×4.6 mm i.d.)
Eluent: A:B=35:65
 A=0.1% phosphoric acid aqueous solution
 B=0.1% solution of phosphoric acid in acetonitrile Flow rate: 0.5 mL/min
Temperature: 30° C.
Detector: UV 220 nm

TABLE 7

| Retention time in HPLC (min) | | Excess ratio (isomer of objective substance:objective substance) |
|---|---|---|
| Isomer of objective substance | Objective substance | |
| 23.93 | 29.93 | 99.3% ee (0.37:99.63) |

Example 2-6: Synthesis of Nickel (II) Complex Having 3-(3-pyridyl)-D-alanine Moiety by Alkylation Reaction with 3-(bromomethyl)pyridine

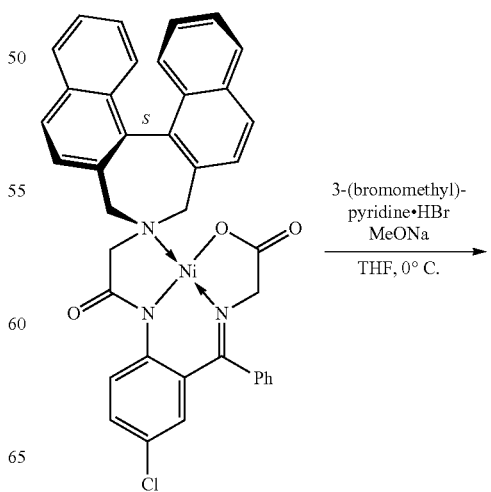

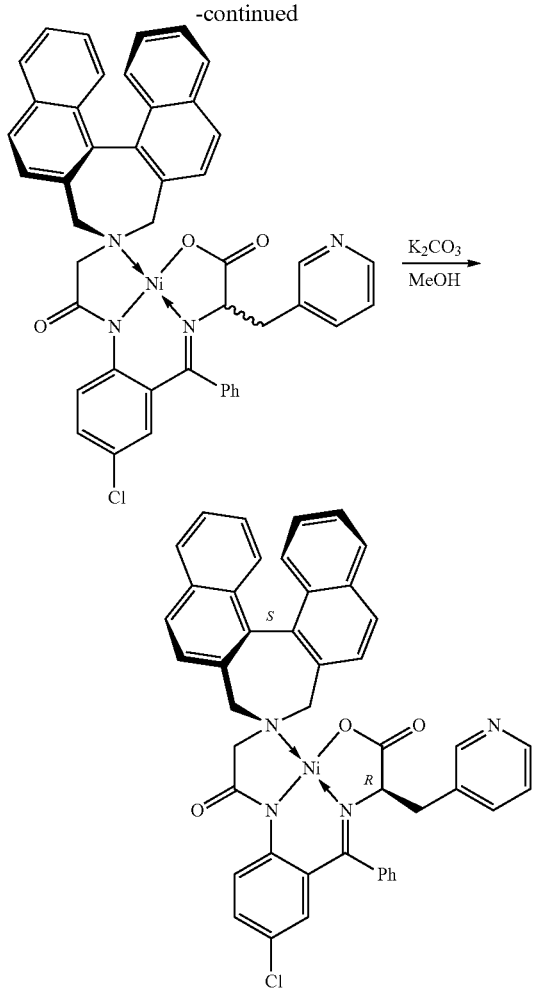

Under an argon atmosphere, to a tetrahydrofuran (THF) solution (4.0 mL) of a chiral glycine equivalent (S-isomer) (200.0 mg, 0.294 mmol), 3-(bromomethyl)pyridine hydrobromide (81.8 mg, 0.323 mmol) was added at 0° C. To this, a methanol solution of sodium methoxide (238.0 mg, 4.41 mmol) was added dropwise, and the mixture was stirred at 0° C. for 1 hour. The reaction mixture was subjected to phase separation with water (15 mL) and ethyl acetate (15 mL), and the aqueous layer was extracted with ethyl acetate (10 mL) 3 times. The organic layer was washed with saturated brine (10 mL) and dried over sodium sulfate. The solvent was removed by evaporation to give an orange-red solid (238.0 mg). To a methanol solution (2.0 mL) of the orange-red solid (231.1 mg), anhydrous potassium carbonate (82.8 mg, 0.599 mmol) was added, and the mixture was stirred at 40° C. for 24 hours under an argon atmosphere. The reaction mixture was added to an ice-cooled 0.5% acetic acid aqueous solution (20 mL), and the whole was stirred for 30 minutes. The precipitated crystals were separated by filtration, and then blow-dried at 50° C. The obtained orange-red solid was purified by silica gel column chromatography (dichloromethane:acetone=9:1 (v/v)) to give a nickel (II) complex having a 3-(3-pyridyl)-D-alanine moiety (171.2 mg, 77.8%, chemical purity: 97.9%, 99.3% de) as red crystals.

ESI-MS (positive mode) m/z calcd for $C_{45}H_{34}ClN_4NiO_3$ $[M+H]^+$ 771.17. found 771.2.

$^1$H-NMR (200 MHz, CDCl$_3$): δ2.42 [1H, d, J=12.1 Hz, one of azepine C(α)H$_2$N], 2.61 (1H, H$_A$ of ABX type, $J_{AB}$=13.8 Hz, $J_{AX}$=5.3 Hz, one of AA β-CH$_2$), 2.69 [1H, d, J=15.6 Hz, one of azepine C (α')H$_2$N], 2.87 (1H, d, J=13.8 Hz, one of acetanilide NCOCH$_2$) 3.02 (1H, H$_B$ of ABX type, $J_{AB}$=13.8 Hz, $J_{BX}$=2.6 Hz, one of AA β-CH$_2$), 3.27 (1H, d, J=13.8 Hz, one of acetanilide NCOCH$_2$) 3.80 [1H, d, J=15.6 Hz, one of azepine C(α')H$_2$N], 4.25 (1H, H$_X$ of ABX type, $J_{AX}$=5.3 Hz, $J_{BX}$=2.6 Hz, α-H of AA part), 4.56 [1H, d, J=12.1 Hz, one of azepine C(α)H$_2$N], 6.64 (1H, d, J=2.4 Hz), 7.02-7.65 (15H, m, ArH), 7.92-8.01 (3H, m, ArH), 8.11 (1H, d, J=8.4 Hz, ArH), 8.39 (1H, d, J=9.2 Hz, ArH), 8.74 (1H, d, J=8.2 Hz, ArH), 8.95 (1H, br s, ArH), 9.03 (1H, br d, J=2.7 Hz, ArH).

$^{13}$C-NMR (50.3 MHz, CDCl$_3$): δ 36.4 (β-CH$_2$), 57.8 (NCOCH$_2$), 61.6 and 65.8 (2×CH$_2$ of azepine), 71.3 (α-CH), 124.0 (ArCH), 125.2 (ArCH), 126.1 (quaternary ArC), 126.3 (ArCH), 126.4 (ArCH), 127.1 (ArCH), 127.3 (ArCH), 127.4 (ArCH), 127.7 (ArCH), 128.0 (quaternary ArC), 128.4 (ArCH), 128.6 (ArCH), 129.0 (ArCH), 129.2 (ArCH), 129.5 (ArCH), 130.6 (ArCH), 130.8 (quaternary ArC), 131.1 (quaternary ArC), 131.4 (quaternary ArC), 132.1 (quaternary ArC), 132.4 (ArCH), 132.8 (quaternary ArC), 132.9 (ArCH), 133.6 (quaternary ArC), 133.9 (quaternary ArC), 135.2 (quaternary ArC), 136.0 (quaternary ArC), 138.7 (quaternary ArC), 141.5 (quaternary ArC), 149.2 (quaternary ArC), 152.2 (quaternary ArC), 170.5, 174.3, 177.0 (CN and 2×CO).

Figure 8:
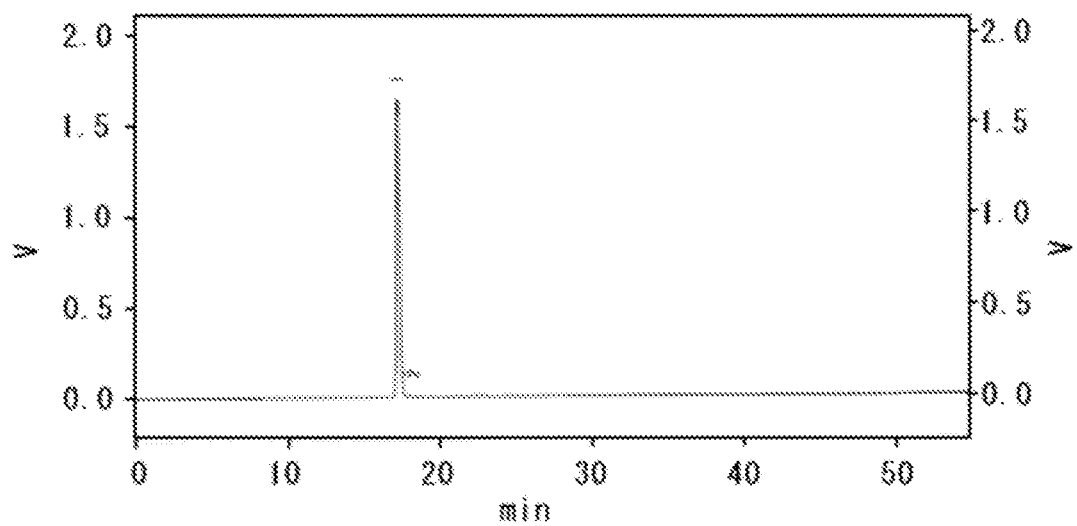
FIG. 8 shows a HPLC chromatogram of the compound prepared in Example 2-6.

HPLC analysis was conducted on the obtained compound under the above <HPLC conditions-1: complex analysis conditions>. The results are shown in Table 8 and FIG. 8.

TABLE 8

| Retention time in HPLC (min) | | Excess ratio |
|---|---|---|
| Objective substance | Isomer of objective substance | (objective substance:isomer of objective substance) |
| 17.34 | 18.03 | 99.3% de (99.64:0.36) |

Example 2-7: Release of 3-(3-pyridyl)-D-alanine from Nickel (II) Complex Having 3-(3-pyridyl)-D-alanine Moiety Under Acidic Conditions and Protection of 3-(3-pyridyl)-D-alanine with Boc Group

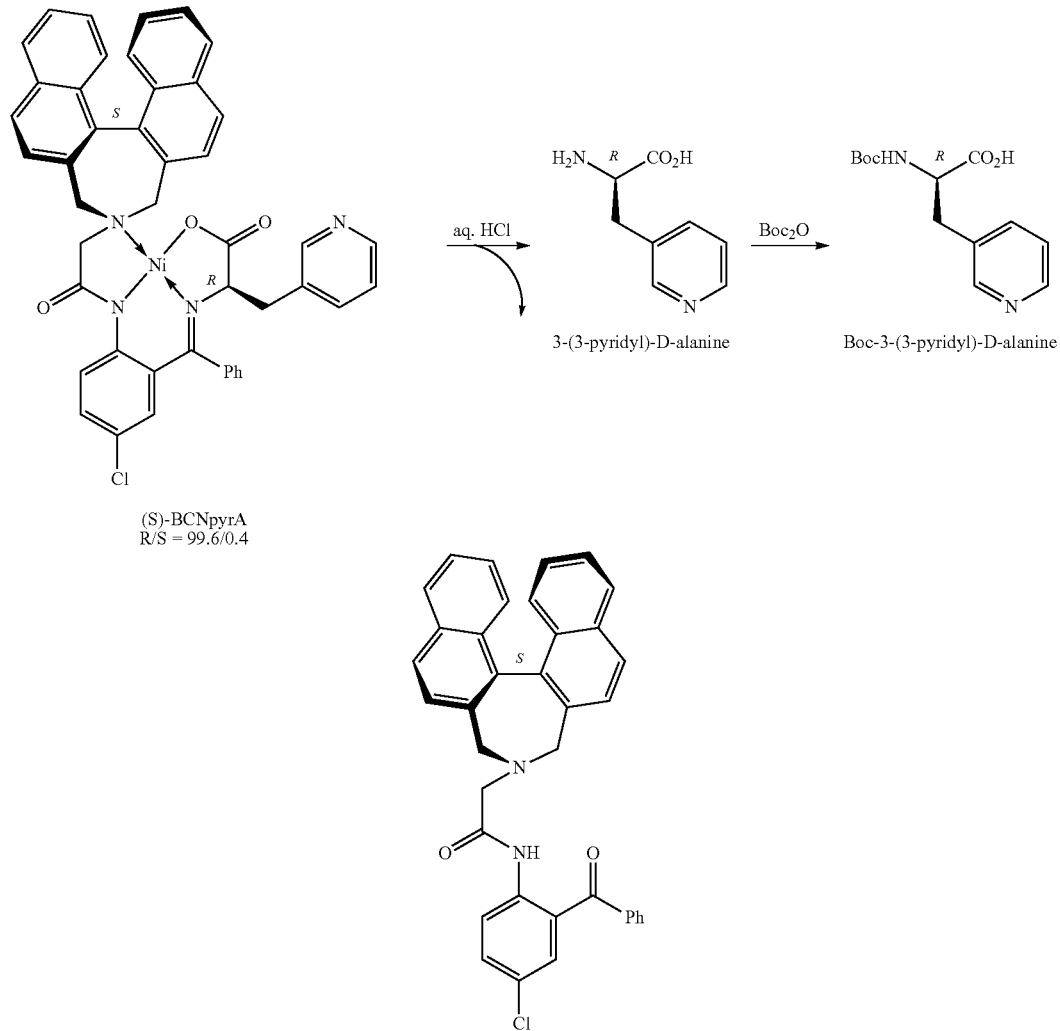

(S)-BCNpyrA
R/S = 99.6/0.4

To a suspension of a nickel (II) complex having a 3-(3-pyridyl)-D-alanine moiety (100.0 mg, 0.130 mmol) in methanol (3.0 mL), 1 N hydrochloric acid (0.65 mL, 0.648 mmol) was added, and the mixture was stirred at room temperature for 3 hours. The reaction mixture was concentrated under reduced pressure, and the residue was subjected to phase separation with dichloromethane (10 mL) and water (10 mL). The aqueous layer was separated, and the solvent was removed by evaporation. The obtained solid was dissolved in 8% aqueous ammonia (5 mL). The solution was passed through a cation exchange resin column [SK-1B, 40 mL, eluent: water and subsequently 4% aqueous ammonia] to give 3-(3-pyridyl)-D-alanine (17.7 mg, yield: 81.9%, 97.3% ee) as a white solid.

Figure 9:
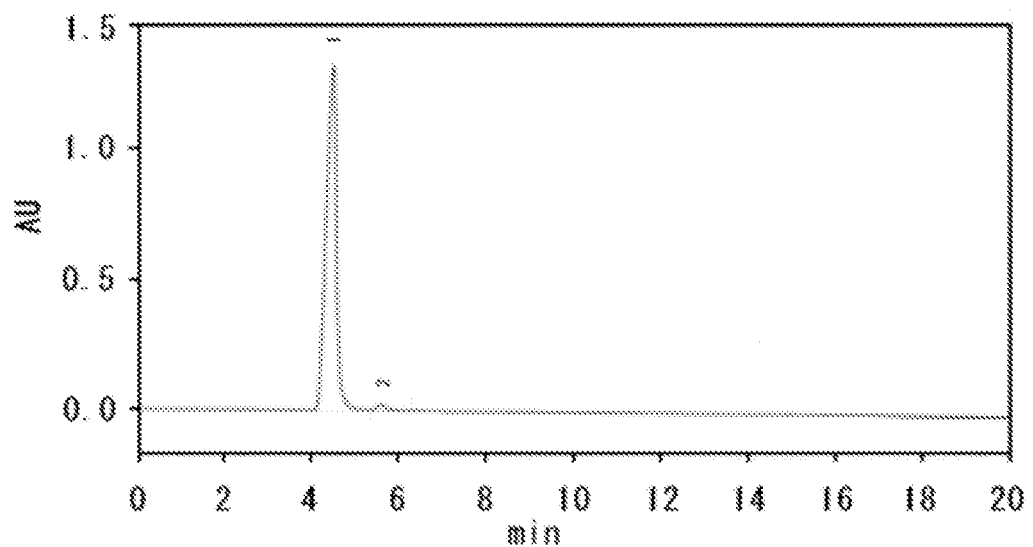
FIG. 9 shows a HPLC chromatogram of the compound prepared in Example 2-7.

HPLC analysis was conducted on the obtained compound under the following conditions. The results are shown in Table 9 and FIG. 9.

<HPLC Conditions: 3-(3-pyridyl)-D-alanine Chiral Analysis Conditions>
Column: CROWNPAK CR(+) (5 μm, 150×4.0 mm i.d.)
Eluent: perchloric acid aqueous solution (pH 1.0)
Flow rate: 0.4 mL/min
Temperature: 30° C.
Detector: UV 254 nm

TABLE 9

| Retention time in HPLC (min) | | Excess ratio |
|---|---|---|
| 3-(3-pyridyl)-D-alanine | 3-(3-pyridyl)-L-alanine | (objective substance:isomer of objective substance) |
| 4.3 | 5.6 | 97.3% ee (98.65:1.35) |

Meanwhile, the organic layer was washed with 2% aqueous ammonia (10 mL, twice), with water (10 mL, twice), and then with saturated brine (10 mL, twice). The organic layer was dried over sodium sulfate, and then the solvent was removed by evaporation to give a chiral auxiliary (S-isomer) (63.8 mg, chemical purity: 98.6%, yield: 86.9%).

3-(3-Pyridyl)-D-alanine (16.3 mg, 0.098 mmol) was dissolved in water (1 mL) and acetone (0.5 mL). To the solution, a solution of (Boc)₂O (34.3 mg, 0.157 mmol) in acetone (0.25 mL) and a solution of triethylamine (15.9 mg, 0.157 mmol) in acetone (0.25 mL) were added. The mixture was stirred at room temperature for 3.5 hours. The reaction mixture was concentrated under reduced pressure until the volume was reduced to 1 mL or less, and then 2-butanol (10 mL) was added thereto. To this, 1 N hydrochloric acid was added under stirring until the pH of the aqueous layer was reduced to 2 to 3. The aqueous layer was extracted with 2-butanol (10 mL, 3 times). The organic layer was washed with saturated brine (10 mL, twice) and dried over magnesium sulfate. The solvent was removed by evaporation to give Boc-3-(3-pyridyl)-D-alanine (20.5 mg, yield: 78.5%, chemical purity: 97.1%) as a colorless solid.

Example 2-8: Synthesis of Nickel (II) Complex Having L-allylglycine Moiety by Alkylation Reaction with Allyl Bromide

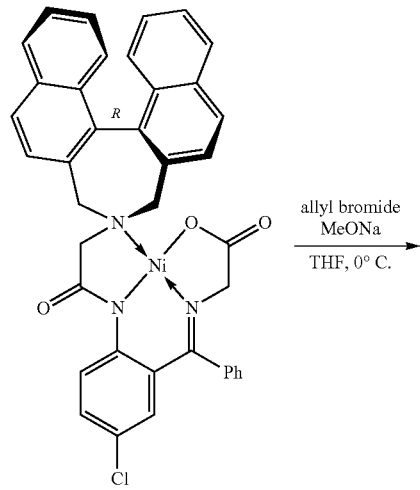

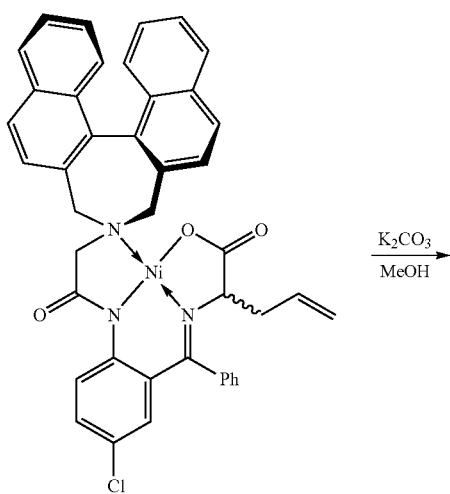

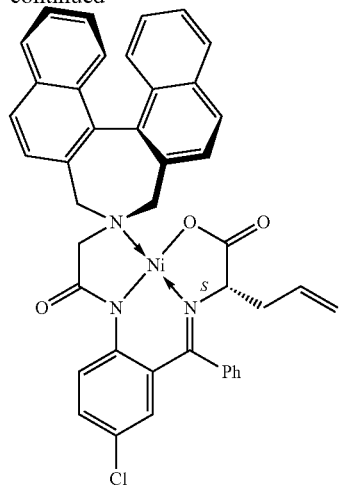

Under an argon atmosphere, to a tetrahydrofuran (THF) solution (3.5 mL) of a chiral glycine equivalent (R-isomer) (171.9 mg, 0.253 mmol), allyl bromide (33.6 mg, 0.278 mmol) was added at 0° C. To this, a methanol solution of sodium methoxide (40.9 mg, 0.758 mmol) was added dropwise, and the mixture was stirred at 0° C. for 1 hour. The reaction mixture was subjected to phase separation with water (10 mL) and ethyl acetate (10 mL), and the aqueous layer was extracted with ethyl acetate (10 mL) twice. The organic layers were combined and washed with saturated brine (10 mL), dried over sodium sulfate, and then concentrated to dryness to give an orange-red solid (184.5 mg). To a methanol solution (3.7 mL) of the obtained orange-red solid (184.5 mg), anhydrous potassium carbonate (70.8 mg, 0.512 mmol) was added, and the mixture was stirred at 40° C. for 3.5 hours under an argon atmosphere. The reaction mixture was added to an ice-cooled 0.5% acetic acid aqueous solution (37 mL), and the whole was stirred for 30 minutes. The precipitated crystals were separated by filtration, and then blow-dried at 50° C. The obtained orange-red solid was purified by silica gel column chromatography (dichloromethane:acetone=50:1 (v/v)) to give a nickel (II) complex having an L-allylglycine moiety (144.9 mg, yield: 78.6%, chemical purity: 98.2%, 98.6% de) as red crystals.

ESI-MS (positive mode): m/z calcd for $C_{42}H_{33}ClN_3NiO_3$ [M+H]$^+$ 720.16. found 720.2.

$^1$H-NMR (200 MHz, CDCl$_2$): δ 2.23 (1H, ddd, J=13.9, 7.9, 5.9 Hz, one of β-CH$_2$ of allyl-Gly part), 2.39-2.53 (1H, m, one of β-CH$_2$ of allyl-Gly part), 2.65 [1H, d, J=12.1 Hz, one of azepine C(α)H$_2$N], 3.02 [1H, d, J=15.4 Hz, one of azepine C(α')H$_2$N], 3.60 and 3.69 (1H each, ABq, J=13.9 Hz, acetanilide NCOCH$_2$), 3.94 (1H, dd, J=5.9, 3.7 Hz, α-H of allyl-Gly part), 4.49 [1H, d, J=15.4 Hz, one of azepine C(α')H$_2$N], 4.76 [1H, d, J=12.1 Hz, one of azepine C(α)H$_2$N], 5.35 (1H, dd, J=17.0, 1.5 Hz), 5.74 (1H, dd, J=10.1, 1.5 Hz), 6.60-6.95 (2H, m), 6.63 (1H, d, J=2.6 Hz, ArH), 7.09-7.15 (1H, m, ArH), 7.20-7.58 (11H, m, ArH), 7.92-8.02 (3H, m, ArH), 8.14 (1H, d, J=8.2 Hz, ArH), 8.40 (1H, d, J=9.0 Hz, ArH), 8.78 (1H, d, J=8.2 Hz, ArH).

$^{13}$C-NMR (50.3 MHz, CDCl$_3$): δ 38.2 (CH$_2$), 59.2 (CH$_2$), 61.6 and 66.6 (2×CH$_2$ of azepine), 70.8 (α-CH), 120.4 (=CH$_2$), 125.1 (ArCH), 126.2 (quaternary ArC), 126.3 (quaternary ArC), 126.4 (ArCH), 127.0 (ArCH), 127.3 (ArCH), 127.4 (ArCH), 127.5 (ArCH), 127.9 (ArCH), 128.4 (ArCH), 128.5 (quaternary ArC), 128.7 (ArCH), 129.1 (ArCH), 129.3 (ArCH), 129.5 (ArCH), 130.3 (ArCH), 131.0 (quaternary ArC), 131.2 (quaternary ArC), 131.5 (quaternary ArC), 132.4 (ArCH), 132.6 (ArCH), 132.8 (quaternary ArC), 133.7 (quaternary ArC), 134.0 (quaternary ArC), 135.5 (quaternary ArC), 136.0 (quaternary ArC), 141.1 (quaternary ArC), 170.0, 174.3, 177.6 (CN and 2×CO).

Figure 10:
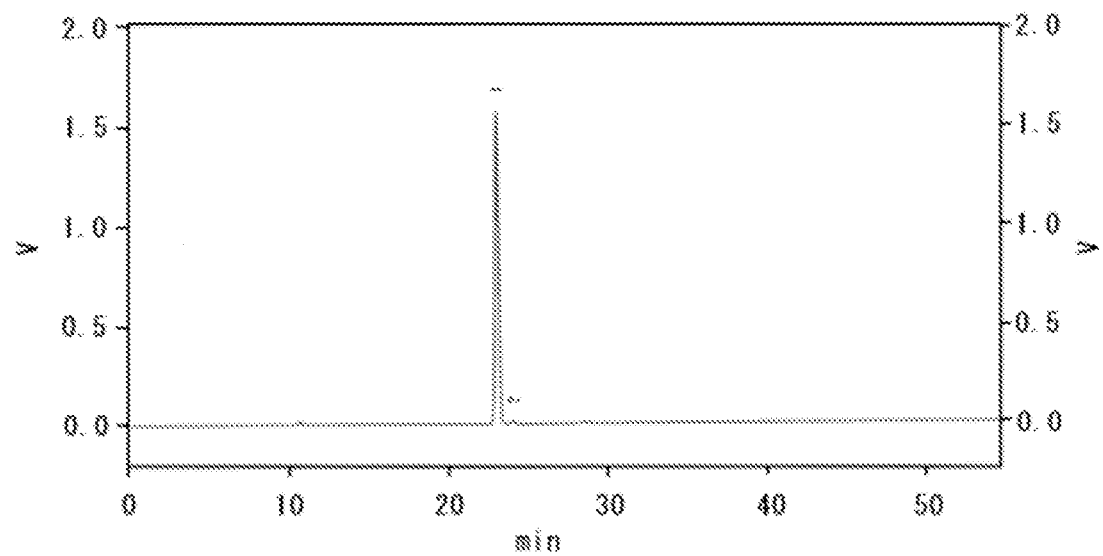
FIG. 10 shows a HPLC chromatogram of the compound prepared in Example 2-8.

HPLC analysis was conducted on the obtained compound under the above <HPLC conditions-1: complex analysis conditions>. The results are shown in Table 10 and FIG. 10.

<HPLC Conditions-1: Complex Analysis Conditions>

TABLE 10

| Retention time in HPLC (min) | | Excess ratio (objective substance:isomer of objective substance) |
|---|---|---|
| Objective substance | Isomer of objective substance | |
| 23.08 | 24.04 | 98.6% de (99.3:0.7) |

Example 2-9: Release of L-allylglycine from Nickel (II) Complex Having L-allylglycine Moiety Under Acidic Conditions and Protection of L-allylglycine with Boc Group Under an argon atmosphere, to a suspension of a nickel (II) complex having an L-allylglycine moiety (107.6 mg, 0.149 mmol) in methanol (3.3 mL), 1 N hydrochloric acid (0.75 mL, 0.75 mmol) was added, and the mixture was stirred at 40° C. for 2 hours. After the end of the reaction, the reaction mixture was concentrated, and the residue was subjected to phase separation with dichloromethane (10 mL) and water (10 mL). The aqueous layer was separated, and the solvent was removed by evaporation. The obtained solid was dissolved in 4% aqueous ammonia (3 mL). The solution was passed through a cation exchange resin column [SK-1B, 18 mL, eluent: water and subsequently 2 to 4% aqueous ammonia] to give quantitatively L-allylglycine (18.9 mg, 96.9% ee).

Figure 11:
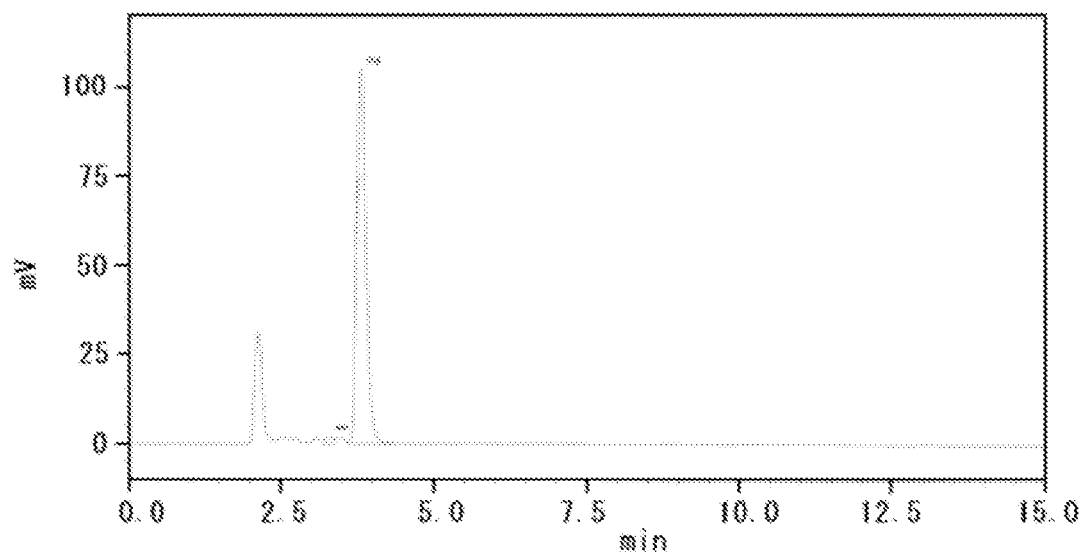
FIG. 11 shows a HPLC chromatogram of the compound prepared in Example 2-9.

HPLC analysis was conducted on the obtained compound under the following conditions. The results are shown in Table 11 and FIG. 11.

<HPLC Conditions: L-allylglycine Chiral Analysis Conditions>
Column: CROWNPAK CR(+) (5 μm, 150×4.0 mm i.d.)
Eluent: perchloric acid aqueous solution (pH 2.0)
Flow rate: 0.5 mL/min

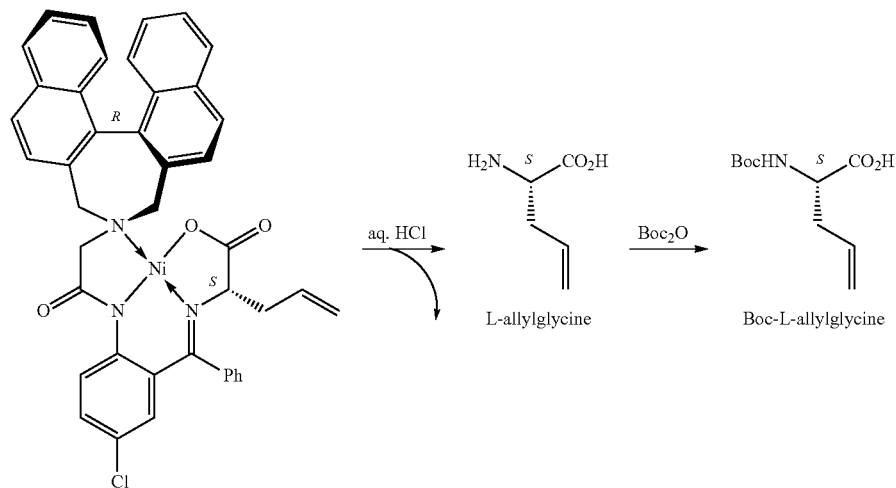

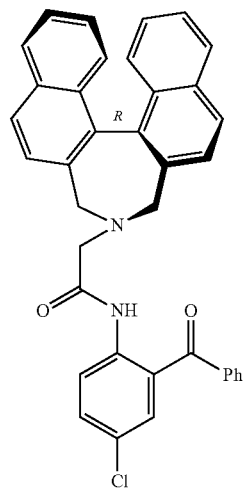

Temperature: 20° C.
Detector: UV 200 nm

TABLE 11

| Retention time in HPLC (min) | | Excess ratio (isomer of objective substance:objective substance) |
|---|---|---|
| D-allylglycine | L-allylglycine | |
| 3.29 | 3.80 | 96.9% ee (1.56:98.44) |

Meanwhile, the organic layer was washed with 2% aqueous ammonia (10 mL, twice), with water (10 mL, twice), and then with saturated brine (10 mL, twice). The organic layer was dried over sodium sulfate, and then the solvent was removed by evaporation to give quantitatively a chiral auxiliary (R-isomer) (94.2 mg, chemical purity: 98.1%).

L-allylglycine (17.7 mg, 0.154 mmol) was dissolved in water (2 mL) and acetone (1.0 mL). To the solution, a solution of $(Boc)_2O$ (36.9 mg, 0.169 mmol) in acetone (0.5 mL) and a solution of triethylamine (17.1 mg, 0.169 mmol) in acetone (0.5 mL) were added. The mixture was stirred at room temperature for 22 hours. The reaction mixture was concentrated until the volume was reduced to 2 mL or less, and then toluene (5 mL) was added thereto. To this, 1 N hydrochloric acid was added under stirring until the pH of the aqueous layer was reduced to 2 to 3. The aqueous layer was extracted with toluene (5 mL, 3 times). The organic layers were combined and washed with saturated brine (5 mL, twice) and dried over magnesium sulfate, and then the solvent was removed by evaporation. The concentrated residue was purified by silica gel column chromatography (dichloromethane-methanol) to give Boc-L-allylglycine (18.7 mg, 56.5%, chemical purity: 95.5%) as a colorless oily substance.

HPLC analysis was conducted on the obtained compound under the following conditions. The results are shown in Table 12.

<HPLC Conditions: Boc-L-allylglycine Analysis Conditions>

Column: Inertsil ODS-3 (3 μm, 150×4.6 mm i.d.)
Eluent: A:B=80:20 to 20:80 (0 to 25 min)
  A=10 mM ammonium formate in 0.1% formic acid buffer solution
  B=acetonitrile
Flow rate: 1.0 mL/min
Temperature: 30° C.
Detector: UV 200 nm

TABLE 12

| Retention time in HPLC (min) Boc-L-allylglycine | Chemical purity |
|---|---|
| 12.48 | 95.5% |

Example 3

Synthesis of Optically Active α,α-disubstituted α-amino Acid

Reference Example 1

Synthesis of Nickel (II) Complex Having Alanine Moiety

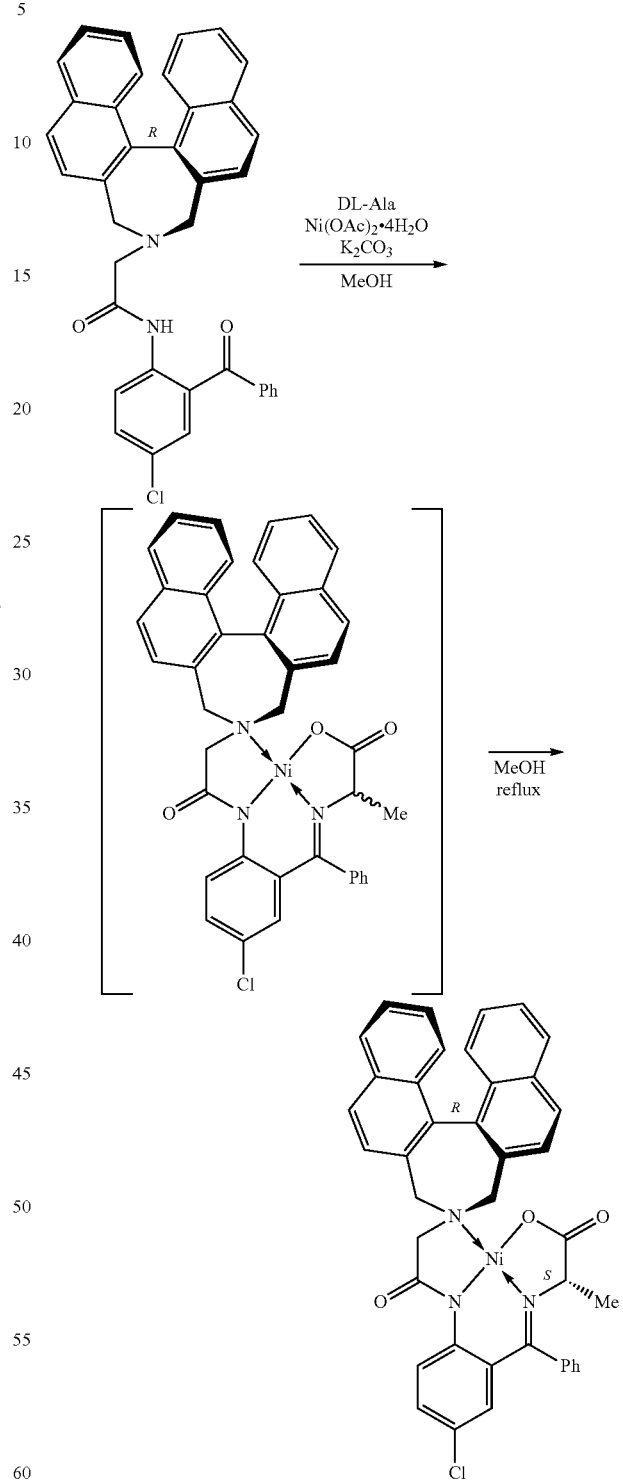

To a methanol suspension (4 mL) of a chiral auxiliary (R-isomer) (0.2 g, 0.353 mmol), nickel acetate tetrahydrate (0.176 g, 0.706 mmol), DL-alanine (0.063 g, 0.706 mmol), and potassium carbonate (0.293 g, 2.118 mmol) were added. The mixture was heated at 40° C. for 24 hours. After the end of the reaction, the reaction mixture was added to an ice-cooled 5% acetic acid aqueous solution (30 mL), and the whole was stirred for 30 minutes to allow crystals to precipitate. The crystals were separated by filtration, and then blow-dried at 50° C. to give a nickel (II) complex having an alanine moiety (0.207 g, yield: 84.8%, 96% de) as red crystals.

ESI-MS (positive mode): m/z=694.2 for [M+H]'.

$^1$H-NMR (200 MHz, CDCl$_2$): δ 1.51 (3H, d, J=7.0 Hz, Me), 2.73 [1H, d, J=12.2 Hz, one of azepine C(α)H$_2$N], 3.08 [1H, d, J=15.6 Hz, one of azepine C(α')H$_2$N], 3.68 and 3.76 (1H each, ABq, J=13.9 Hz, acetanilide NCOCH$_2$), 3.84 (1H, q, J=7.0 Hz, α-H of Ala part), 4.57 [1H, d, J=15.6 Hz, one of azepine C(α')H$_2$N], 4.84 [1H, d, J=12.1 Hz, one of azepine C(α)H$_2$N], 6.66 (1H, d, J=2.6 Hz), 6.91-6.99 (1H, m, ArH), 7.16-7.32 (4H, m, ArH), 7.35-7.41 (1H, m, ArH), 7.43-7.57 (7H, m, ArH), 7.94-8.03 (3H, m, ArH), 8.16 (1H, d, J=8.3 Hz, ArH), 8.44 (1H, d, J=9.2 Hz, ArH), 8.76 (1H, d, J=8.3 Hz, ArH).

$^{13}$C-NMR (50.3 MHz, CDCl$_3$): δ 21.5 (Me of Ala part), 58.7 (NCOCH$_2$), 61.9 and 66.3 (2×CH$_2$ of azepine), 66.9 (α-CH of Ala part), 125.1 (ArCH), 126.1 (quaternary ArC), 126.37 (quaternary ArC), 126.44 (ArCH), 126.9 (ArCH), 127.3 (ArCH), 127.4 (ArCH), 127.5 (ArCH), 127.6 (ArCH), 127.8 (ArCH), 128.2 (quaternary ArC), 128.4 (ArCH), 128.7 (ArCH), 129.2 (ArCH), 129.5 (ArCH), 130.2 (ArCH), 131.0 (quaternary ArC), 131.3 (quaternary ArC), 131.5 (quaternary ArC), 132.4 (ArCH), 132.6 (ArCH), 132.7 (quaternary ArC), 133.7 (quaternary ArC), 134.1 (quaternary ArC), 135.6 (quaternary ArC), 136.0 (quaternary ArC), 140.9 (quaternary ArC), 170.2, 174.6, 179.7 (CN and 2×CO).

Example 3-1: Synthesis of Nickel (II) Complex Having α-methyl-L-phenylalanine Moiety by Reaction of Nickel (II) Complex Having Alanine Moiety and Benzyl Bromide

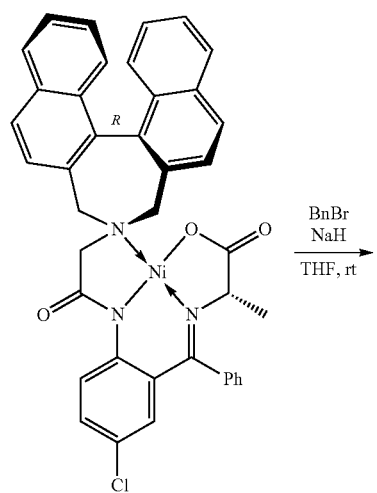

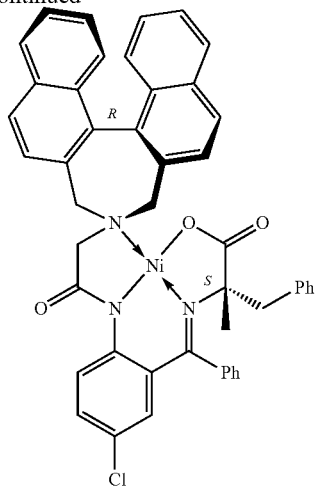

Under an argon atmosphere, to a tetrahydrofuran (THF) solution (5.2 mL) of a nickel (II) complex having an alanine moiety (258.6 mg, 0.372 mmol), benzyl bromide (70.0 mg, 0.409 mmol) and sodium hydride (26.8 mg, 1.117 mmol) were sequentially added. The mixture was stirred at room temperature (23 to 24° C.) for 2.0 hours. To the reaction mixture, water (10 mL) and ethyl acetate (10 mL) were added, and the whole was stirred. After phase separation, the aqueous layer was extracted with ethyl acetate (10 mL) 3 times. The organic layers were combined and washed with saturated brine (15 mL) and dried over sodium sulfate (10 g). The solvent was removed by evaporation to give an orange-red solid (302.8 mg). The obtained orange-red solid (302.8 mg) was subjected to recrystallization from dichloromethane-ethyl acetate (1:1, 10 v/w) to give a nickel (II) complex having an α-methyl-L-phenylalanine moiety (215.6 mg, yield: 73.8%, chemical purity: 99.4%, >99.9% de) as red crystals.

ESI-MS (positive mode): m/z calcd for C$_{47}$H$_{37}$ClN$_3$NiO$_3$ [M+H]$^+$ 784.19. found 784.2.

$^1$H-NMR (200 MHz, CDCl$_3$): δ 1.01 (3H, s, α-Me), 2.46 [1H, d, J=12.1 Hz, one of azepine C(α)H$_2$N], 2.57 [1H, d, J=15.5 Hz, one of azepine C (α')H$_2$N], 2.71 (1H, d, J=13.9 Hz, one of α-MePhe β-CH$_2$), 2.97 and 3.03 (1H each, ABq, J=13.6 Hz, acetanilide NCOCH$_2$), 3.27 (1H, d, J=13.9 Hz, one of α-MePhe β-CH$_2$), 3.52 [1H, d, J=15.5 Hz, one of azepine C(α')H$_2$N], 4.55 [1H, d, J=12.1 Hz, one of azepine C(α)H$_2$N], 6.73 (1H, d, J=2.4 Hz), 7.12-7.36 (7H, m, ArH), 7.40-7.62 (8H, m, ArH), 7.67-7.86 (3H, m, ArH), 7.87-7.98 (3H, m, ArH), 8.07 (1H, d, J=8.2 Hz, ArH), 8.23 (1H, d, J=9.2 Hz, ArH), 8.63 (1H, d, J=8.2 Hz, ArH).

$^{13}$C-NMR (50.3 MHz, CDCl$_3$): δ 29.2 (Me), 47.4 (β-CH$_2$), 57.6 (NCOCH$_2$), 61.7 and 65.6 (2×CH$_2$ of azepine), 80.4 (quaternary), 124.8 (ArCH), 125.8 (quaternary ArC), 126.3 (ArCH), 126.5 (ArCH), 127.2 (ArCH), 127.4 (ArCH), 127.6 (ArCH), 127.9 (ArCH), 128.37 (ArCH), 128.44 (ArCH), 128.7 (ArCH), 128.9 (ArCH), 129.0 (ArCH), 129.3 (ArCH), 129.9 (ArCH), 131.1 (quaternary ArC), 130.3 (ArCH), 131.1 (quaternary ArC), 131.4 (quaternary ArC), 131.7 (ArCH), 132.3 (ArCH), 132.9 (ArCH), 133.5 (quaternary ArC), 133.8 (quaternary ArC), 135.3 (quaternary ArC), 135.8 (quaternary ArC), 136.0 (quaternary ArC), 137.6 (quaternary ArC), 140.6 (quaternary ArC), 170.9, 174.1, 179.4 (CN and 2×CO).

Figure 12:
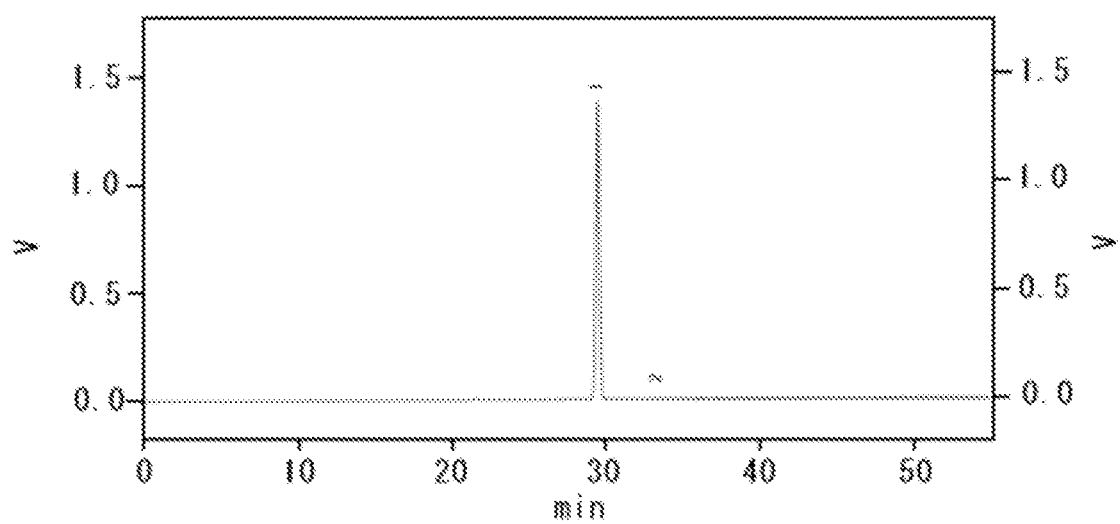
FIG. 12 shows a HPLC chromatogram of the compound prepared in Example 3-1.

HPLC analysis was conducted on the obtained compound under the above <HPLC conditions-1: complex analysis conditions>. The results are shown in Table 13 and FIG. 12.

TABLE 13

| | Retention time in HPLC (min) | |
|---|---|---|
| Objective substance | Isomer of objective substance | Excess ratio (objective substance:isomer of objective substance) |
| 29.56 | 33.06 | >99.9% de (99.98:0.02) |

Example 3-2: Release of α-methyl-L-phenylalanine from Nickel (II) Complex Having α-methyl-L-phenylalanine Moiety Under Acidic Conditions and Protection of α-methyl-L-phenylalanine with Boc Group

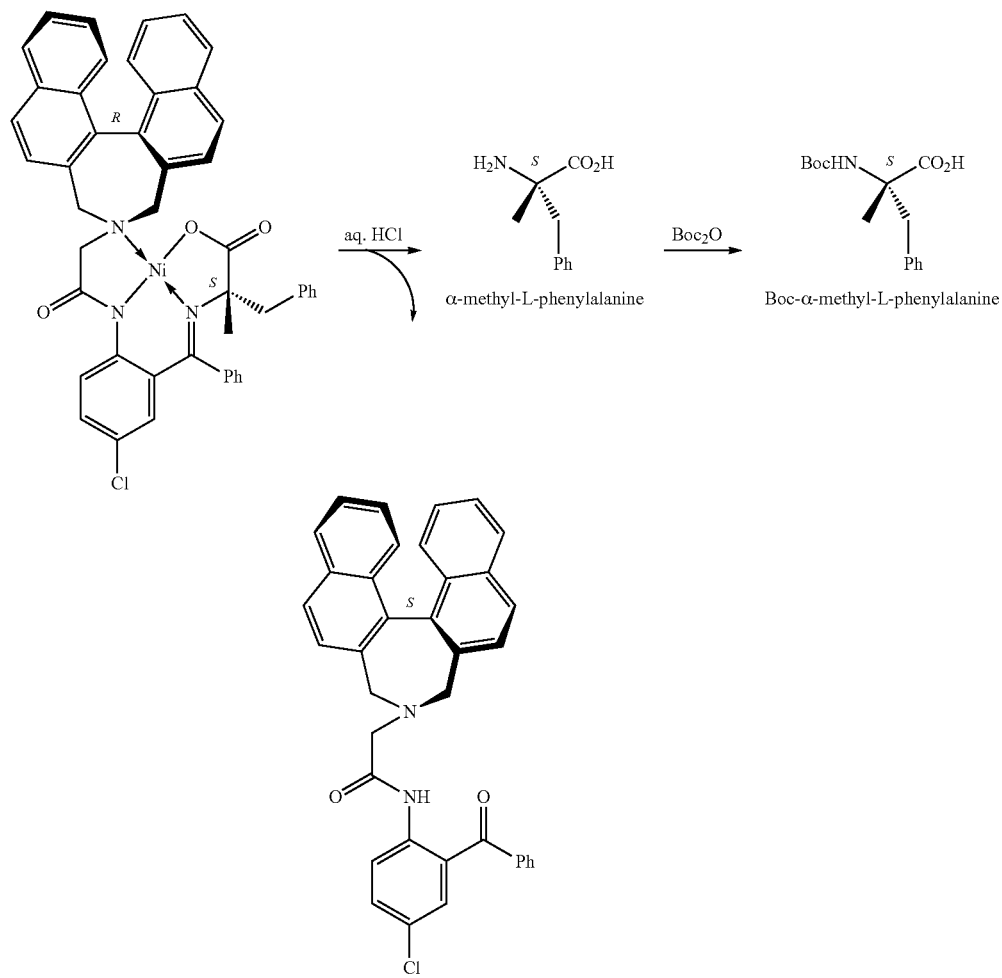

To a suspension of a nickel (II) complex having an α-methyl-L-phenylalanine moiety (190.0 mg, 0.242 mmol) in methanol (5.7 mL), 1 N hydrochloric acid (1.2 mL, 1.20 mmol, 5 eq.) was added, and the mixture was stirred at 40 to 50° C. for 5 hours. The reaction mixture was concentrated under reduced pressure, and the residue was dissolved in dichloromethane (10 mL) and water (10 mL). After phase separation, the organic layer was washed with 2% aqueous ammonia (10 mL, twice), with water (10 mL, twice), and then with saturated brine (10 mL, twice). The organic layer was dried over sodium sulfate, and then the solvent was removed by evaporation to give quantitatively a chiral auxiliary (R-isomer) (138.2 mg, chemical purity: 92.2%).

Meanwhile, the aqueous layer was concentrated to dryness, and the resulting solid was dissolved in a mixed solvent of 8% aqueous ammonia (0.5 mL) and methanol (5.0 mL). The solution was passed through a cation exchange resin column [SK-1B, 40 mL, eluent: water and subsequently 4% aqueous ammonia] to give α-methyl-L-phenylalanine (25.6 mg, yield: 59.0%) as a white solid. The obtained α-methyl-L-phenylalanine (20.0 mg, 0.112 mmol) was suspended in anhydrous acetonitrile (1.0 mL). To the suspension, tetramethylammonium hydroxide pentahydrate (20.2 mg, 0.112 mmol) was added, and the mixture was stirred at room temperature for 1 hour. To this, $(Boc)_2O$ (36.5 mg, 0.167 mmol) was added, and the mixture was stirred at room temperature for 76 hours. The reaction mixture was concentrated, and the residue was dissolved in water (5 mL). The solution was washed with isopropyl ether (2 mL) twice. To the aqueous layer, citric acid was added to adjust the pH to 3, and then this was extracted with ethyl acetate (10 mL) 3 times. The organic layers were combined and washed with water (5 mL, twice) and with saturated brine (5 mL, twice), and dried over magnesium sulfate. The solvent was removed by evaporation to give Boc-α-methyl-L-phenylalanine (29.3 mg, 55.5%, chemical purity: 91.3%, 99.6% ee) as a colorless oily substance.

Figure 13:
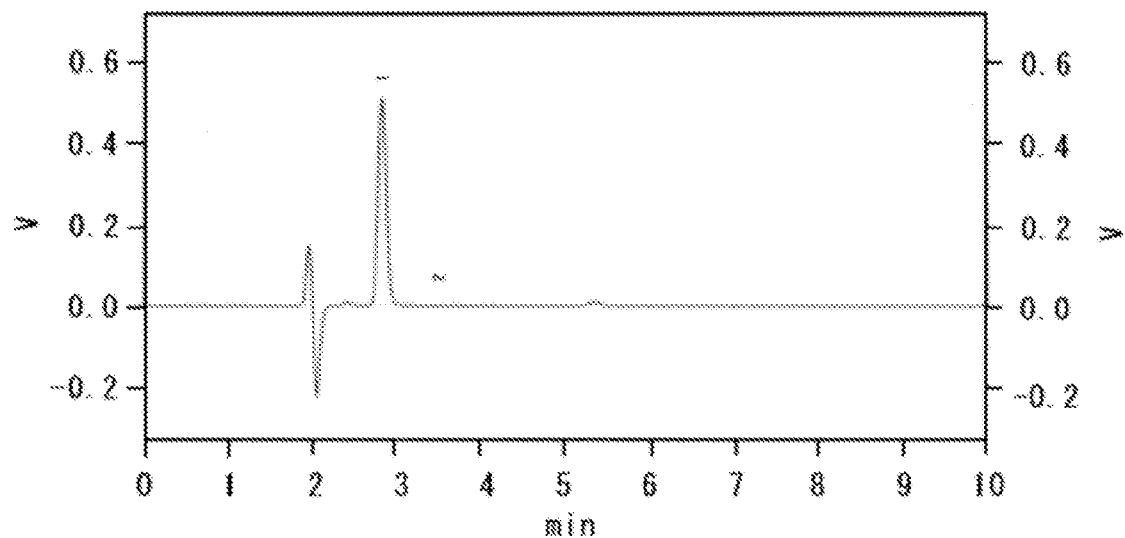
FIG. 13 shows a HPLC chromatogram of the compound prepared in Example 3-2.

HPLC analysis was conducted on the obtained compound under the following conditions. The results are shown in Table 14 and FIG. 13.
<HPLC Conditions: Boc-α-methyl-L-phenylalanine Chiral Analysis Conditions>
Column: CHIRALPAK AY-H (5 μm, 150×4.6 mm i.d.)
Eluent: hexane/ethanol=92.5/7.5, 0.3% trifluoroacetic acid
Flow rate: 1.0 mL/min
Temperature: 40° C.
Detector: UV 220 nm

TABLE 14

| Retention time in HPLC (min) | | |
|---|---|---|
| Objective substance Boc-α-methyl-L-phenylalanine | Isomer of objective substance Boc-α-methyl-D-phenylalanine | Excess ratio (objective substance:isomer of objective substance) |
| 2.8 | 3.6 | 99.6% ee (99.8:0.2) |

Example 3-3: Synthesis of Nickel (II) Complex Having 4-fluoro-α-methyl-L-phenylalanine Moiety by Reaction of Nickel (II) Complex Having Alanine Moiety and 4-fluorobenzyl bromide

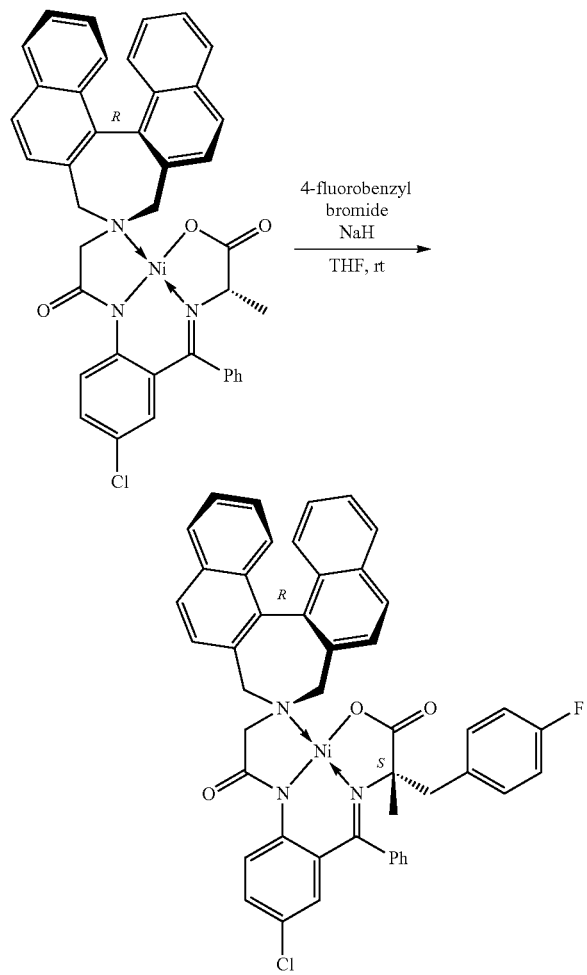

Under an argon atmosphere, to a tetrahydrofuran (THF) solution (4 mL) of a nickel (II) complex having an alanine moiety (200.0 mg, 0.288 mmol), 4-fluorobenzyl bromide (59.9 mg, 0.317 mmol) and sodium hydride (20.8 mg, 0.864 mmol) were sequentially added. The mixture was stirred at room temperature (23° C.) for 2 hours. To the reaction mixture, water (10 mL) and ethyl acetate (10 mL) were added, and the whole was stirred. After phase separation, the aqueous layer was extracted with ethyl acetate (10 mL) 3 times. The organic layers were combined and washed with saturated brine and dried over sodium sulfate. The solvent was removed by evaporation, and the resulting orange-red solid (225.0 mg) was purified by silica gel column chromatography (dichloromethane:acetone=50:1 (v/v)). Subsequently, recrystallization from dichloromethane-methanol (1:5, 16 v/w) was performed to give a nickel (II) complex having a 4-fluoro-α-methyl-L-phenylalanine moiety (107.4 mg, yield: 46.5%, chemical purity: 99.7%, >99.9% de) as red crystals.

ESI-MS (positive mode): m/z calcd for $C_{47}H_{36}ClFN_3NiO_3$ [M+H]$^+$ 802.18. found 802.3.

$^1$H-NMR (200 MHz, CDCl$_3$): δ 1.02 (3H, s, α-Me), 2.54 [1H, d, J=12.1 Hz, one of azepine C(α)H$_2$N], 2.690 [1H, d, J=15.6 Hz, one of azepine C(α')H$_2$N], 2.694 (1H, d, J=13.7 Hz, one of α-Me-4-fluoroPhe β-CH$_2$), 2.96 and 2.99 (1H each, ABq, J=13.8 Hz, acetanilide NCOCH$_2$), 3.32 (1H, d, J=13.7 Hz, one of α-Me-4-fluoroPhe β-CH$_2$), 3.59 [1H, d, J=15.6 Hz, one of azepine C(α')H$_2$N], 4.62 [1H, d, J=12.1 Hz, one of azepine C(α)H$_2$N], 6.76 (1H, d, J=2.6 Hz, ArH), 7.09-7.15 (1H, m, ArH), 7.18-7.59 (16H, m, ArH), 7.88-8.01 (3H, m, ArH), 8.06 (1H, d, J=8.2 Hz, ArH), 8.26 (1H, d, J=9.2 Hz, ArH), 8.57 (1H, d, J=8.2 Hz, ArH).

$^{13}$C-NMR (50.3 MHz, CDCl$_3$): δ 29.2 (Me), 46.5 (β-CH$_2$), 58.1 (NCOCH$_2$), 61.9 and 65.7 (2×CH$_2$ of azepine), 80.3 (quaternary), 115.8 (d, $^3J_{CF}$=22.0 Hz), 124.9 (ArCH), 126.0 (quaternary ArC), 126.3 (ArCH), 126.4 (ArCH), 126.5 (ArCH), 127.3 (ArCH), 127.5 (ArCH), 127.7 (ArCH), 127.8 (ArCH), 128.4 (ArCH), 128.7 (quaternary ArC), 128.8 (ArCH), 129.2 (ArCH), 129.4 (ArCH), 130.0 (quaternary ArC), 130.2 (d, $^4J_{CF}$=14.6 Hz), 131.1 (quaternary ArC), 131.2 (quaternary ArC), 131.4 (quaternary ArC), 132.4 (ArCH), 132.9 (ArCH), 133.1 (ArCH), 133.2 (ArCH), 133.3 (quaternary ArC), 133.6 (quaternary ArC), 133.9 (quaternary ArC), 135.2 (quaternary ArC), 135.8 (quaternary ArC), 136.0 (quaternary ArC), 140.6 (quaternary ArC), 162.9 (d, $^1J_{CF}$=247.1 Hz), 171.2, 174.1, 179.3 (CN and 2×CO).

Figure 14:
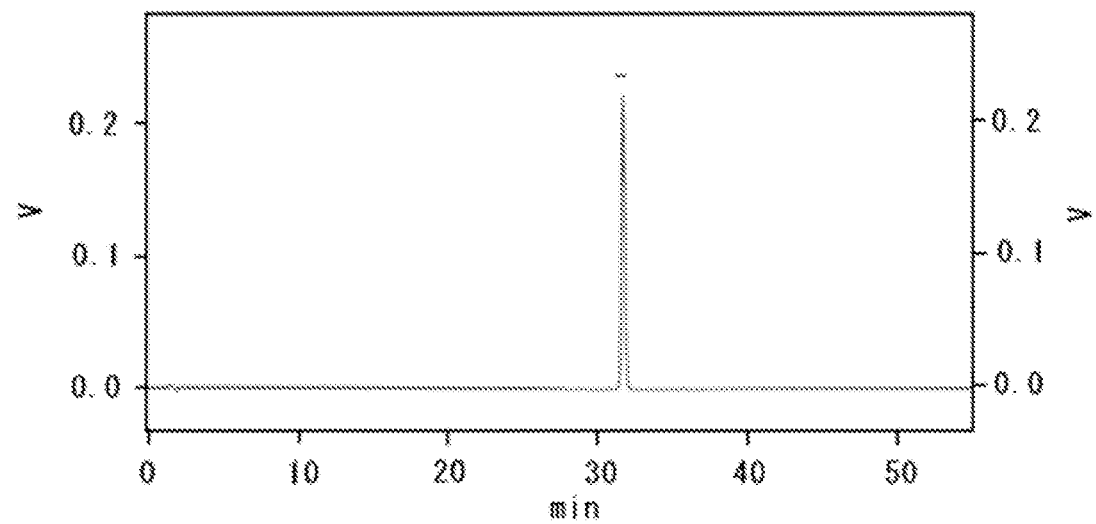
FIG. 14 shows a HPLC chromatogram of the compound prepared in Example 3-3.

HPLC analysis was conducted on the obtained compound under the above <HPLC conditions-1: complex analysis conditions>. The results are shown in Table 15 and FIG. 14.

TABLE 15

| Retention time in HPLC (min) | | |
|---|---|---|
| Objective substance | Isomer of objective substance | Excess ratio (objective substance:isomer of objective substance) |
| 31.7 | 35.29 | >99.9% de |

Example 3-4: Synthesis of Nickel (II) Complex Having (S)-α-allylalanine Moiety by Reaction of Nickel (II) Complex Having Alanine Moiety and Allyl Bromide

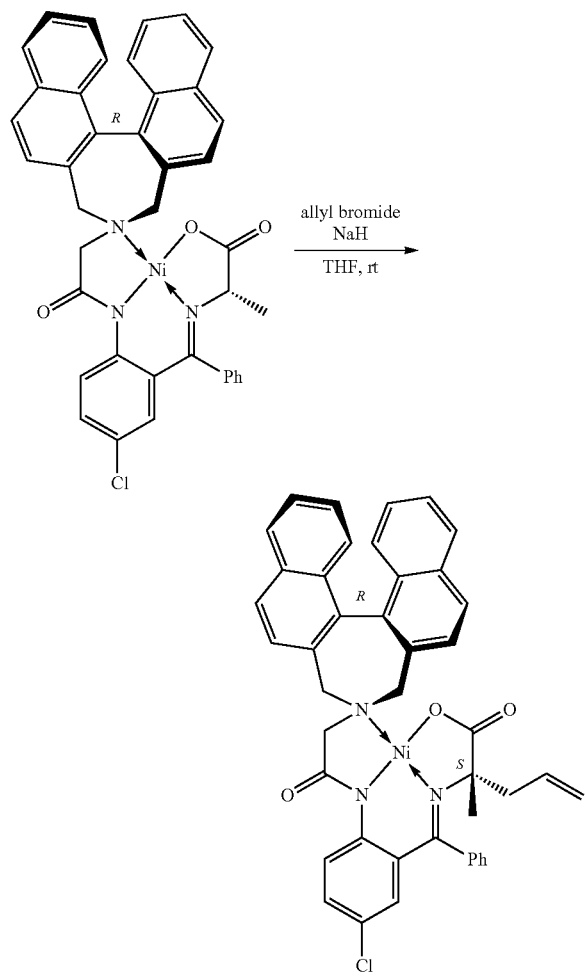

Under an argon atmosphere, to a tetrahydrofuran (THF) solution (10 mL) of a nickel (II) complex having an alanine moiety (500.0 mg, 0.720 mmol), allyl bromide (95.8 mg, 0.792 mmol) and sodium hydride (51.8 mg, 2.129 mmol) were sequentially added. The mixture was stirred at room temperature (23° C.) for 1 hour. The reaction mixture was subjected to phase separation with water (20 mL) and ethyl acetate (20 mL), and the aqueous layer was extracted with ethyl acetate (10 mL) 3 times. The organic layers were combined and washed with saturated brine, dried over sodium sulfate (7 g), and then concentrated to dryness. The obtained crude product (528.5 mg) was subjected to recrystallization from dichloromethane-ethyl acetate (1:1.5) to give a nickel (II) complex having an (S)-α-allylalanine moiety (346.3 mg, yield: 65.5%, chemical purity: 96.8%, 98.7% de) as red crystals.

ESI-MS (positive mode): m/z calcd for $C_{43}H_{35}ClN_3NiO_3$ [M+H]$^+$ 734.17. found 734.0.

$^1$H-NMR (200 MHz, CDCl$_3$): δ 1.01 (3H, s, α-Me), 2.45 (1H, H$_A$ of ABX type, J$_{AB}$=13.9 Hz, J$_{AX}$=7.3 Hz, one of β-CH$_2$ of allyl-Ala part), 2.53 (1H, H$_B$ of ABX type, J$_{AB}$=13.9 Hz, J$_{BX}$=7.1 Hz, one of β-CH$_2$ of allyl-Ala part), 2.76 [1H, d, J=12.1 Hz, one of azepine C(α)H$_2$N], 3.12 [1H, d, J=15.4 Hz, one of azepine C(α')H$_2$N], 3.55 and 3.80 (1H each, ABq, J=13.9 Hz, acetanilide NCOCH$_2$), 4.38 [1H, d, J=15.4 Hz, one of azepine C(α')H$_2$N], 4.79 [1H, d, J=12.1 Hz, one of azepine C(α)H$_2$N], 5.49 (1H, dd, J=17.0, 1.5 Hz), 5.79 (1H, dd, J=10.1, 1.5 Hz), 6.75 (1H, d, J=2.4 Hz, ArH), 6.88-7.10 (2H, m), 7.20-7.57 (12H, m, ArH), 7.92-8.03 (3H, m, ArH), 8.11 (1H, d, J=8.2 Hz, ArH), 8.30 (1H, d, J=9.0 Hz, ArH), 8.67 (1H, d, J=8.2 Hz, ArH).

$^{13}$C-NMR (50.3 MHz, CDCl$_3$): δ 28.6 (Me), 45.3 (CH$_2$), 59.0 (CH$_2$), 61.5 and 66.0 (2×CH$_2$ of azepine), 78.9 (quaternary), 120.1 (=CH$_2$), 124.8 (ArCH), 126.0 (quaternary ArC), 126.2 (ArCH), 126.4 (ArCH), 126.8 (ArCH), 127.46 (ArCH), 127.53 (ArCH), 128.0 (ArCH), 128.4 (ArCH), 128.5 (ArCH), 128.7 (quaternary ArC), 129.1 (ArCH), 129.4 (ArCH), 129.8 (ArCH), 129.9 (ArCH), 130.4 (quaternary ArC), 131.17 (quaternary ArC), 131.24 (quaternary ArC), 131.4 (quaternary ArC), 132.2 (ArCH), 132.7 (ArCH), 133.6 (ArCH), 133.9 (quaternary ArC), 135.5 (quaternary ArC), 135.6 (quaternary ArC), 136.0 (quaternary ArC), 140.3 (quaternary ArC), 171.2, 174.1, 180.1 (CN and 2×CO).

Figure 15:
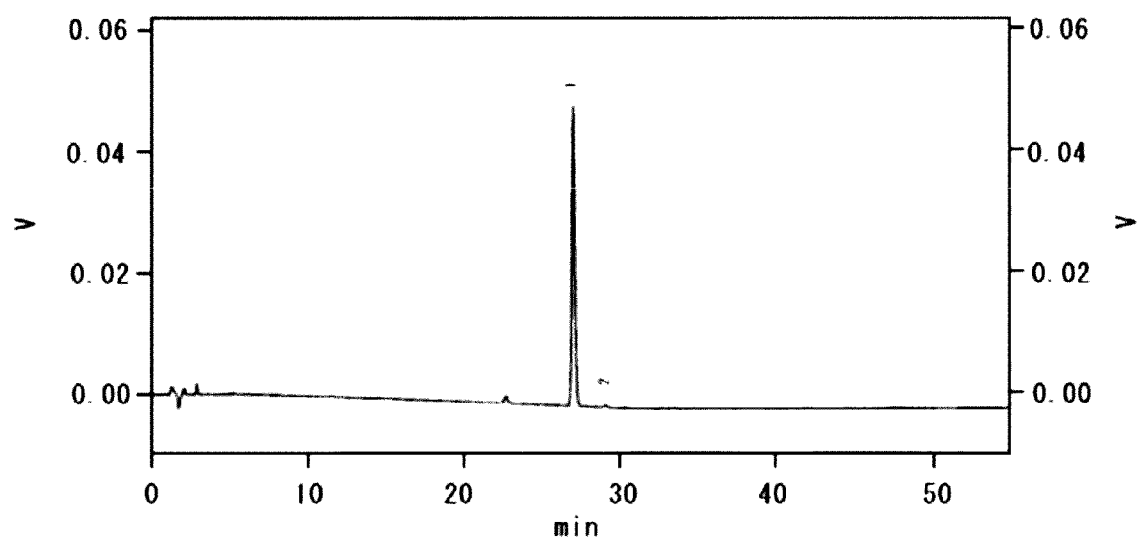
FIG. 15 shows a HPLC chromatogram of the compound prepared in Example 3-4.

HPLC analysis was conducted on the obtained compound under the above <HPLC conditions-1: complex analysis conditions>. The results are shown in Table 16 and FIG. 15.

TABLE 16

| Retention time in HPLC (min) | | |
|---|---|---|
| Objective substance | Isomer of objective substance | Excess ratio (objective substance:isomer of objective substance) |
| 27.06 | 29.10 | 98.7% de (99.36:0.64) |

Example 4

Aldol Reaction of Chiral Glycine Equivalent and Carbonyl Compound and Synthesis of Optically Active Amino Acid

Example 4-1: Synthesis of Nickel (II) Complex Having D-threo-3-phenylserine Moiety by Aldol Reaction of Chiral Glycine Equivalent and Benzaldehyde

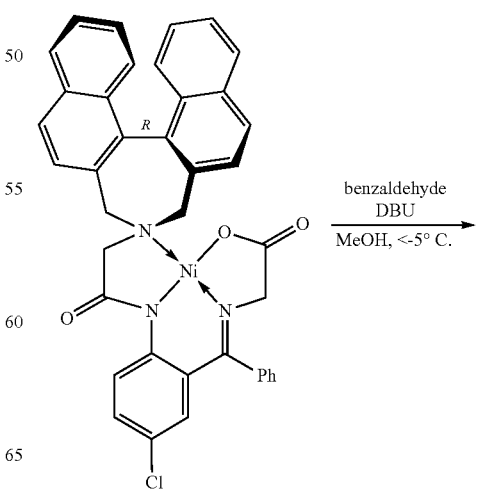

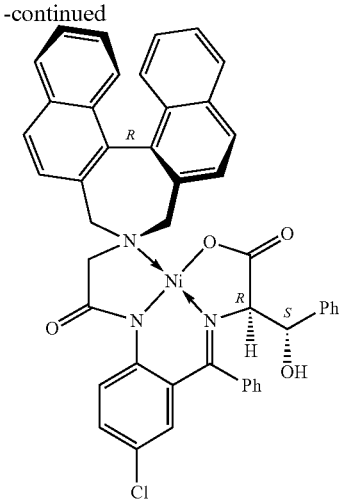

To a methanol solution (25 mL) of a chiral glycine equivalent (R-isomer) (500 mg, 0.734 mmol), benzaldehyde (0.38 mL, 3.67 mmol) was added, and the mixture was stirred at −5° C. or lower for 10 minutes. To this, DBU (0.33 mL, 2.20 mmol) was added dropwise, and the mixture was stirred at −5° C. or lower for 2 hours. The reaction mixture was added to an ice-cooled 5% acetic acid aqueous solution (25 mL), and the whole was stirred for 30 minutes. The precipitated crystals were separated by filtration, and then blow-dried at 50° C. to give a red solid (555 mg, 82% de, containing 8.7% chiral glycine equivalent (R-isomer)). The obtained red solid was purified by silica gel column chromatography (dichloromethane:acetone=97:3 (v/v)), and then recrystallization was performed to give a nickel (II) complex having a D-threo-3-phenylserine moiety (150 mg, yield: 26%) as red crystals.

ESI-MS (positive mode): m/z=786.2 for [M+H]$^+$ $^1$H-NMR (200 MHz, CDCl$_3$): δ 2.27 [1H, d, J=12.3 Hz, one of azepine C(α)H$_2$N], 2.88 [1H, d, J=15.7 Hz, one of azepine C(α')H$_2$N], 3.23 [1H, dd, J=15.7, 1.3 Hz, one of azepine C(α')H$_2$N], 3.39 [1H, d, J=12.3 Hz, one of azepine C(α)H$_2$N], 3.81 (1H, d, J=13.4 Hz, one of acetanilide NCOCH$_2$), 4.20 (1H, dd, J=13.4, 1.3 Hz, one of acetanilide NCOCH$_2$), 4.28 (1H, d, J=5.5 Hz, α-H of AA part), 4.62 (1H, dd, J=9.7, 5.5 Hz, (3-H of AA part), 5.09 (1H, d, J=9.7 Hz, OH), 6.70 (1H, d, J=2.6 Hz), 7.03-7.10 (1H, m, ArH), 7.16-7.82 (18H, m, ArH), 7.87-8.00 (4H, m, ArH), 8.63 (1H, d, J=9.3 Hz, ArH).

$^{13}$C-NMR (50.3 MHz, CDCl$_3$): δ 57.7 (CH$_2$), 58.9 (CH$_2$), 61.5 (CH$_2$), 73.2 (CH), 73.4 (CH), 124.9 (ArCH), 125.7 (ArCH), 126.1 (ArCH), 126.4 (ArCH), 126.6 (ArCH), 126.7 (ArCH), 127.2 (ArCH), 127.5 (ArCH), 127.7 (ArCH), 127.9 (quaternary ArC), 128.15 (ArCH), 128.22 (ArCH), 128.3 (ArCH), 128.7 (ArCH), 128.9 (ArCH), 129.1 (ArCH), 129.7 (ArCH), 130.8 (ArCH), 130.9 (quaternary ArC), 131.2 (ArCH), 131.4 (quaternary ArC), 132.6 (quaternary ArC), 132.7 (ArCH), 133.1 (ArCH), 133.6 (quaternary ArC), 133.7 (quaternary ArC), 134.6 (quaternary ArC), 135.7 (quaternary ArC), 140.2 (quaternary ArC), 141.4 (quaternary ArC), 171.6, 174.0, 177.6 (CN and 2×CO).

Example 4-2: Synthesis of D-threo-3-phenylserine from Nickel (II) Complex Having D-threo-3-phenylserine Moiety Under Acidic Conditions

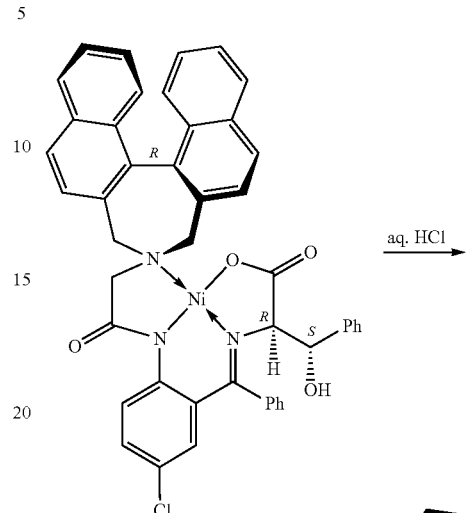

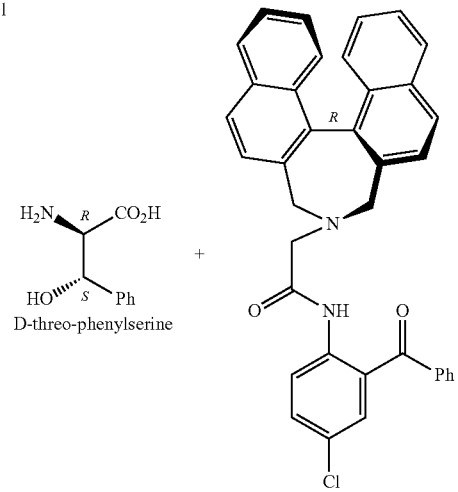

To a suspension of a nickel (II) complex having a D-threo-3-phenylserine moiety (100 mg, 0.127 mmol) in methanol (3 mL), 1N hydrochloric acid (0.64 mL, 0.635 mmol) was added, and the mixture was stirred at 50° C. for 4 hours. The reaction mixture was concentrated under reduced pressure, and the residue was subjected to phase separation with dichloromethane (10 mL) and water (10 mL). The aqueous layer was separated, and the solvent was removed by evaporation. The obtained solid was dissolved in 9% aqueous ammonia (3 mL). The solution was passed through a cation exchange resin column [SK-1B, 18 mL, eluent: 2 to 4% aqueous ammonia] to give D-threo-3-phenylserine (15 mg, 0.083 mmol, yield: 65%, 99.4% ee). Meanwhile, the organic layer was washed with 4% aqueous ammonia (10 mL), with water (10 mL), and then with saturated brine (10 mL). The organic layer was dried over sodium sulfate, and then the solvent was removed by evaporation to give a chiral auxiliary (R-isomer) (49 mg, 0.086 mmol, yield: 68%).

Figure 16:
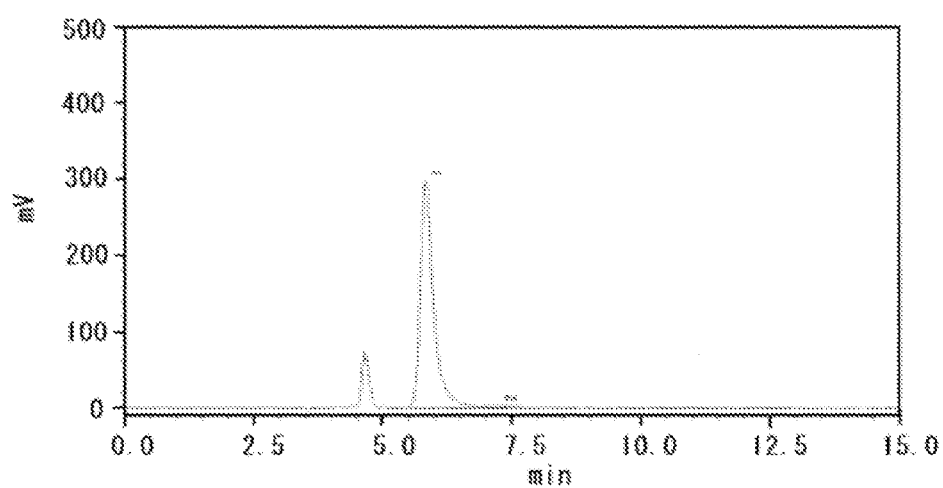
FIG. 16 shows a HPLC chromatogram of the compound prepared in Example 4-2.

HPLC analysis was conducted on the obtained compound under the following conditions. The results are shown in Table 17 and FIG. 16.

<HPLC Conditions: D-threo-3-phenylserine Chiral Analysis Conditions>
Column: TSKgel Enantio L1 (5 μm, 250×4.6 mm i.d.)
Eluent: 2 mM copper sulfate aqueous solution (analysis time: 15 min)

Flow rate: 0.8 mL/min
Temperature: 35° C.
Detector: UV 230 nm

TABLE 17

| | Retention time in HPLC (min) | | |
|---|---|---|---|
| Objective substance | Enantiomer of objective substance | | Excess ratio (objective substance:enantiomer of objective substance) |
| 5.83 | 7.27 | | 99.4% ee (99.7:0.3) |

Example 5

Michael Reaction of Chiral Glycine Equivalent and α,β-Unsaturated Carbonyl Compound and Synthesis of Optically Active Amino Acid Example 5-1: Synthesis of Nickel (II) Complex Having L-glutamic Acid γ-methyl ester Moiety by Michael Reaction of Chiral Glycine Equivalent and Methyl Acrylate

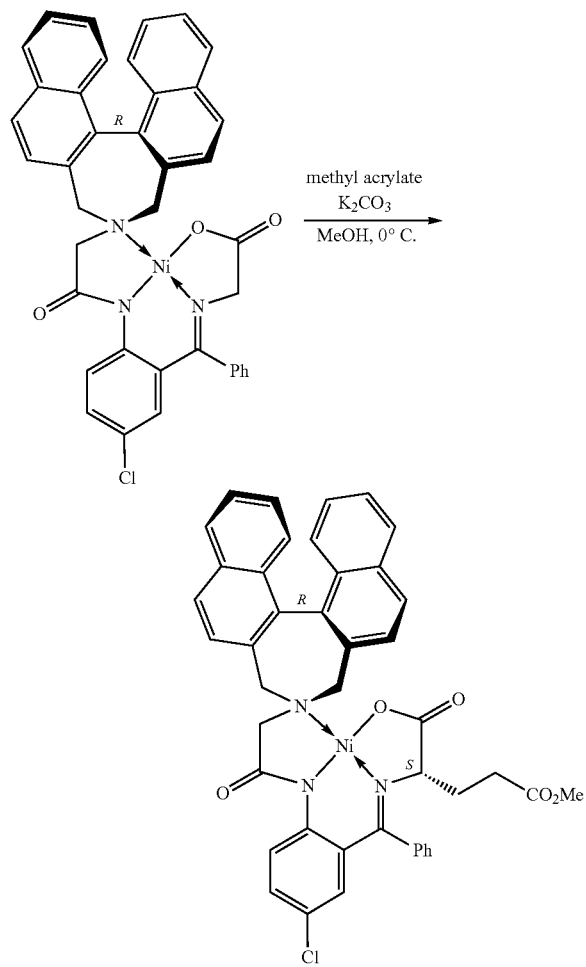

To a methanol suspension (3 mL) of a chiral glycine equivalent (R-isomer) (0.154 g, 0.226 mmol), methyl acrylate (0.029 g, 0.339 mmol) and anhydrous potassium carbonate (0.005 g, 0.034 mmol) were added. The mixture was stirred at room temperature for 2 hours. The reaction mixture was added to an ice-cooled 5% acetic acid aqueous solution (30 mL), and the whole was stirred for 30 minutes. The precipitated crystals were separated by filtration, and then blow-dried at 50° C. to give a nickel (II) complex having an L-glutamic acid γ-methyl ester moiety (0.164 g, yield: 95.1%, 93% de) as red crystals. The crystals were subjected to recrystallization from dichloromethane-methanol to give a nickel (II) complex having an L-glutamic acid γ-methyl ester moiety (0.120 mg, yield: 69.3%, 96.0% de).

ESI-MS (positive mode): m/z=766.4 for [M+H]$^+$ $^1$H-NMR (200 MHz, CDCl$_3$): δ 1.70-1.91 (1H, m), 2.11-2.30 (1H, m), 2.61-2.78 (1H, m, one of 7-CH$_2$ of Glu part), 2.65 [1H, d, J=12.1 Hz, one of azepine C(α)H$_2$N], 3.01 [1H, d, J=15.6 Hz, one of azepine C(α'r)H$_2$N], 3.48 (1H, ddd, J=16.8, 9.5, 5.7 Hz, one of 7-CH$_2$ of Glu part), 3.60 (3H, s, OMe), 3.79 and 3.91 (1H each, ABq, J=13.8 Hz, acetanilide NCOCH$_2$), 3.91 (1H, dd, J=6.4, 3.5 Hz, α-H of Glu part), 4.67 [1H, d, J=15.6 Hz, one of azepine C(α)H$_2$N], 4.80 [1H, d, J=12.2 Hz, one of azepine C(α)H$_2$N], 6.60 (1H, d, J=2.6 Hz, ArH), 7.04-7.17 (2H, m, ArH), 7.20-7.32 (3H, m, ArH), 7.35-7.57 (7H, m, ArH), 7.61 (1H, d, J=8.2 Hz, ArH), 7.94-8.04 (3H, m, ArH), 8.16 (1H, d, J=8.2 Hz, ArH), 8.47 (1H, d, J=9.2 Hz, ArH), 8.82 (1H, d, J=8.2 Hz, ArH).

$^{13}$C-NMR (50.3 MHz, CDCl$_3$): δ 28.0 (CH$_2$), 30.2 (CH$_2$), 52.2 (OMe), 58.7 (NCOCH$_2$), 61.8 and 66.4 (2×CH$_2$ of azepine), 70.1 (α-CH of Glu part), 125.1 (ArCH), 126.1 (quaternary ArC), 126.4 (ArCH), 126.7 (ArCH), 127.4 (ArCH), 127.76 (ArCH), 127.84 (ArCH), 128.1 (quaternary ArC), 128.4 (ArCH), 128.6 (ArCH), 128.8 (quaternary ArC), 129.1 (ArCH), 129.3 (ArCH), 129.4 (ArCH), 130.2 (ArCH), 131.0 (quaternary ArC), 131.2 (quaternary ArC), 131.5 (quaternary ArC), 132.5 (ArCH), 132.7 (ArCH), 132.9 (quaternary ArC), 133.7 (quaternary ArC), 134.0 (quaternary ArC), 135.4 (quaternary ArC), 136.1 (quaternary ArC), 141.1 (quaternary ArC), 171.3, 173.4, 174.9, 177.8 (CN and 3×CO).

Figure 17:
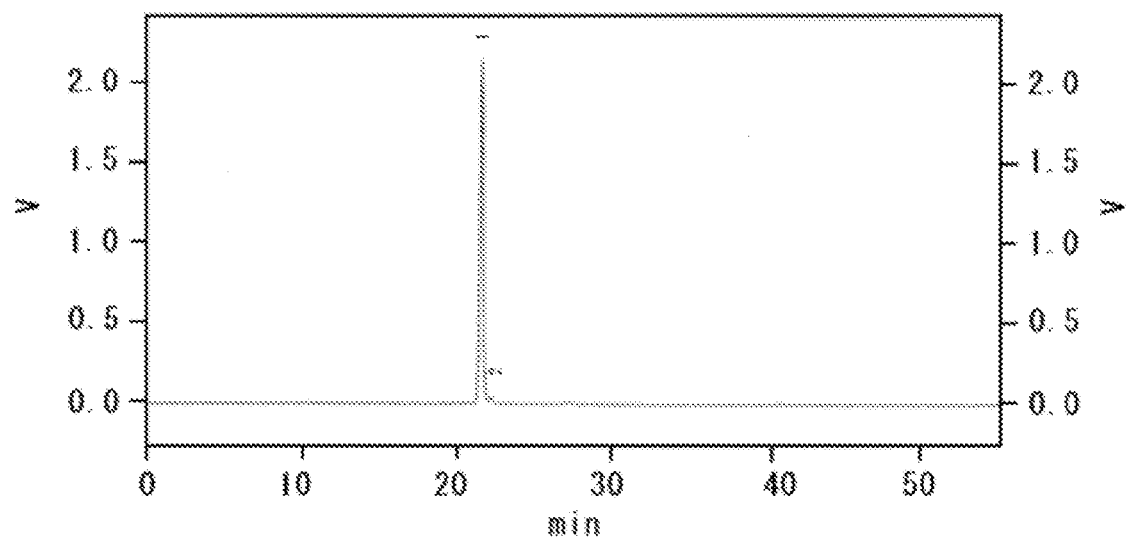
FIG. 17 shows a HPLC chromatogram of the compound prepared in Example 5-1.

HPLC analysis was conducted on the obtained compound under the above <HPLC conditions-1: complex analysis conditions>. The results are shown in Table 18 and FIG. 17.

TABLE 18

| | Retention time in HPLC (min) | |
|---|---|---|
| Objective substance | Isomer of objective substance | Excess ratio (objective substance:isomer of objective substance) |
| 21.6 | 22.2 | 96.0% de (98.0:2.0) |

Example 5-2: Release of L-glutamic acid γ-methyl ester from Nickel (II) Complex Having L-glutamic acid γ-methyl ester Moiety Under Acidic Conditions and Protection of L-glutamic acid γ-methyl ester with Z Group

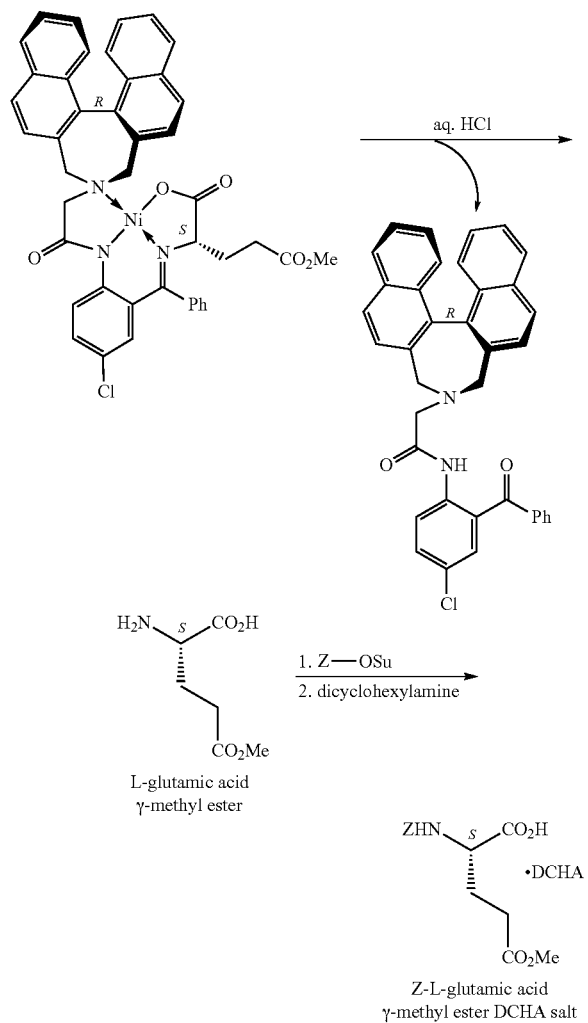

To a methanol suspension (3.6 mL) of a nickel (II) complex having an L-glutamic acid γ-methyl ester moiety (0.12 g, 0.16 mmol), 6 N hydrochloric acid (0.13 mL, 5 eq.) was added, and the mixture was stirred at 30 to 40° C. for 7 hours. The reaction mixture was concentrated under reduced pressure, and the residue was dissolved in dichloromethane (4 mL). The organic layer was washed with water (1 mL), and the aqueous layer was extracted with dichloromethane (2 mL, twice). All the organic layers were combined and dichloromethane was added thereto so that the total volume thereof was about 20 mL. This was washed with a saturated sodium bicarbonate aqueous solution (5 mL), with water (5 mL), and with saturated brine (5 mL), and dried over sodium sulfate. The solvent was removed by evaporation to give a chiral auxiliary (R-isomer) (0.09 g, yield: 98%).

Meanwhile, to the aqueous layer, EDTA disodium salt dihydrate (0.06 g, 1 eq.), acetone (1 mL), and an acetone solution (1 mL) of N-benzyloxycarbonyloxy succinimide (0.16 g, 5 eq.) were added. The pH of the mixture was adjusted to 7 to 8 using sodium hydrogen carbonate, and then the mixture was stirred overnight. The acetone was removed from the reaction mixture under reduced pressure. To the residue, dichloromethane (20 mL) was added, and the pH of the mixture was adjusted to 3 using 4 N hydrochloric acid. After phase separation, the aqueous layer was extracted with dichloromethane (20 mL). The organic layers were combined and washed with saturated brine (2 mL), dried over sodium sulfate, and then concentrated to dryness to give a colorless oily substance (0.16 g). The obtained oily substance was dissolved in isopropanol-ethyl acetate (0.1 mL:1 mL), and dicyclohexylamine (0.08 g, 3 eq.), petroleum ether (3 mL), and hexane (3 mL) were added to the solution. The mixture was stirred overnight. The precipitated crystals were separated by filtration, and then dried at 50° C. under reduced pressure to give a Z-L-glutamic acid γ-methyl ester DCHA salt (0.04 g, yield: 56%, 99.8% ee).

Figure 18:
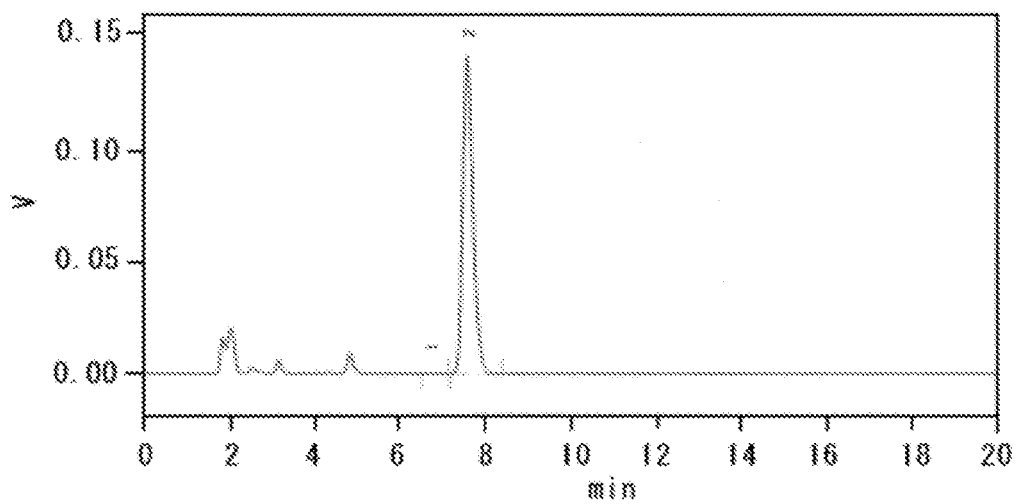
FIG. 18 shows a HPLC chromatogram of the compound prepared in Example 5-2.

HPLC analysis was conducted on the obtained compound under the following conditions. The results are shown in Table 19 and FIG. 18.

<HPLC Conditions: Z-Glu(5-OMe) Chiral Analysis Conditions>

Column: CHIRALCEL OJ-RH (5 μm, 150×4.6 mm i.d.)
Eluent: A:B=75:25 (0 to 20 min)
 A=0.1% phosphoric acid aqueous solution
 B=0.1% solution of phosphoric acid in acetonitrile
Flow rate: 1.0 mL/min
Temperature: 30° C.
Detector: UV 220 nm

TABLE 19

| Retention time in HPLC (min) | | Excess ratio |
|---|---|---|
| Z-D-Glu(5-OMe) | Z-L-Glu(5-OMe) | (D:L) |
| 6.8 | 7.6 | 99.8% ee (0.1:99.9) |

Example 5-3: Synthesis of Nickel (II) Complex Having L-glutamine Moiety by Michael Reaction of Chiral Glycine Equivalent and Acrylamide

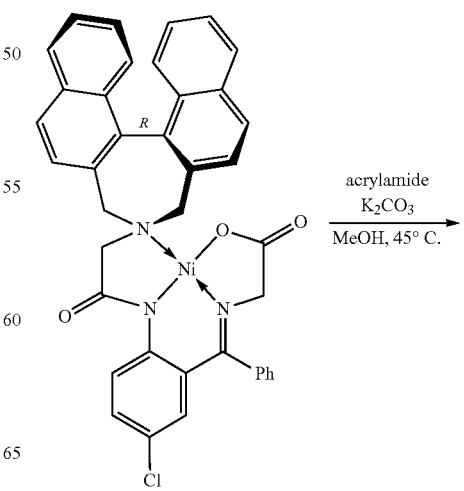

-continued

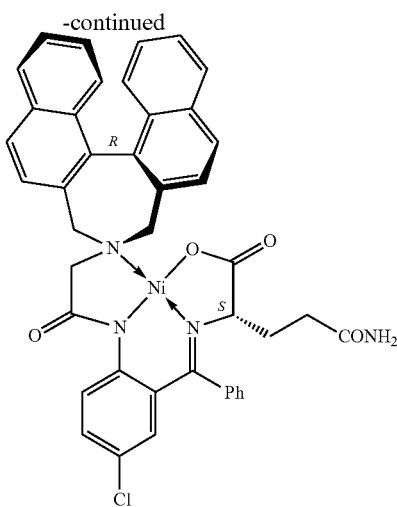

Under an argon atmosphere, to a methanol suspension (1 mL, methanol was preliminarily deaerated) of a chiral glycine equivalent (R-isomer) (0.100 g, 0.147 mmol), acrylamide (0.016 g, 0.220 mmol) and anhydrous potassium carbonate (0.060 g, 0.441 mmol) were added. The mixture was stirred at 45° C. for 2 hours. To the reaction mixture, an ice-cooled 5% acetic acid aqueous solution (5 mL) and dichloromethane (5 mL) were added, and the whole was stirred. After phase separation, the aqueous layer was extracted with dichloromethane (5 mL). The organic layers were combined and washed with water (2.5 mL, 5 times) and with saturated brine (2.5 mL), dried over sodium sulfate, and then concentrated to dryness. The concentrated residue was purified by silica gel chromatography (dichloromethane:methanol=95:5) to give a nickel (II) complex having an L-glutamine moiety (0.096 g, yield: 86.7%, 99.8% de) as red crystals.

ESI-MS (positive mode): m/z=751.3 for [M+H]$^+$ $^1$H-NMR (200 MHz, CDCl$_2$): δ 1.68-1.88 (1H, m), 2.09-2.25 (1H, m), 2.34-2.70 (2H, m), 2.72 [1H, d, J=12.2 Hz, one of azepine C(α)H$_2$N], 3.00 [1H, d, J=15.6 Hz, one of azepine C(α')H$_2$N], 3.62 and 3.73 (1H each, ABq, J=13.7 Hz, acetanilide NCOCH$_2$), 3.79 (1H, dd, J=8.7, 4.3 Hz, α-H of Gln part), 4.56 [1H, d, J=15.6 Hz, one of azepine C(α')H$_2$N], 4.84 [1H, d, J=12.2 Hz, one of azepine C(α)H$_2$N], 5.20 (1H, br s, one of CONH$_2$), 6.38 (1H, br s, one of CONH$_2$), 6.66 (1H, d, J=2.4 Hz, ArH), 6.94-7.01 (1H, m, ArH), 7.13-7.20 (1H, m, ArH), 7.21-7.33 (3H, m, ArH), 7.37-7.59 (8H, m, ArH), 7.86-8.01 (3H, m, ArH), 8.15 (1H, d, J=8.2 Hz, ArH), 8.45 (1H, d, J=9.2 Hz, ArH), 8.74 (1H, d, J=8.4 Hz, ArH).

$^{13}$C-NMR (50.3 MHz, CDCl$_3$): δ 30.2 (CH$_2$), 31.2 (CH$_2$), 58.4 (NCOCH$_2$), 61.9 and 66.2 (2×CH$_2$ of azepine), 69.8 (α-CH of Gln part), 125.2 (ArCH), 126.1 (quaternary ArC), 126.5 (ArCH), 126.6 (ArCH), 127.3 (ArCH), 127.5 (ArCH), 127.8 (ArCH), 128.0 (ArCH), 128.1 (quaternary ArC), 128.4 (ArCH), 128.6 (ArCH), 128.8 (quaternary ArC), 129.0 (ArCH), 129.1 (ArCH), 129.3 (ArCH), 129.5 (ArCH), 130.3 (ArCH), 131.1 (quaternary ArC), 131.2 (quaternary ArC), 131.4 (quaternary ArC), 132.6 (ArCH), 132.7 (ArCH), 133.6 (quaternary ArC), 133.9 (quaternary ArC), 135.5 (quaternary ArC), 136.1 (quaternary ArC), 141.0 (quaternary ArC), 170.7, 173.6, 174.8, 178.5 (CN and 3×CO).

Figure 19:
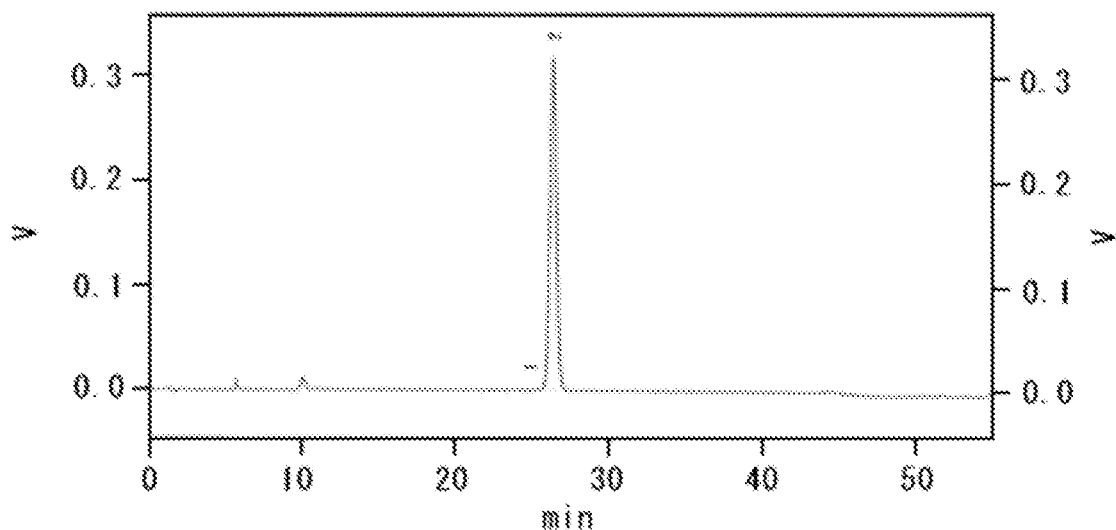
FIG. 19 shows a HPLC chromatogram of the compound prepared in Example 5-3.

HPLC analysis was conducted on the obtained compound under the following conditions. The results are shown in Table 20 and FIG. 19.

<HPLC Conditions-2: Complex Analysis Conditions>
Column: Inertsil ODS-3 (3 μm, 150×4.6 mm i.d.)
Eluent: A:B=40:60 (0 to 40 min) and
10:90 (40 to 50 min)
A=10 mM ammonium formate in 0.1% formic acid buffer solution
B=acetonitrile
Flow rate: 0.5 mL/min
Temperature: 30° C.
Detector: UV 254 nm

TABLE 20

| Retention time in HPLC (min) | | Excess ratio |
|---|---|---|
| Isomer of objective substance | Objective substance | (isomer of objective substance:objective substance) |
| 25.4 | 26.3 | 99.8% de (0.1:99.9) |

Example 5-4: Release of L-glutamine from Nickel (II) Complex Having L-glutamine Moiety Under Acidic Conditions and Protection of L-glutamine with Z Group

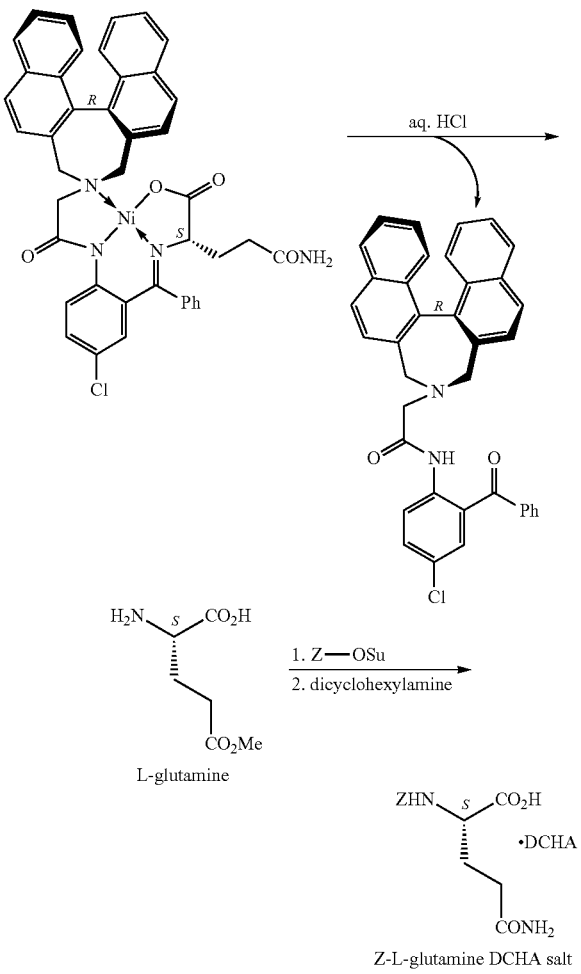

To a methanol suspension (2.9 mL) of a nickel (II) complex having an L-glutamine moiety (0.10 g, 0.13 mmol), 1 N hydrochloric acid (0.6 mL, 5 eq.) was added, and the mixture was stirred at 30° C. for 2 hours. The reaction mixture was concentrated under reduced pressure, and the residue was dissolved in dichloromethane (5 mL). The organic layer was washed with water (2.5 mL) and the aqueous layer was extracted with dichloromethane (5 mL). The organic layers were combined and washed with a saturated sodium bicarbonate aqueous solution (2.5 mL), with water (2.5 mL), and with saturated brine (2.5 mL). This was dried over sodium sulfate and then concentrated to dryness to give a chiral auxiliary (R-isomer) (0.07 g, yield: 95%).

Meanwhile, to the aqueous layer, EDTA disodium salt dihydrate (0.054 g, 1.1 eq.) and acetone (1 mL) were added. An acetone solution (1.5 mL) of N-benzyloxycarbonyloxy succinimide (0.043 g, 1.1 eq.) was added thereto, the pH was adjusted to 9 using 1 N sodium hydroxide aqueous solution, and then the mixture was stirred for 2.5 hours. The acetone was removed from the reaction mixture under reduced pressure, and the residue was subjected to phase separation with ethyl acetate (8 mL) and 1 N hydrochloric acid (1 mL). The aqueous layer was extracted with ethyl acetate (5 mL, twice). The organic layers were combined and washed with saturated brine (2 mL), dried over sodium sulfate, and then concentrated to dryness to give a brown oily substance (0.05 g). The obtained oily substance was dissolved in isopropanol (0.07 mL) and ethyl acetate (1 mL), and dicyclohexylamine (0.03 g, 1 eq.) was added to the solution. The mixture was stirred overnight. The precipitated crystals were separated by filtration, and then dried at 50° C. under reduced pressure to give a Z-L-glutamine DCHA salt (0.03 g, yield: 48%, 99.2% ee).

Figure 20:
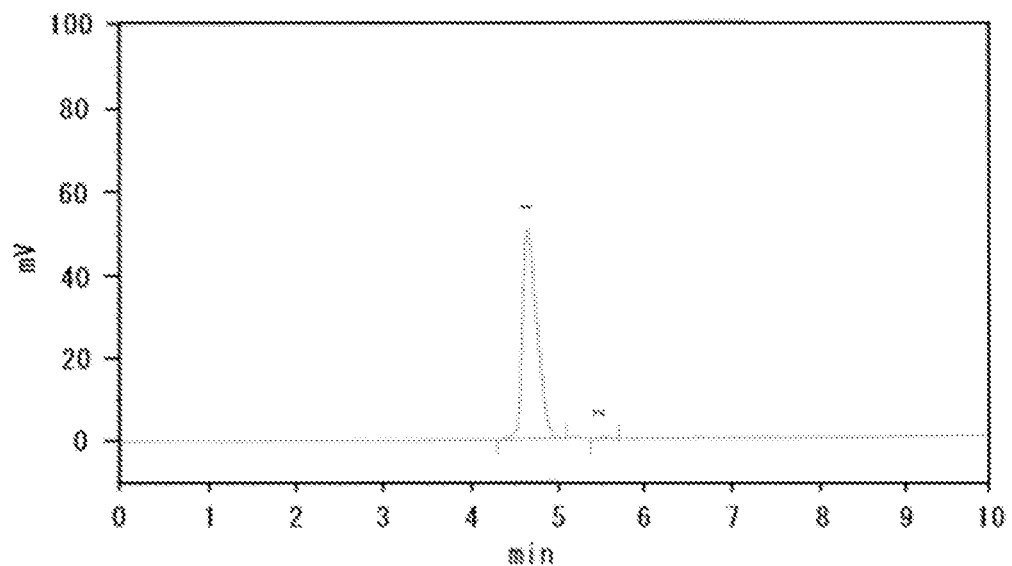
FIG. 20 shows a HPLC chromatogram of the compound prepared in Example 5-4.

HPLC analysis was conducted on the obtained compound under the following conditions. The results are shown in Table 21 and FIG. 20.

<HPLC Conditions: Z-Gln Chiral Analysis Conditions>
Column: CHIROBIOTIC T (5 μm, 150×4.6 mm i.d.)
Eluent: A:B=30:70
  A=methanol
  B=0.1% triethylammonium acetate buffer solution (pH 4.1)
Flow rate: 0.7 mL/min
Temperature: 40° C.
Detector: UV 254 nm

TABLE 21

| Retention time in HPLC (min) | | Excess ratio |
|---|---|---|
| Z-L-Gln | Z-D-Gln | (D:L) |
| 4.7 | 5.5 | 99.2% ee (0.4:99.6) |

Example 5-5: Synthesis of Nickel (II) Complex Having 3-methyl-L-glutamic acid γ-methyl ester Moiety by Michael Reaction of Chiral Glycine Equivalent and Methyl Crotonate

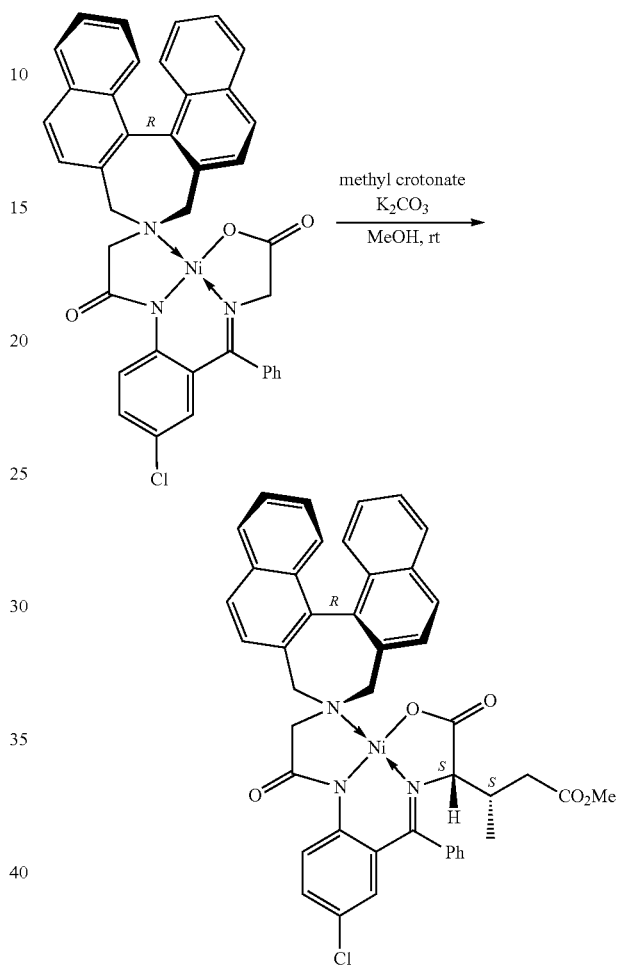

Under an argon atmosphere, to a methanol suspension (8 mL, methanol was preliminarily deaerated) of a chiral glycine equivalent (R-isomer) (0.400 g, 0.588 mmol), methyl crotonate (0.130 g, 1.175 mmol) and anhydrous potassium carbonate (0.243 g, 1.763 mmol) were added. The mixture was stirred at room temperature for 2 hours. To the reaction mixture, an ice-cooled 5% acetic acid aqueous solution (5 mL) and dichloromethane (10 mL) were added, and the whole was stirred. After phase separation, the organic layer was washed with water (5 mL, twice) and with saturated brine (5 mL), dried over sodium sulfate, and then concentrated to dryness. The concentrated residue (469.0 mg, objective substance:isomer 1 of objective substance: isomer 2 of objective substance=83.2:13.8:2.9) was purified by silica gel chromatography (benzene:acetone=95:5) to give a nickel (II) complex having a 3-methyl-L-glutamic acid γ-methyl ester moiety (0.300 g, yield: 65.4%, chemical purity: >99%) as red crystals.

Figure 21:
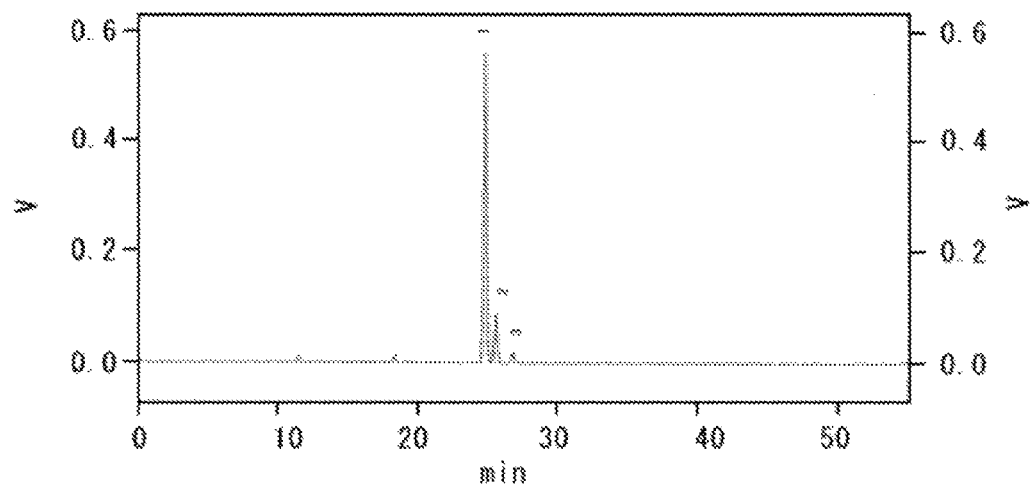
FIG. 21 shows a HPLC chromatogram of the compound prepared in Example 5-5.

HPLC analysis was conducted on the compound before the purification under the above <HPLC conditions-1: complex analysis conditions>. The results are shown in Table 22 and FIG. 21.

TABLE 22

| | Retention time in HPLC (min) | | Excess ratio |
|---|---|---|---|
| Objective substance | Isomer 1 of objective substance | Isomer 2 of objective substance | (objective substance:isomer 1 of objective substance:isomer 2 of objective substance) |
| 24.8 | 25.6 | 26.8 | 66.5% de (83.2:13.8:2.9) |

In this example, the objective substance is a compound in which the configuration of the α carbon is S-configuration and the configuration of the β carbon is S-configuration. Isomer 1 of the objective substance is a compound in which the α carbon is in the S-configuration and the β carbon is in the R-configuration. Moreover, Isomer 2 of the objective substance is a compound in which the α carbon is in the R-configuration and the β carbon is in the S-configuration.

ESI-MS (positive mode): m/z=779.9 for [M+H]$^+$ $^1$H-NMR (200 MHz, CDCl$_3$): δ 1.97-2.32 (6H, m), 2.65 [1H, d, J=12.1 Hz, one of azepine C(α)H$_2$N], 3.06 [1H, d, J=15.6 Hz, one of azepine C(α)H$_2$N], 3.49 (3H, s, OMe), 3.64 and 3.73 (1H each, ABq, J=13.9 Hz, acetanilide NCOCH$_2$), 3.84 (1H, d, J=2.4 Hz, α-H of amino acid part), 4.55 [1H, d, J=15.6 Hz, one of azepine C (α')H$_2$N], 4.76 [1H, d, J=12.1 Hz, one of azepine C(α)H$_2$N], 6.62 (1H, br d, J=2.6 Hz, ArH), 6.95-7.02 (1H, m, ArH), 7.09 (1H, br d, J=7.0 Hz, ArH), 7.20-7.31 (3H, m, ArH), 7.34-7.59 (8H, m, ArH), 7.94-8.03 (3H, m, ArH), 8.16 (1H, d, J=8.2 Hz, ArH), 8.46 (1H, d, J=9.2 Hz, ArH), 8.82 (1H, d, J=8.4 Hz, ArH).

$^{13}$C-NMR (50.3 MHz, CDCl$_3$): δ 16.3 (3-Me), 35.1 (β-CH), 37.9 (γ-CH2), 51.5 (OMe), 59.1 (NCOCH$_2$), 61.6 and 66.6 (2×CH$_2$ of azepine), 74.1 (α-CH), 125.0 (ArCH), 126.1 (quaternary ArC), 126.3 (ArCH), 126.4 (ArCH), 126.9 (ArCH), 127.2 (ArCH), 127.4 (ArCH), 127.5 (ArCH), 127.9 (ArCH), 128.3 (quaternary ArC), 128.4 (ArCH), 128.6 (ArCH), 129.1 (ArCH), 129.35 (ArCH), 129.42 (ArCH), 130.3 (ArCH), 130.9 (quaternary ArC), 131.2 (quaternary ArC), 131.5 (quaternary ArC), 132.6 (ArCH), 133.7 (ArCH), 134.0 (quaternary ArC), 135.5 (quaternary ArC), 136.0 (quaternary ArC), 141.1 (quaternary ArC), 170.7, 172.0, 174.4, 176.1 (CN and 3×CO).

Example 5-6: Release of (2S,3S)-3-methyl-L-glutamic acid γ-methyl ester from Nickel (II) Complex Having 3-methyl-L-glutamic acid γ-methyl ester Moiety Under Acidic Conditions, Protection of (2S,3S)-3-methyl-L-glutamic acid γ-methyl ester with Z Group, and Determination of Stereochemistry of (2S,3S)-3-methyl-L-glutamic acid

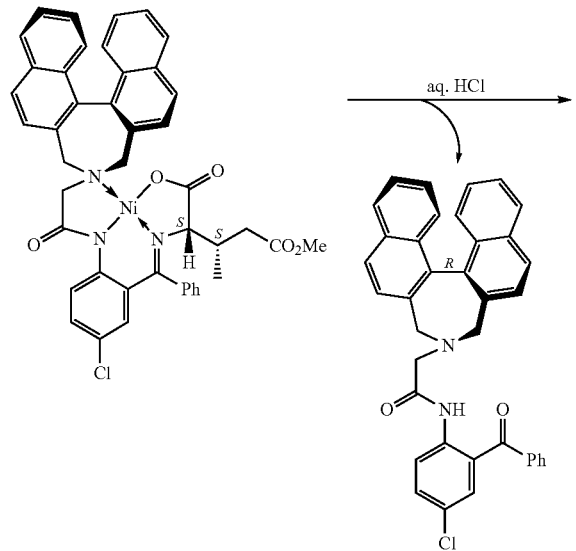

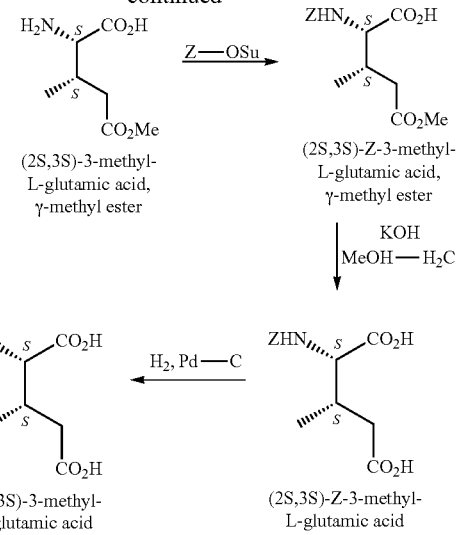

To a methanol suspension (9 mL) of a nickel (II) complex having a (2S,3S)-3-methyl-L-glutamic acid γ-methyl ester moiety (0.30 g, 0.384 mmol), 1 N hydrochloric acid (2.3 mL, 6 eq.) was added, and the mixture was stirred at 50° C. for 4 hours. The reaction mixture was concentrated under reduced pressure, and the residue was dissolved in ethyl acetate (6 mL). The solution was washed with water (2 mL), and then the aqueous layer was extracted with ethyl acetate (1 mL). The organic layers were combined and washed with a saturated sodium bicarbonate aqueous solution (2 mL), with water (2 mL), and with saturated brine (2 mL). This was dried over sodium sulfate, and then the solvent was removed by evaporation to give a chiral auxiliary (0.22 g, quantitative).

Meanwhile, to the aqueous layer, EDTA disodium salt dihydrate (0.14 g, 1 eq.), acetone (1 mL), and water (1.1 mL) were added. An acetone solution (1 mL) of N-benzyloxycarbonyloxysuccinimide (0.12 g, 1.2 eq.) was added thereto, the pH was adjusted to 7 to 8 using sodium hydrogen carbonate, and then the mixture was stirred overnight. The acetone was removed by evaporation from the reaction mixture, and to the residue, ethyl acetate (5 mL) and 1 N hydrochloric acid were added. The mixture was stirred and then the pH of the aqueous layer was adjusted to 2 to 3. After phase separation, the aqueous layer was extracted with ethyl acetate (5 mL and 2.5 mL). The organic layers were combined and washed with saturated brine (1 mL) and dried over sodium sulfate. The solvent was removed by evaporation to give a yellow oily substance (0.16 g). The oily substance was dissolved in water (1 mL) and methanol (2 mL), and potassium hydroxide (0.10 g, 4 eq.) was added to the solution. The mixture was stirred at room temperature for 4.5 hours. The methanol was removed by evaporation from the reaction mixture, and the residue was subjected to phase separation with water (20 mL), ethyl acetate (2 mL), and hexane (1 mL). The aqueous layer was washed with ethyl acetate (2 mL, twice), and then the pH was adjusted to 6.5 using 4 N hydrochloric acid. The aqueous layer was further washed with ethyl acetate (2 mL, 3 times and 1 mL, 6 times). Subsequently, the pH was adjusted to 2 using 4 N hydrochloric acid, and then the aqueous layer was extracted with ethyl acetate (20 mL and 10 mL). The organic layers were combined and washed with saturated brine (1.5 mL) and dried over sodium sulfate. The solvent was removed by evaporation to give (2S,3S)-Z-3-methyl-L-glutamic acid (0.074 g, yield: 68.4%, chemical purity: 97.5%) as a colorless oily substance.

To a methanol solution (1 mL) of the obtained (2S,3S)-Z-3-methyl-L-glutamic acid (0.04 g, 0.14 mmol), 10% Pd/C (0.002 mg, 0.5 mol %) was added, and the mixture was stirred at room temperature for 1 hour under a hydrogen atmosphere. The Pd/C was filtered off and the solvent was removed by evaporation to give (2S,3S)-3-methyl-L-glutamic acid (0.02 g, yield: 98.6%) as a white solid.

$[\alpha]^{25}_D$=+40.8° (c 0.19, 6N HCl)

$^1$H-NMR (200 MHz, NaOD/D$_2$O): δ 3.01 (1H, d, J=5.7 Hz), 2.34 (2H, dd, J=3.3 and 13.0 Hz), 1.95-2.10 (1H, m), 1.84 (1H, dd, J=11.3 and 12.8 Hz), 0.87 (3H, d, J=6.4 Hz)

Literature values (M. Xian et al., J. Org. Chem., 2007, 72, 7560) will be shown below for reference.

(2S,3S)-3-methyl-L-glutamic acid $[\alpha]^{25}_D$=+42.0° (c 0.9, 6N HCl)

$^1$H-NMR (400 MHz, NaOD/D$_2$O) δ 2.96 (1H, d, J=6.0 Hz), 2.26 (2H, dd, J=4.0 and 13.5 Hz), 1.96 (1H, m), 1.79 (1H, dd, J=11.0 and 13.0 Hz), 0.81 (3H, d, J=7.0 Hz)

(2S,3R)-3-methyl-L-glutamic acid $[\alpha]^{25}_D$=+18.2° (c 0.9, 6N HCl)

$^1$H-NMR (400 MHz, NaOD/D$_2$O) δ 3.14 (1H, d, J=4.0 Hz), 2.22 (2H, dd, J=5.0 and 13.0 Hz), 2.18 (1H, m), 1.98 (1H, dd, J=9.5 and 13.0 Hz), 0.79 (3H, d, J=7.0 Hz)

Example 6: Release of (S)-α-allylalanine from Nickel (II) Complex Having (S)-α-allylalanine Moiety Under Acidic Conditions

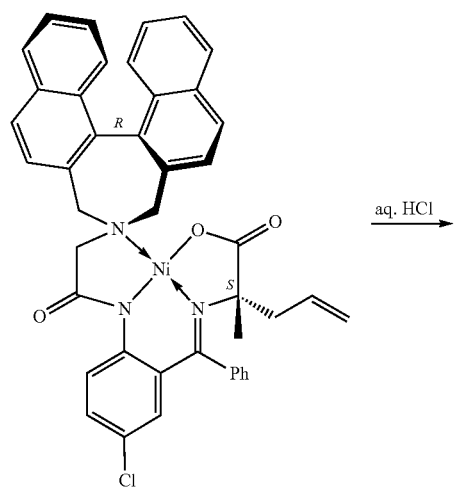

aq. HCl →

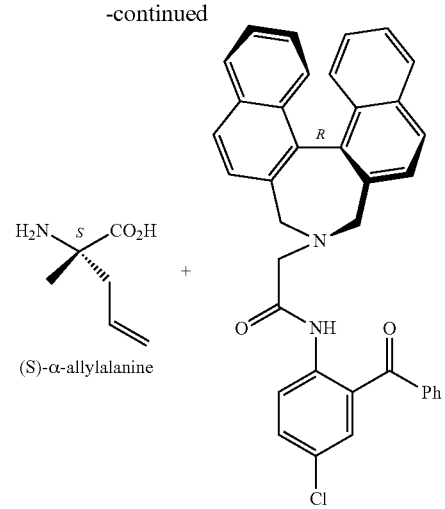

(S)-α-allylalanine

To a methanol (9.0 mL) suspension of a nickel (II) complex having an (S)-α-allylalanine moiety (300.0 mg, 0.408 mmol) which was synthesized in Example 3-4, 1 N hydrochloric acid (2.0 mL, 2.04 mmol) was added. The mixture was stirred at 40° C. for 1 hour. The reaction mixture was concentrated under reduced pressure, and the residue was dissolved in dichloromethane (20 mL) and water (20 mL). After phase separation, the organic layer was washed with 2% aqueous ammonia (10 mL, twice), with water (10 mL, twice), and then with saturated brine (10 mL, twice). The organic layer was dried over sodium sulfate, and then the solvent was removed by evaporation to give a chiral auxiliary (R-isomer) (255 mg, yield: quantitative).

Meanwhile, the aqueous layer was concentrated to dryness, and the resulting solid was dissolved in a mixed solvent of water (7.0 mL), 1 N hydrochloric acid (1.0 mL), and methanol (2.0 mL). The solution was passed through a cation exchange resin column [SK-1B, 10 mL, eluent: water and subsequently 2% aqueous ammonia] to give (S)-α-allylalanine (47.7 mg, 0.369 mmol, yield: 90%, >98% ee) as a white solid.

Figure 22:
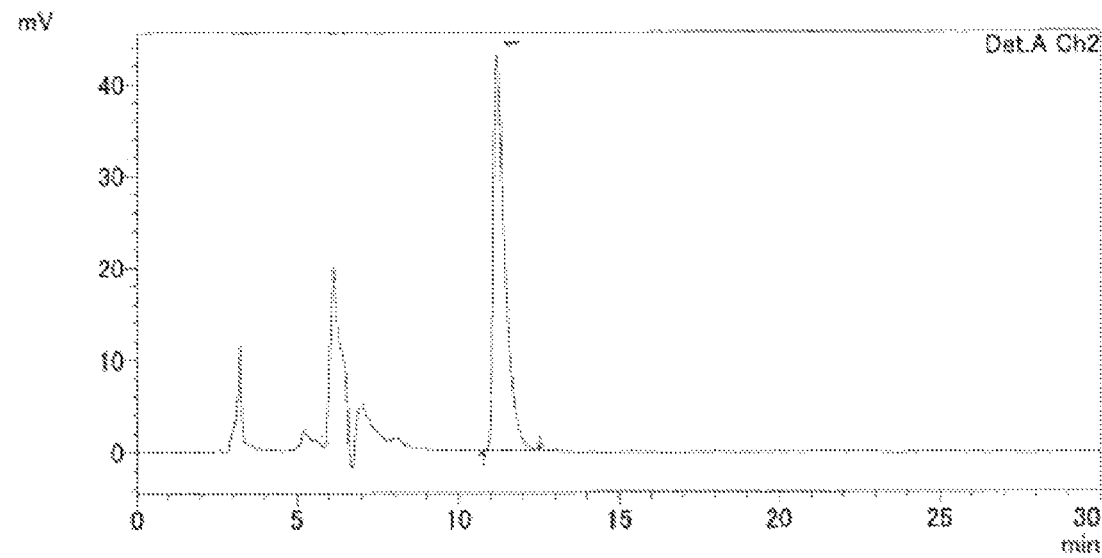
FIG. 22 shows a HPLC chromatogram of the compound prepared in Example 6.

HPLC analysis was conducted on the obtained compound under the following conditions. The results are shown in Table 23 and FIG. 22.

<HPLC Conditions: (S)-α-allylalanine Chiral Analysis Conditions>
Column: CHIROBIOTIC T (5 μm, 250×4.6 mm i.d.)
Eluent: A:B=30:70
  A=water
  B=ethanol
Flow rate: 0.5 mL/min
Temperature: 40° C.
Detector: UV 210 nm

TABLE 23

| Retention time in HPLC (min) | | |
|---|---|---|
| Objective substance (S)-α-allylalanine | Isomer of objective substance (R)-α-allylalanine | Excess ratio (objective substance:isomer of objective substance) |
| 11.2 | 12.2 (determined by analysis of racemic standard) | >98% ee (quantitation limit in indicated analysis conditions is at the level of 1%) |

Example 7-1: Synthesis of Nickel (II) Complex Having (R)-S-benzyl-α-methylcysteine Moiety by Reaction of Nickel (II) Complex Having Alanine Moiety and Benzyl Chloromethyl Sulfide

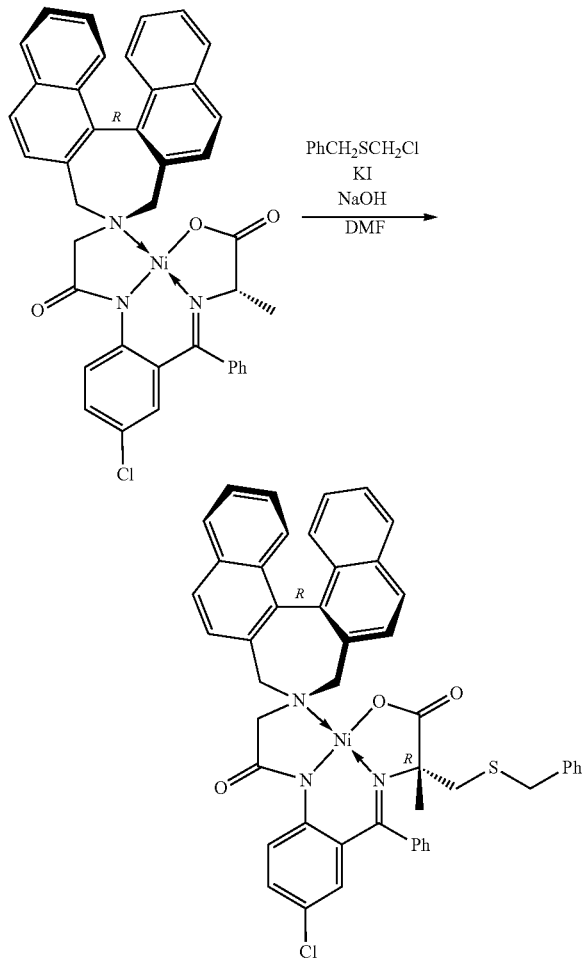

Under an argon atmosphere, to a dimethylformamide (DMF) solution (3 mL) of a nickel (II) complex having an alanine moiety (1.0 g, 1.44 mmol), sodium hydroxide (288 mg, 7.20 mmol) was added, and the mixture was stirred at −20° C. for 5 minutes. To this, benzyl chloromethyl sulfide (621 mg, 3.60 mmol) and potassium iodide (657 mg, 3.96 mmol) were sequentially added. The mixture was stirred at 0° C. for 1 hour. The reaction mixture was added to an ice-cooled 5% acetic acid aqueous solution (40 mL). The precipitated crystals were separated by filtration and purified by silica gel column chromatography (dichloromethane: acetone=40:1) to give a nickel (II) complex having an (R)-S-benzyl-α-methylcysteine moiety (585 mg, yield: 48.9%, >99.9% de) as red crystals.

ESI-MS (positive mode): m/z calcd for $C_{48}H_{38}ClN_3NiO_3S$ [M+H]$^+$ 830.18. found 830.1.

$^1$H-NMR (200 MHz, CDCl$_3$): δ 1.00 (3H, s, α-Me), 2.67 and 2.83 (1H each, ABq, J=12.0 Hz, β-CH$_2$ of the amino acid part), 2.75 [1H, d, J=12.0 Hz, one of azepine C(α)H$_2$N], 3.08 [1H, d, J=15.1 Hz, one of azepine C(α')H$_2$N], 3.64 and 3.83 (1H each, ABq, J=13.8 Hz, acetanilide NCOCH$_2$), 3.98 and 4.07 (1H each, ABq, J=13.1 Hz, SCH$_2$Ph), 4.43 [1H, d, J=15.1 Hz, one of azepine C(α')H$_2$N], 4.80 [1H, d, J=12.0 Hz, one of azepine C(α)H$_2$N], 6.66-6.73 (1H, m, ArH), 6.72 (1H, d, J=2.6 Hz), 7.16-7.56 (17H, m, ArH), 7.91-8.01 (3H, m, ArH), 8.11 (1H, d, J=8.4 Hz, ArH), 8.31 (1H, d, J=9.0 Hz, ArH), 8.67 (1H, d, J=8.2 Hz, ArH).

$^{13}$C-NMR (50.3 MHz, CDCl$_3$): δ 28.4 (Me), 38.1 (CH$_2$), 42.3 (CH$_2$), 58.9 (NCOCH$_2$), 61.5 and 66.1 (2×CH$_2$ of azepine), one quaternary α-carbon of the amino acid part overlapping with signals of CDCl$_3$, 125.0 (ArCH), 125.9 (quaternary ArC), 126.2 (ArCH), 126.3 (ArCH), 126.6 (ArCH), 127.3 (ArCH), 127.4 (ArCH), 127.5 (ArCH), 128.1 (ArCH), 128.4 (ArCH), 128.5 (ArCH), 128.6 (quaternary ArC), 128.7 (ArCH), 128.9 (quaternary ArC), 129.0 (ArCH), 129.1 (ArCH), 129.2 (ArCH), 129.5 (ArCH), 129.8 (ArCH), 130.4 (quaternary ArC), 131.2 (quaternary ArC), 131.3 (quaternary ArC), 131.4 (quaternary ArC), 132.2 (ArCH), 132.6 (ArCH), 133.6 (quaternary ArC), 133.9 (quaternary ArC), 135.3 (quaternary ArC), 135.5 (quaternary ArC), 136.0 (quaternary ArC), 137.7 (quaternary ArC), 140.5 (quaternary ArC), 171.6, 174.3, 179.7 (CN and 2×CO).

Figure 23:
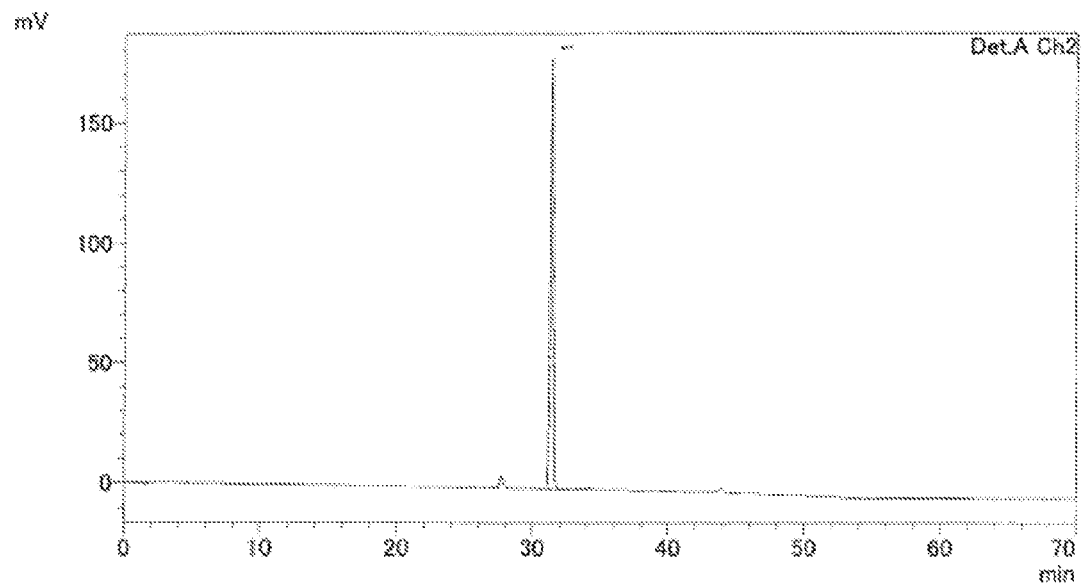
FIG. 23 shows a HPLC chromatogram of the compound prepared in Example 7-1.

HPLC analysis was conducted on the obtained compound under the following conditions. The results are shown in Table 24 and FIG. 23.

<HPLC Conditions: Complex Analysis Conditions>
Column: Inertsil ODS-3 (3 μm, 150×4.6 mm i.d.)
Eluent: A:B=40:60 to 0:100 (0 to 50 min)
  A=10 mM ammonium formate in 0.1% formic acid buffer solution
  B=acetonitrile
Flow rate: 1.0 mL/min
Temperature: 30° C.
Detector: UV 254 nm

TABLE 24

| Retention time in HPLC (min) | | Excess ratio (objective substance:isomer of objective substance) |
|---|---|---|
| Objective substance | Isomer of objective substance | |
| 31.4 | 35.2 | >99.9% de |

Example 7-2: Release of (R)-S-benzyl-α-methylcysteine from Nickel (II) Complex Having (R)-S-benzyl-α-methylcysteine Moiety Under Acidic Conditions

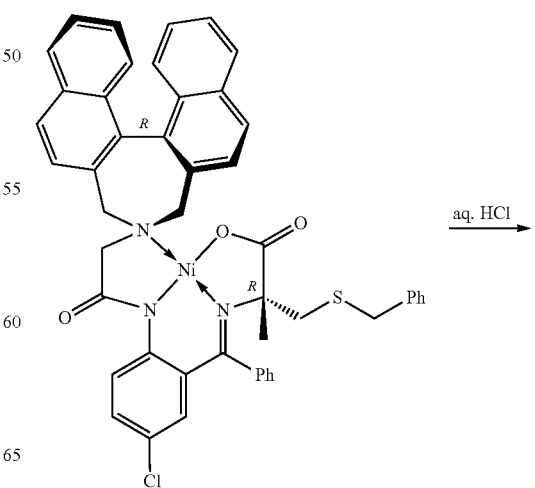

-continued

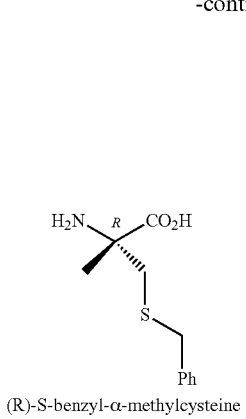
(R)-S-benzyl-α-methylcysteine

+

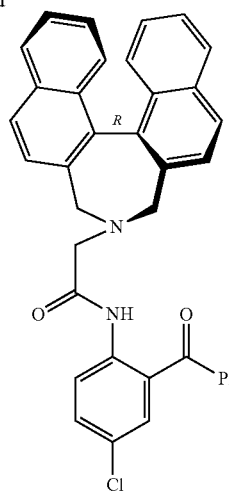

To a suspension of a nickel (II) complex having an (R)-S-benzyl-α-methylcysteine moiety (435 mg, 0.523 mmol) in methanol (13 mL), 1 N hydrochloric acid (3.0 mL, 2.62 mmol) was added, and the mixture was stirred at 40 to 50° C. for 1 hour. The reaction mixture was concentrated under reduced pressure, and the residue was subjected to phase separation with dichloromethane (20 mL) and water (20 mL). The organic layer was washed with 2% aqueous ammonia (10 mL, twice), with water (10 mL, twice), and then with saturated brine (10 mL, twice). The organic layer was dried over sodium sulfate, and then the solvent was removed by evaporation to give a chiral auxiliary (R-isomer) (281 mg, yield: 95%).

Meanwhile, the aqueous layer was concentrated to dryness, and the resulting solid was dissolved in a mixed solvent of water (5.0 mL), 1 N hydrochloric acid (2.0 mL), and methanol (4.0 mL). The solution was passed through a cation exchange resin column [SK-1B, 10 mL, eluent: water and subsequently 2% aqueous ammonia] to give (R)-S-benzyl-α-methylcysteine (52 mg, 0.230 mmol, yield: 44%, >98% ee) as a pale yellow solid.

Figure 24:
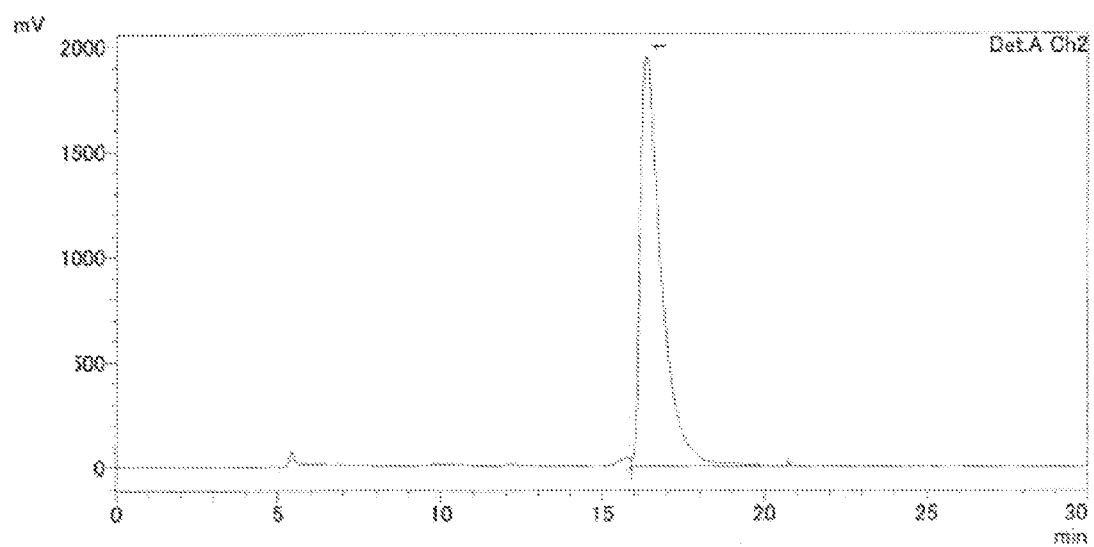
FIG. 24 shows a HPLC chromatogram of the compound prepared in Example 7-2.

HPLC analysis was conducted on the obtained compound under the following conditions. The results are shown in Table 25 and FIG. 24.

<HPLC Conditions: (R)-S-benzyl-α-methylcysteine Chiral Analysis Conditions>
Column: CHIROBIOTIC T (5 μm, 250×4.6 mm i.d.)
Eluent: A:B=50:50
  A=water
  B=ethanol
Flow rate: 0.3 mL/min
Temperature: 40° C.
Detector: UV 210 nm

TABLE 25

| Retention time in HPLC (min) | | |
|---|---|---|
| Objective substance S-benzyl-(R)-L-α-methylcysteine | Isomer of objective substance S-benzyl-(S)-D-α-methylcysteine | Excess ratio (objective substance:isomer of objective substance) |
| 16.3 | 17.7 (determined by analysis of racemic standard) | >98% ee (quantitation limit in indicated analysis conditions is at the level of 1%) |

Example 8: Synthesis of Nickel (II) Complex Having (S)-O-benzyl-α-methylserine Moiety by Reaction of Nickel (II) Complex Having Alanine Moiety and Benzyl Chloromethyl Ether

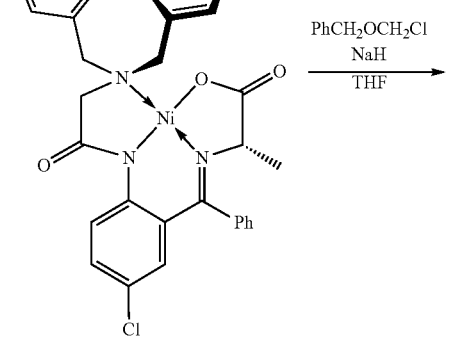

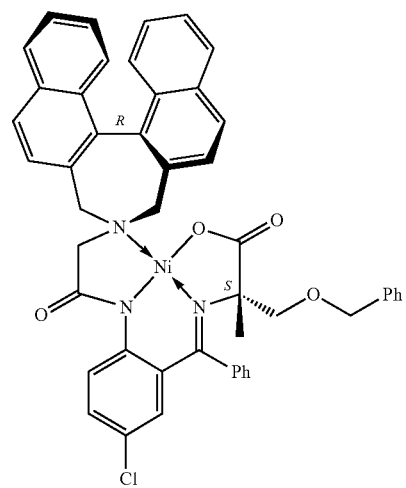

Under an argon atmosphere, to a THF solution (1.5 mL) of a nickel (II) complex having an alanine moiety (150 mg, 0.22 mmol), NaH (0.062 g, 10.295 mmol) and subsequently a THF solution (1.5 mL) of benzyl chloromethyl ether (0.169 g, 1.079 mmol) were added dropwise at −10 to 15° C. The mixture was stirred at the same temperature as above for 5 hours. After the end of the reaction, the reaction mixture was added to an ice-cooled 5% ammonium acetate aqueous solution (10 mL), and extraction was performed with methylene chloride (10 mL). The organic layer was washed with water (20 mL, twice) and then with saturated brine (20 mL), dried over sodium sulfate, and then concentrated to dryness. The concentrated residue was purified by silica gel column chromatography (benzene:acetone=95:5) to give a nickel (II) complex having an (S)-O-benzyl-α-methylserine moiety (70 mg, yield: 40.0%, >99.9% de) as red crystals.

ESI-MS (positive mode): m/z calcd for $C_{48}H_{38}ClN_3NiO_4$ $[M+H]^+$ 813.19. found 846.1 for $[M+MeOH+H]^+$.

$^1$H-NMR (200 MHz, $CDCl_3$): δ 0.74 (3H, s, α-Me), 2.77 [1H, d, J=11.9 Hz, one of azepine C(α)$H_2$N], 3.21 [1H, d, J=15.7 Hz, one of azepine C(α')$H_2$N], 3.35 and 3.67 (1H each, ABq, J=14.0 Hz, acetanilide NCOC$H_2$), 4.43 and 4.54 (1H each, ABq, J=11.8 Hz, β-C$H_2$ of the amino acid part), 4.45 [1H, d, J=15.7 Hz, one of azepine C (α')H₂N], 4.93 [1H, d, J=11.9 Hz, one of azepine C(α)H₂N], 5.05 (1H, d, J=6.0 Hz, one of OCH₂Ph), 5.72 (1H, d, J=6.0 Hz, one of OCH₂Ph), 6.73 (1H, d, J=2.6 Hz), 6.97-7.04 (1H, m, ArH), 7.15-7.57 (17H, m, ArH), 7.84 (1H, d, J=8.1 Hz, ArH), 7.92-8.00 (2H, m, ArH), 8.04 (1H, d, J=8.2 Hz, ArH), 8.65 (1H, d, J=9.3 Hz, ArH), 8.81 (1H, d, J=8.2 Hz, ArH).

¹³C-NMR (50.3 MHz, CDCl₃): δ 20.5 (Me), 58.3 (NCOCH₂), 61.7 and 66.1 (2×CH₂ of azepine), 71.7 (CH₂), one quaternary α-carbon of the amino acid part overlapping with signals of CDCl₃, 89.5 (CH₂), 124.9 (ArCH), 125.4 (quaternary ArC), 126.0 (ArCH), 126.2 (ArCH), 126.3 (ArCH), 127.4 (ArCH), 127.5 (ArCH), 127.7 (ArCH), 127.9 (ArCH), 128.0 (ArCH), 128.2 (ArCH), 128.4 (ArCH), 128.5 (ArCH), 128.8 (ArCH), 129.0 (ArCH), 129.1 (quaternary ArC), 129.2 (quaternary ArC), 130.0 (ArCH), 131.2 (quaternary ArC), 131.3 (quaternary ArC), 131.7 (quaternary ArC), 132.6 (ArCH), 133.6 (quaternary ArC), 133.8 (ArCH), 133.9 (quaternary ArC), 135.2 (quaternary ArC), 135.6 (quaternary ArC), 135.9 (quaternary ArC), 136.7 (quaternary ArC), 142.3 (quaternary ArC), 168.5, 170.5, 174.6 (CN and 2×CO).

Figure 25:
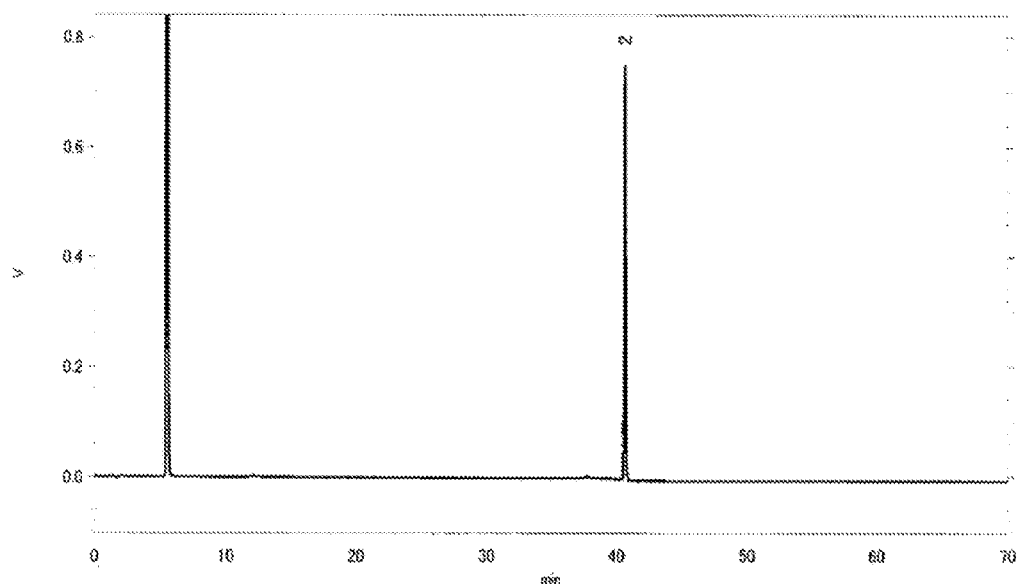
FIG. 25 shows a HPLC chromatogram of the compound prepared in Example 8.

HPLC analysis was conducted on the obtained compound under the following conditions. The results are shown in Table 26 and FIG. 25.

<HPLC Conditions: Complex Analysis Conditions>
Column: Inertsil ODS-3 (3 µm, 150×4.6 mm i.d.)
Eluent: A:B=40:60 to 0:100 (0 to 50 min)
A=10 mM ammonium formate in 0.1% formic acid buffer solution
B=acetonitrile
Flow rate: 1.0 mL/min
Temperature: 30° C.
Detector: UV 254 nm

TABLE 26

| Retention time in HPLC (min) | | |
|---|---|---|
| Objective substance O-benzyl-(S)-L-α-methylserine | Isomer of objective substance O-benzyl-(R)-D-α-methylserine | Excess ratio (objective substance:isomer of objective substance) |
| 40.6 | 36.4 | >99.9% de (99.96:0.04) |

Example 9-1: Synthesis of Nickel (II) Complex Having (1R,2S)vinylcyclopropane-carboxylic acid Moiety by Reaction of Nickel (II) Complex Having Glycine Moiety and trans-1,4-dibromo-2-butene

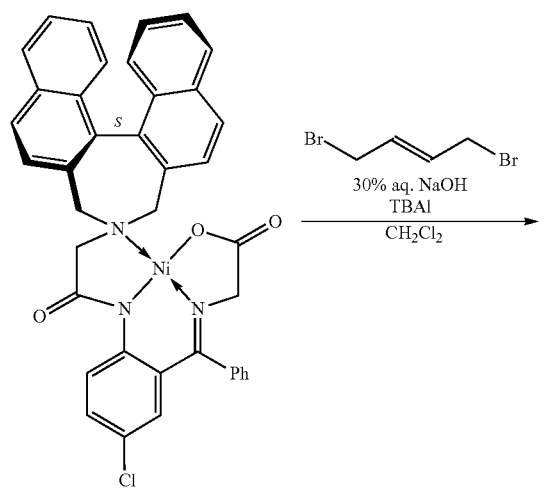

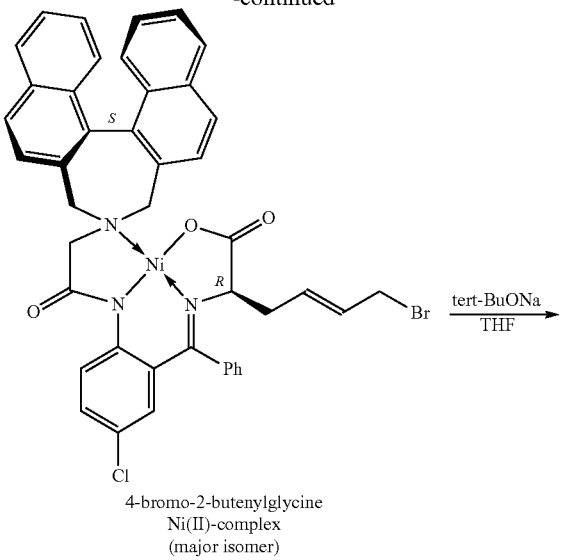

4-bromo-2-butenylglycine Ni(II)-complex (major isomer)

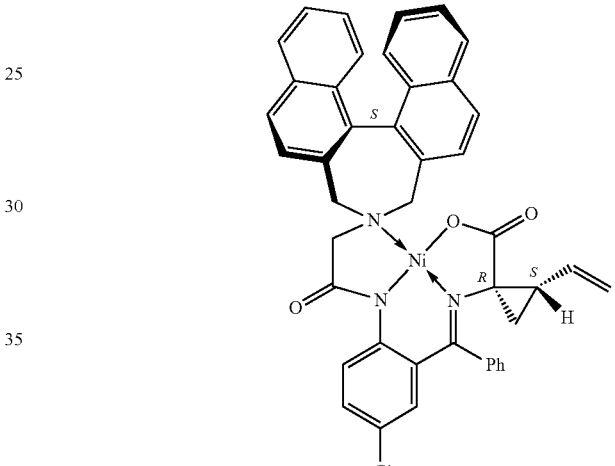

Under the atmosphere, to a dichloromethane solution (1320 mL) of a glycine equivalent (S-isomer) (33.0 g, 0.049 mol), trans-1,4-dibromo-2-butene (103.7 g, 0.485 mol), tetrabutylammonium iodide (4.5 g, 0.012 mol) and a 30% sodium hydroxide aqueous solution (1320 mL, 9.9 mol) were added. The mixture was stirred at room temperature for 30 minutes. The reaction mixture was subjected to phase separation, and the aqueous layer was extracted with dichloromethane (800 mL) twice. The organic layers were combined and washed with water (900 mL) twice and dried over sodium sulfate (350 g), and then the filtrate was concentrated to give an orange-red solid (162.9 g). The obtained orange-red solid was purified by silica gel column chromatography (dichloromethane:acetone=10:1) to give a nickel (II) complex having a 4-bromo-2-butenylglycine moiety (34.2 g, yield: 86.7%, diastereomeric ratio (S-R:S-S): 70:30) as red crystals.

ESI-MS (positive mode): m/z calcd for $C_{43}H_{33}BrClN_3NiO_3$ [M+H]⁺ 812.08. found 812.1.

Major Diastereomer Data

¹H-NMR (200 MHz, CDCl₃, major diastereomer data): δ 2.14-2.56 (2H, m, β-CH₂), 2.70 [1H, d, J=12.1 Hz, one of azepine C(α)H₂N], 3.03 [1H, d, J=15.6 Hz, one of azepine C(α')H₂N], 3.69 and 3.81 (1H each, ABq, J=14.0 Hz, acetanilide NCOCH₂), 4.23 (2H, dd, J=7.0, 0.9 Hz, BrCH₂), 4.38-4.46 (1H, m, α-CH), 4.69 [1H, d, J=15.6 Hz, one of azepine C(α')H$_2$N], 4.82 [1H, d, J=12.1 Hz, one of azepine C(α)H$_2$N], 5.80-6.06 (2H, m, 2×olefinic CH), 6.66 (1H, d, J=2.6 Hz, ArH), 6.91-6.99 (1H, m, ArH), 7.08-7.61 (12H, m, ArH), 7.92-8.02 (3H, m, ArH), 8.14 (1H, d, J=8.2 Hz, ArH), 8.46 (1H, d, J=9.2 Hz, ArH), 8.73 (1H, d, J=8.2 Hz, ArH).

$^{13}$C-NMR (50.3 MHz, CDCl$_3$, only main signals of major diastereomer): δ 32.5 (CH$_2$), 36.3 (CH$_2$), 58.6 (NCOCH$_2$), 61.9 and 66.4 (2×CH$_2$ of azepine), 70.5 (CH), 170.5, 174.7, 177.6 (CN and 2×CO).

Subsequently, under an argon atmosphere, to a THF solution (1060 mL) of a nickel (II) complex having a 4-bromo-2-butenylglycine moiety (53.0 g, 0.0651 mol), a 2 M solution (48.8 mL, 0.098 mol) of sodium tert-butoxide in THF was added dropwise at 0° C., and the mixture was stirred at 0° C. for 10 minutes. The reaction mixture was subjected to phase separation with water (500 mL) and dichloromethane (500 mL). The organic layer was separated, and then the aqueous layer was extracted with dichloromethane (500 mL) twice. The organic layers were combined and dried over sodium sulfate (270 g), and then the filtrate was concentrated to dryness to give an orange-red solid (51.5 g). The obtained orange-red solid was slurry-washed with ethyl acetate (250 mL, 5 v/w) for 2 hours. The crystals were separated by filtration and further washed with ethyl acetate (100 mL, 2 v/w) to give a nickel (II) complex having a (1R,2S)-1-amino-2-vinylcyclopropane-carboxylic acid moiety (43.0 g, yield: 90.0%, 99.5% de) as red crystals.

ESI-MS (positive mode): m/z calcd for C$_{43}$H$_{32}$ClN$_3$NiO$_3$ [M+H]$^+$ 732.16. found 732.4.

$^1$H-NMR (200 MHz, CDCl$_3$): δ 0.33 (1H, dd, J=9.8, 7.1 Hz, one of CH$_2$ of cyclopropane), 1.48 (1H, dd, J=9.3, 7.1 Hz, one of CH$_2$ of cyclopropane), 1.91-2.07 (1H, m, CH of cyclopropane), 2.67 [1H, d, J=12.1 Hz, one of azepine C(α)H$_2$N], 3.03 [1H, d, J=15.6 Hz, one of azepine C(α') H$_2$N], 3.58 and 3.65 (1H each, ABq, J=14.0 Hz, acetanilide NCOCH$_2$), 4.60 [1H, d, J=15.6 Hz, one of azepine C(α') H$_2$N], 4.69 [1H, d, J=12.1 Hz, one of azepine C(α)H$_2$N], 5.27-5.34 (1H, m, vinylic CH), 5.59-5.67 (2H, m, vinylic CH$_2$), 6.66 (1H, d, J=2.4 Hz, ArH). 6.81-6.89 (1H, m, ArH), 7.12-7.19 (1H, m, ArH), 7.20-7.61 (11H, m, ArH), 7.93-8.02 (3H, m, ArH), 8.16 (1H, d, J=8.2 Hz, ArH), 8.41 (1H, d, J=9.2 Hz, ArH), 8.81 (1H, d, J=8.4 Hz, ArH).

$^{13}$C-NMR (50.3 MHz, CDCl$_3$): δ 25.8 (CH$_2$), 40.1 (CH), 58.8 (NCOCH$_2$). 61.5 and 66.6 (2×CH$_2$ of azepine), the signal due to one quaternary α-carbon of the amino acid part overlapping with that of CDCl$_3$, 118.4 (vinylic CH$_2$), 124.5 (ArCH), 126.1 (quaternary ArC), 126.3 (quaternary ArC), 126.4 (ArCH), 127.1 (ArCH), 127.3 (ArCH), 127.5 (ArCH), 127.8 (ArCH), 128.4 (ArCH), 128.6 (ArCH), 128.7 (ArCH), 129.1 (ArCH), 129.4 (ArCH), 129.5 (ArCH), 130.6 (ArCH), 131.0 (quaternary ArC), 131.2 (quaternary ArC), 131.5 (quaternary ArC), 132.6 (ArCH), 132.8 (ArCH), 133.7 (quaternary ArC), 134.0 (quaternary ArC), 134.6 (ArCH), 135.5 (quaternary ArC), 136.0 (quaternary ArC), 140.9 (quaternary ArC), 165.2, 173.2, 174.3 (CN and 2×CO).

Figure 26:
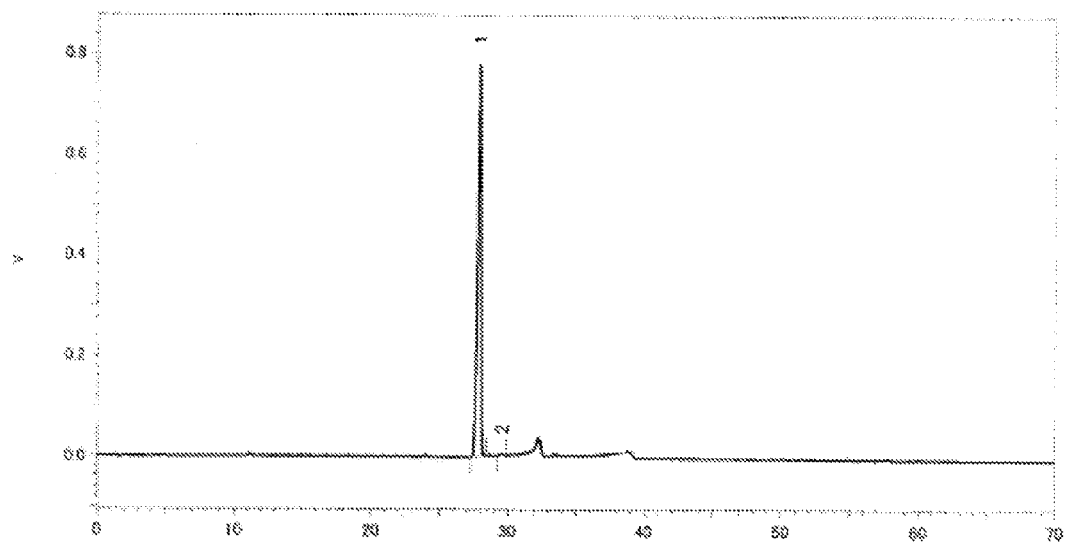
FIG. 26 shows a HPLC chromatogram of the compound prepared in Example 9-1.

HPLC analysis was conducted on the obtained compound under the following conditions. The results are shown in Table 27 and FIG. 26.

<HPLC Conditions: Complex Analysis Conditions>
Column: Inertsil ODS-3 (3 μm, 150×4.6 mm i.d.)
Eluent: A:B=40:60 to 0:100 (0 to 50 min)
A=10 mM ammonium formate in 0.1% formic acid buffer solution
B=acetonitrile
Flow rate: 1.0 mL/min
Temperature: 30° C.
Detector: UV 254 nm

TABLE 27

| Retention time in HPLC (min) | | Excess ratio (objective substance:isomer of objective substance) |
|---|---|---|
| Objective substance | Isomer of objective substance | |
| 27.90 | 29.51 | 99.5% de (99.8:0.3) |

Example 9-2: Release of (1R,2S)vinylcyclopropane-carboxylic acid from nickel (II) Complex Having (1R,2S)vinylcyclopropane-carboxylic acid Moiety Under Acidic Conditions, Protection of (1R,2S)vinylcyclopropane-carboxylic acid with Boc Group, and Determination of Optical Purity of (1R,2S)vinylcyclopropane-carboxylic acid

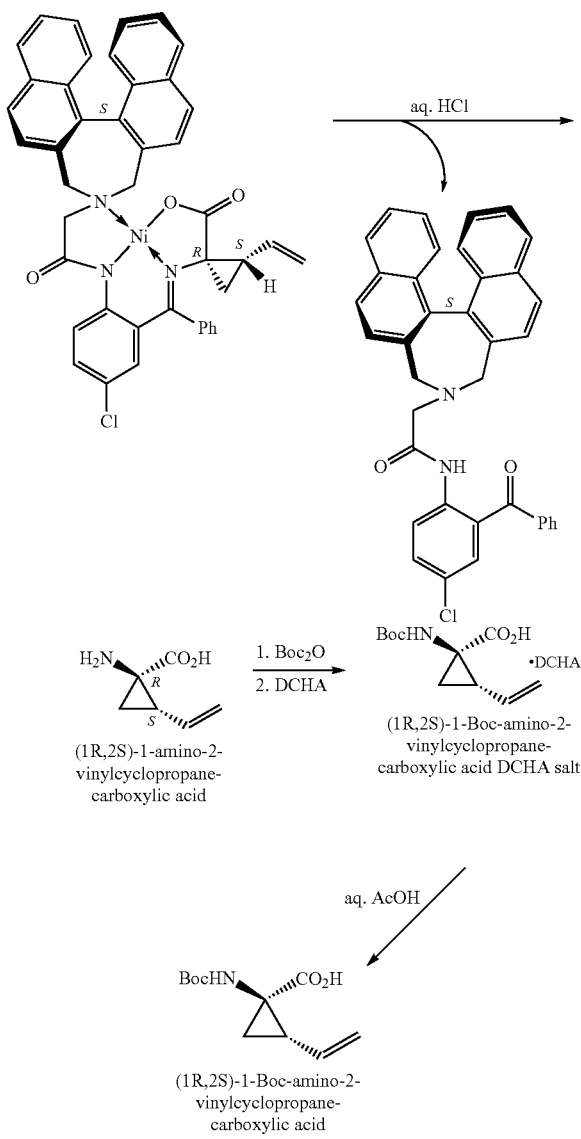

To a suspension of a nickel (II) complex having a (1R,2S)vinylcyclopropane-carboxylic acid moiety (32.0 g, 0.0437 mol) in methanol (960 mL), 1 N hydrochloric acid (218.5 mL, 0.218 mol) was added, and the mixture was stirred at 50° C. for 1 hour. The methanol was removed from the reaction mixture under reduced pressure, and the residue was subjected to phase separation with water (300 mL) and ethyl acetate (300 mL). The aqueous layer was washed with ethyl acetate (200 mL) and then concentrated to dryness. The obtained solid was dissolved in water (200 mL), 6 N hydrochloric acid (7 mL), and methanol (50 mL). The solution was passed through a cation exchange resin column [SK-1B, 200 mL, eluent: 2% aqueous ammonia (800 mL) and 4% aqueous ammonia (1400 mL)] to give (1R,2S) vinylcyclopropane-carboxylic acid (4.47 g, yield: 80.5%). Meanwhile, the organic layer was washed with water (200 mL), with 2% aqueous ammonia (100 mL, twice), and with saturated brine (200 mL), dried over sodium sulfate, and then concentrated to dryness to give a chiral auxiliary (S-isomer) (23.0 g, yield: 92.8%).

Next, the (1R,2S)vinylcyclopropane-carboxylic acid (4.47 g, 0.0352 mol) obtained by the above step was dissolved in water (100 mL) and acetone (100 mL). To the solution, (Boc)$_2$O (8.4 g, 0.039 mol) and triethylamine (3.9 g, 0.039 mol) were added. The mixture was stirred at room temperature for 15 hours. To this, (Boc)$_2$O (3.8 g, 0.0175 mol) and triethylamine (1.8 g, 0.0176 mol) were further added. The mixture was stirred at room temperature for 5 hours. The reaction mixture was concentrated until the volume was reduced to 100 mL or less, and citric acid (solid) was added thereto to adjust the pH of the aqueous layer to 2 to 3. The aqueous layer was extracted with ethyl acetate (100 mL, 3 times). The organic layers were combined and washed with water (100 mL) and with saturated brine (100 mL), and dried over sodium sulfate. The filtrate was concentrated to give (1R,2S)-1-Boc-amino-2-vinylcyclopropane-carboxylic acid (8.6 g, yield: quantitative) as a yellow oily substance. The obtained (1R,2S)-1-Boc-amino-2-vinylcyclopropane-carboxylic acid (8.6 g) was dissolved in ethyl acetate (34.4 mL, 4 v/w). To the solution, dicyclohexylamine (6.4 g, 0.0352 mol) was gradually added, and the mixture was stirred at room temperature for 20 hours and then at 0° C. for 1 hour. The precipitated crystals were separated by filtration and washed with ethyl acetate (34 mL, 4 v/w) cooled to 0° C. to give a (1R,2S)-1-Boc-amino-2-vinylcyclopropane-carboxylic acid DCHA salt (11.5 g, yield for 2 steps: 80.0%) as white crystals.

$^1$H-NMR (200 MHz, CD$_3$OD): δ 1.10-1.49 (10H, m), 1.43 (9H, s, tBu), 1.61-2.16 (13H, m), 3.06-3.22 (2H, m, 2×CHN), 4.92 (1H, dd, J=10.3, 2.2 Hz), 5.15 (1H, dd, J=17.3, 2.2 Hz), 5.88 (1H, ddd, J=17.3, 10.3, 9.8 Hz).

$^{13}$C-NMR (50.3 MHz, CD$_3$OD): δ 23.1 (3-CH$_2$), 25.7 (CH$_2$ of DCHA), 26.3 (CH$_2$ of DCHA), 29.0 (Me$_3$C), 30.7 (CH$_2$ of DCHA), 33.4 (2-CH), 44.0 (1-C, quaternary), 54.4 (CH of DCHA), 80.0 (Me$_3$C), 115.3 (CH=CH$_2$), 138.4 (CH=CH$_2$), 158.1 (CON), 177.5 (CO$_2$H).

The obtained (1R,2S)-1-Boc-amino-2-vinylcyclopropane-carboxylic acid DCHA salt (400 mg, 0.979 mmol) was suspended in ethyl acetate (4 mL). At 0° C., a 5% acetic acid aqueous solution (4 mL) was added dropwise to the suspension, and the mixture was stirred for 30 minutes. The reaction mixture was subjected to phase separation with water (10 mL), and the aqueous layer was extracted with ethyl acetate (10 mL, 3 times). The organic layers were combined and washed with water (10 mL) twice and dried over sodium sulfate. The solvent was removed by evaporation to give (1R,2S)-1-Boc-amino-2-vinylcyclopropane-carboxylic acid (236 mg, yield: quantitative, 99.6% ee).

$^1$H-NMR (200 MHz, CDCl$_3$): δ 1.24 (1H, dd, J=9.3, 4.9 Hz, one of 3-H$_2$), 1.37 (9H, s, tBu), 1.44-1.58 (1H, m, one of 3-H$_2$), 2.05 (1H, dt, J=10.3, 9.3 Hz, 2-H), 5.04 (1H, dd, J=10.3, 2.2 Hz), 5.22 (1H, dd, J=17.0, 2.2 Hz), 5.68 (1H, dt, J=17.0, 10.3 Hz), 7.22 (1H×0.25, br s), 7.57 (1H×0.75, br s), 12.47 (1H, br s).

$^{13}$C-NMR (50.3 MHz, CDCl$_3$): δ 22.5 (3-CH$_2$ for major rotamer), 22.9 (3-CH$_2$ for minor rotamer), 28.2 (Me$_3$C), 32.5 (2-CH for major rotamer), 33.8 (2-CH for minor rotamer), 40.6 (1-C, quaternary), 78.0 (Me$_3$C), 116.8 (CH=CH$_2$), 135.0 (CH=CH$_2$), 155.5 (CON), 172.5 (CO$_2$H for major rotamer), 172.7 (CO$_2$H for minor rotamer).

Figure 27:
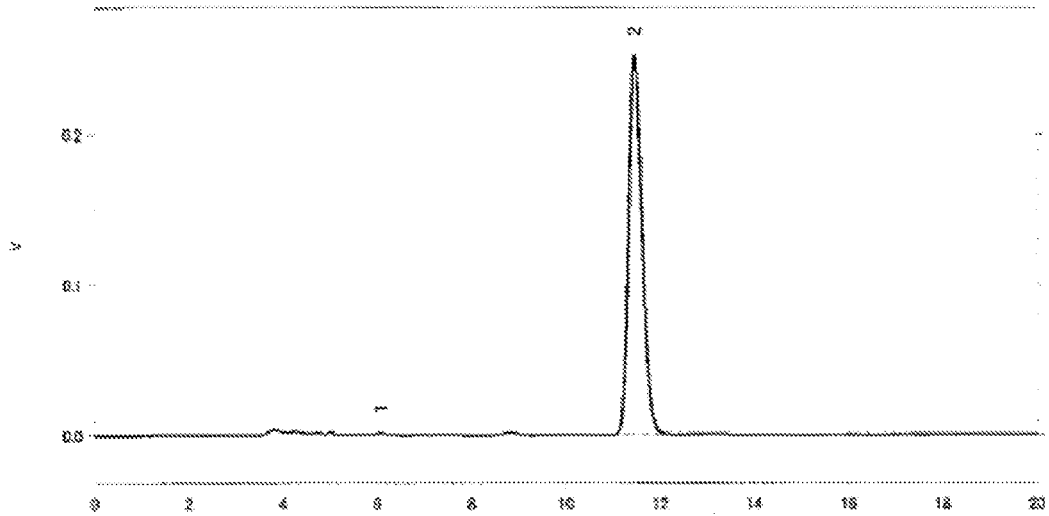
FIG. 27 shows a HPLC chromatogram of the compound prepared in Example 9-2.

HPLC analysis was conducted on the obtained compound under the following conditions. The results are shown in Table 28 and FIG. 27.

<HPLC Conditions: Chiral Analysis Conditions>
Column: CHIRALPAK AD-H (5 μm, 250×4.6 mm i.d.)
Eluent: A:B=20:80 (0 to 30 min)
  A=isopropanol
  B=hexane
Flow rate: 0.8 mL/min
Temperature: 30° C.
Detector: UV 220 nm

TABLE 28

| Retention time in HPLC (min) | | Excess ratio (isomer of objective substance:objective substance) |
|---|---|---|
| Isomer of objective substance | Objective substance | |
| 6.07 | 11.47 | 99.6% ee (0.2:99.8) |

Reference Example 2

Release of L-phenylalanine from Nickel (II) Complex Having L-phenylalanine Moiety Under Acidic Conditions and Protection of L-phenylalanine with Z Group

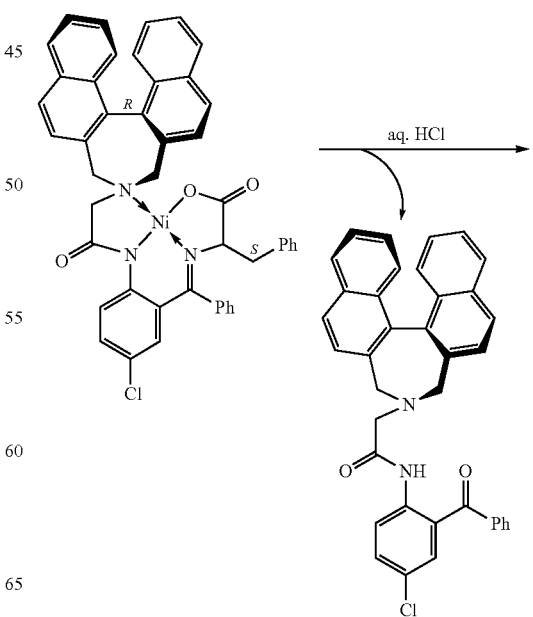

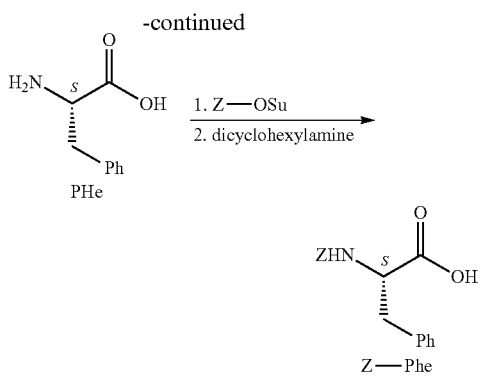

To a methanol suspension (12 mL) of a nickel (II) complex having an L-phenylalanine moiety (0.4 g, 0.52 mmol), 1 N hydrochloric acid (2.6 mL, 5 eq.) was added, and the mixture was stirred at 40° C. for 6 hours. After the end of the reaction, the reaction mixture was concentrated, and the residue was dissolved in dichloromethane (10 mL). The organic layer was extracted with 2% aqueous ammonia (6 mL, twice) and with water (6 mL, twice), and then washed with saturated brine (6 mL, twice).

The organic layer was dried over sodium sulfate, and the sodium sulfate was filtered off. The filtrate was concentrated to dryness to give a chiral auxiliary (R-isomer) (0.27 g, yield: 90%) as a pale yellow solid.

The aqueous ammonia layers and the aqueous layers resulting from the extraction were combined and concentrated to dryness. The obtained solid was dissolved in 9% aqueous ammonia (3 mL). The solution was passed through a cation exchange resin column [SK-1B, 9 mL, eluent: water and subsequently aqueous ammonia (2%→8%)] to give L-phenylalanine (0.083 g, crude product).

The L-phenylalanine (0.078 g) was dissolved in an aqueous solution (3 mL) of sodium hydrogen carbonate (0.041 mg, 1 eq.)-sodium carbonate (0.103 mg, 2 eq.), and acetone (1 mL). To the solution in an ice bath, an acetone solution (1 mL) of N-benzyloxycarbonyloxysuccinimide (0.121 g, 1 eq.) was added, and the mixture was stirred at room temperature for 3 hours. The reaction mixture was concentrated, and the residue was subjected to phase separation with ethyl acetate (18 mL) and 1 N hydrochloric acid (2.5 mL). The aqueous layer was extracted with ethyl acetate (18 mL). The organic layer was washed with saturated brine (5 mL, twice), dried over sodium sulfate, and then concentrated to give a yellow oily substance (0.182 g). The obtained yellow oily substance was dissolved in isopropyl alcohol (0.08 mL)-ethyl acetate (0.8 mL). To the solution, an ethyl acetate solution (0.4 mL) of dicyclohexylamine (0.094 g, 1 eq.) was added, and then ethyl acetate (2.0 mL) were further added. The mixture was stirred at room temperature for 9 hours. The precipitated crystals were separated by filtration, and then blow-dried at 50° C. to give a Z-L-phenylalanine DCHA salt (0.178 g, yield: 76%, 99.0% ee) as white crystals.

Figure 28:
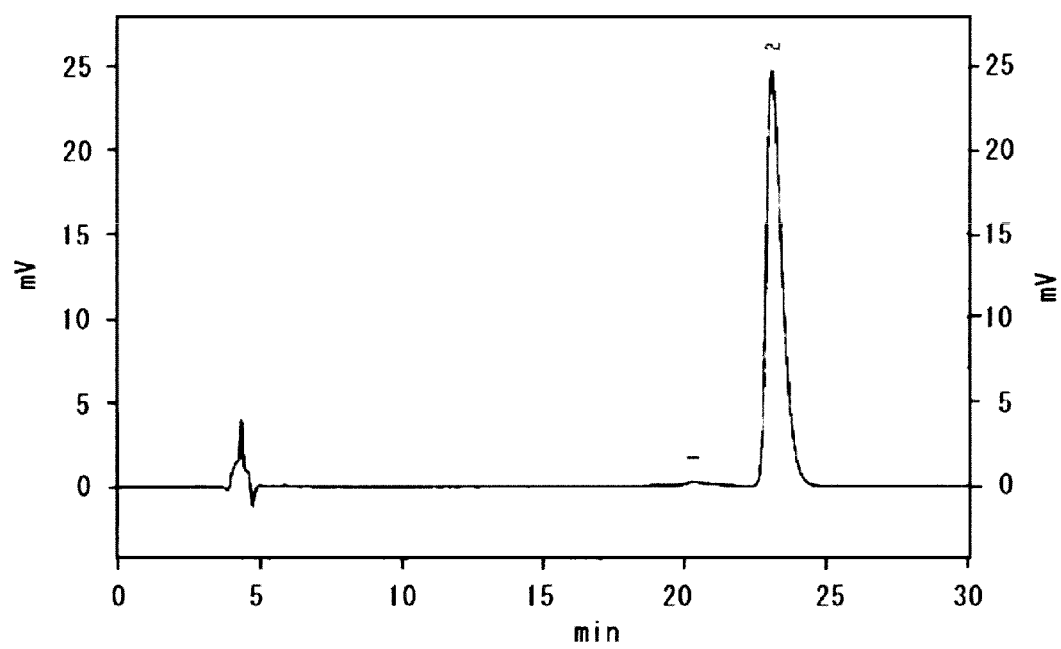
FIG. 28 shows a HPLC chromatogram of the compound prepared in Reference Example 2.

HPLC analysis was conducted on the obtained compound under the following conditions. The results are shown in Table 29 and FIG. 28.
<HPLC Conditions: Z-Phe Chiral Analysis Conditions>
Column: CHIRALCEL OJ-RH (5 μm, 150×4.6 mm i.d.)
Eluent: A:B=65:35 (0 to 30 min)
  A=0.1% phosphoric acid aqueous solution
  B=0.1% solution of phosphoric acid in acetonitrile
Flow rate: 0.5 mL/min
Temperature: 35° C.
Detector: UV 254 nm

TABLE 29

| Retention time in HPLC (min) | | Excess ratio |
| --- | --- | --- |
| Z-D-Phe | Z-Phe | (Z-D-Phe:Z-Phe) |
| 20.29 | 23.13 | 99.0% ee (0.5:99.5) |

INDUSTRIAL APPLICABILITY

According to the present invention, an optically active α-amino acid having a desired chirality can be produced in high yield and in a highly enantioselective manner. Moreover, according to the present invention, an optically active α,α-disubstituted α-amino acid, the importance of which in drug development has been increasing, can be produced in a high-yield, highly enantioselective and simple manner. Furthermore, according to the present invention, an intermediate useful for the above production methods of an optically active α-amino acid and an optically active α,α-disubstituted α-amino acid can be provided. Still further provided according to the present invention is a simple method for producing an unnatural optically active α-amino acid (D-form) from a natural optically active α-amino acid (L-form) or a mixture of optically active α-amino acids at any ratio.

The invention claimed is:
1. A metal complex represented by Formula (1-1):

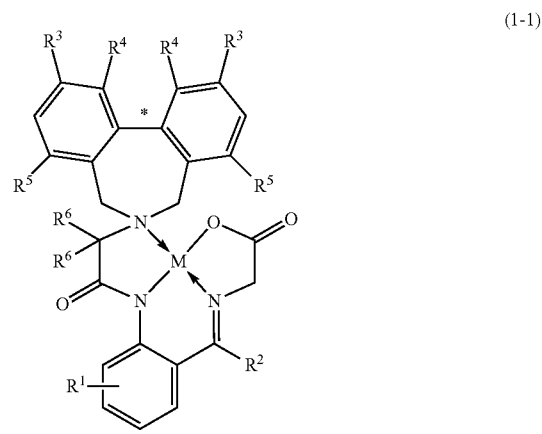

(1-1)

(wherein $R^1$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;
$R^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group;

R³ and R⁴ each independently denote hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two R³s may be the same or different;

the two R⁴s may be the same or different;

R³ and R⁴ may form a ring together with the carbon atoms to which they are bonded;

R⁵ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, an optionally substituted carboxyl group (—CO₂R⁷), or a halogen atom;

the two R⁵s may be the same or different;

R⁶ denotes hydrogen, an optionally substituted alkyl group, an optionally substituted cycloalkyl group, or a halogen atom;

the two R⁶s may be the same or different;

the two R⁶s may form a ring together with the carbon atom to which they are bonded;

R⁷ denotes hydrogen, an optionally substituted alkyl group, an optionally substituted aryl group, or an optionally substituted heteroaryl group;

* denotes a chiral axis; and

M denotes a divalent metallic cation), a metal complex represented by Formula (2):

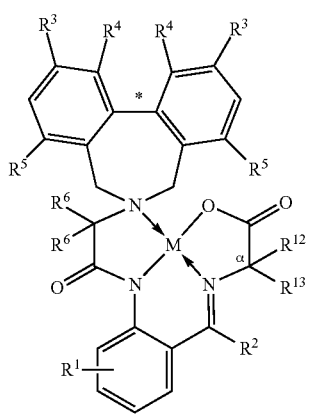

(2)

(wherein R¹ to R⁶, * and M have the same meanings as defined above; and R¹² and R¹³ each independently denote an optionally substituted alkyl group, an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, an optionally substituted aryloxycarbonyl group, or a halogen atom), or a metal complex represented by Formula (2):

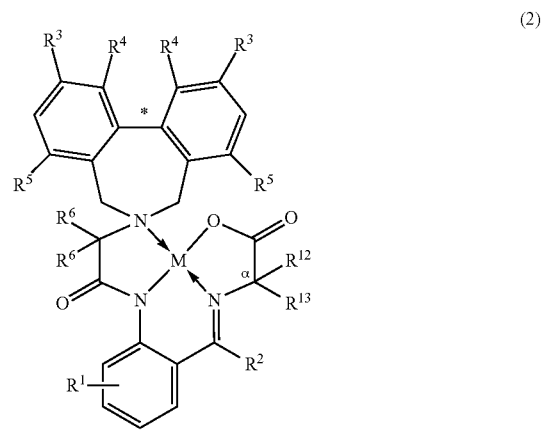

(2)

(wherein R¹ to R⁶, * and M have the same meanings as defined above; and R¹² and R¹³ each independently denote an optionally substituted alkyl group, an optionally substituted alkynyl group, an optionally substituted alkenyl group, an optionally substituted cycloalkyl group, an optionally substituted aryl group, an optionally substituted heteroaryl group, an optionally substituted aralkyl group, an optionally substituted heteroarylalkyl group, an optionally substituted alkoxycarbonyl group, an optionally substituted aryloxycarbonyl group, or a halogen atom, and R¹² and R¹³ may form a ring together with the carbon atom to which they are bonded).

2. The metal complex according to claim 1, wherein R¹ is hydrogen, chlorine, a methyl group, or a nitro group;

in each of the two pairs of R³ and R⁴, R³ and R⁴ form an aromatic or aliphatic cyclic structure together with the aromatic-ring carbon atoms to which they are bonded;

R⁵ and R⁶ are each hydrogen; and

R² is an aryl group represented by Formula (1-1a):

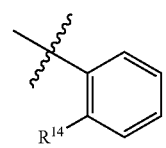

(1-1a)

(wherein R¹⁴ denotes a hydrogen atom or a halogen atom).

* * * * *